United States Patent [19]

Humphrey

[11] Patent Number: 4,640,596
[45] Date of Patent: Feb. 3, 1987

[54] OBJECTIVE REFRACTOR FOR THE EYE
[75] Inventor: William E. Humphrey, San Leandro, Calif.
[73] Assignee: Humphrey Instruments, Inc., San Leandro, Calif.
[21] Appl. No.: 406,607
[22] Filed: Aug. 9, 1982

Related U.S. Application Data
[63] Continuation-in-part of Ser. No. 202,536, Oct. 31, 1980, abandoned.
[51] Int. Cl.⁴ ............................................. A61B 3/10
[52] U.S. Cl. .................................... 351/211; 351/221; 351/205
[58] Field of Search ................ 351/205, 214, 221, 211

[56] References Cited
U.S. PATENT DOCUMENTS

| | | | |
|---|---|---|---|
| 3,715,166 | 2/1973 | Leighty et al. | 351/211 |
| 3,948,585 | 4/1976 | Heine et al. | 351/211 |
| 4,190,332 | 2/1980 | Body et al. | 351/211 |

Primary Examiner—Rodney B. Bovernick
Attorney, Agent, or Firm—Townsend and Townsend

[57] ABSTRACT

An objective refractor for the eye is disclosed in which knife-edge optics are utilized. The knife-edge optics cause characteristic illumination of the retina so that components of sphere and astigmatism can be identified. Provision for remote reading of the characteristic images is provided with the result that two orthogonally disposed knife-edge images can identify the sphere, cylinder and axis required for prescriptive patterns giving the direction and magnitude of required prescriptive change. A system of at least two orthogonally disposed, (and preferably four), knife edges with weighted lighting is disclosed for detection. Utilization of the knife-edge images is made possible by the detection of the low light level images at a detector having low noise level. A photo-sensitive element divided into a plurality of photo-discrete segments has light from the images proportionally dispersed over its surface. Such dispersion occurs through a matrix of wedge-shaped segments or alternately in the form of optical elements having cylindrical components. This dispersion of the light when used in combination with push-pull knife-edge patterns herein disclosed produces detectable low level refractive signal. An embodiment using an optic having a plurality of side by side optic elements, each element having the effect of crossed cylinders, is disclosed with the detector. Separate independent and non-interactive positional information on one hand, and refractive information on the other hand, is provided. Consequently the disclosed refractor is insensitive to adjustment and can accommodate a large range of pupil configuration with insensitivity to local retinal variations in light emission.

8 Claims, 51 Drawing Figures

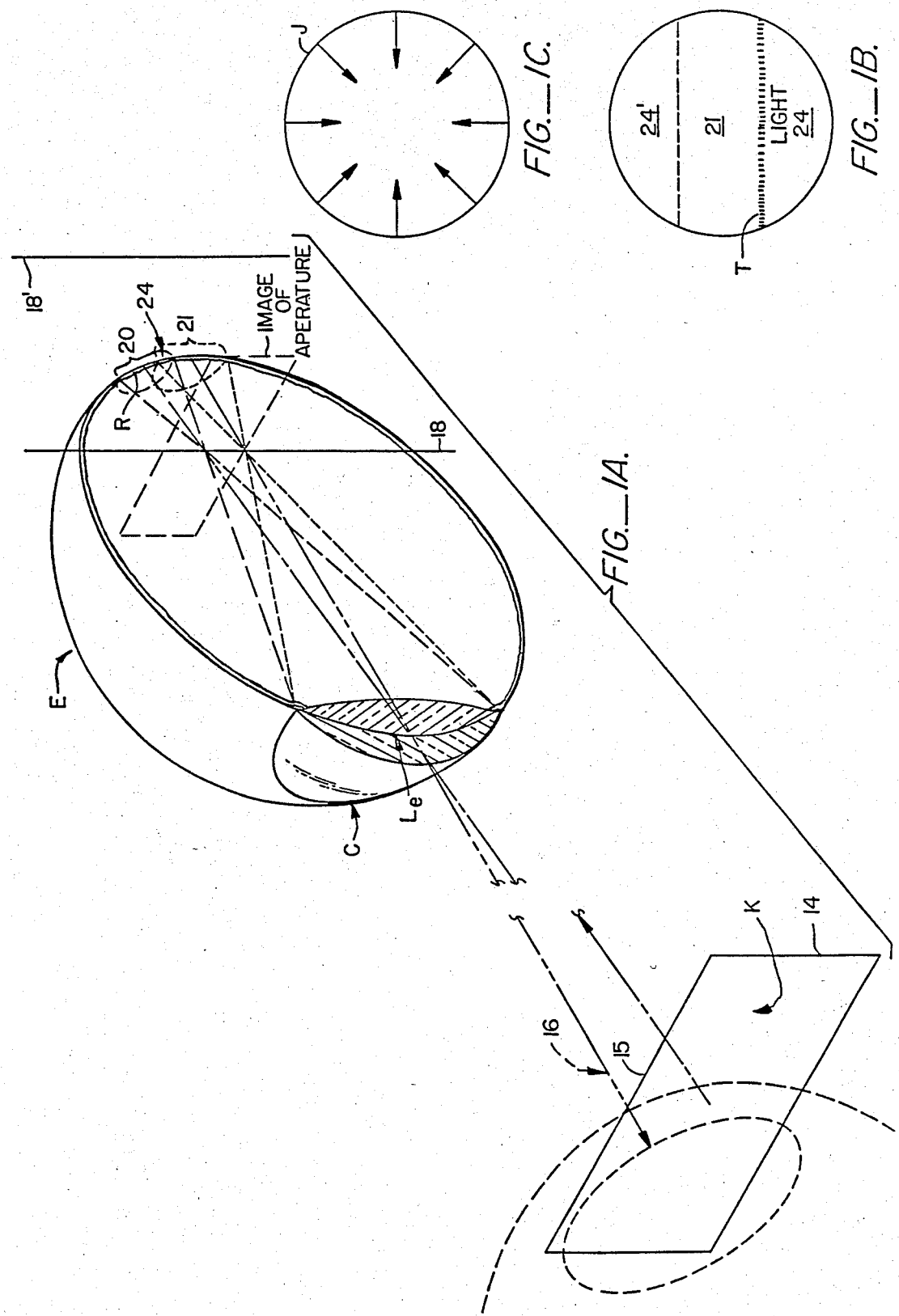

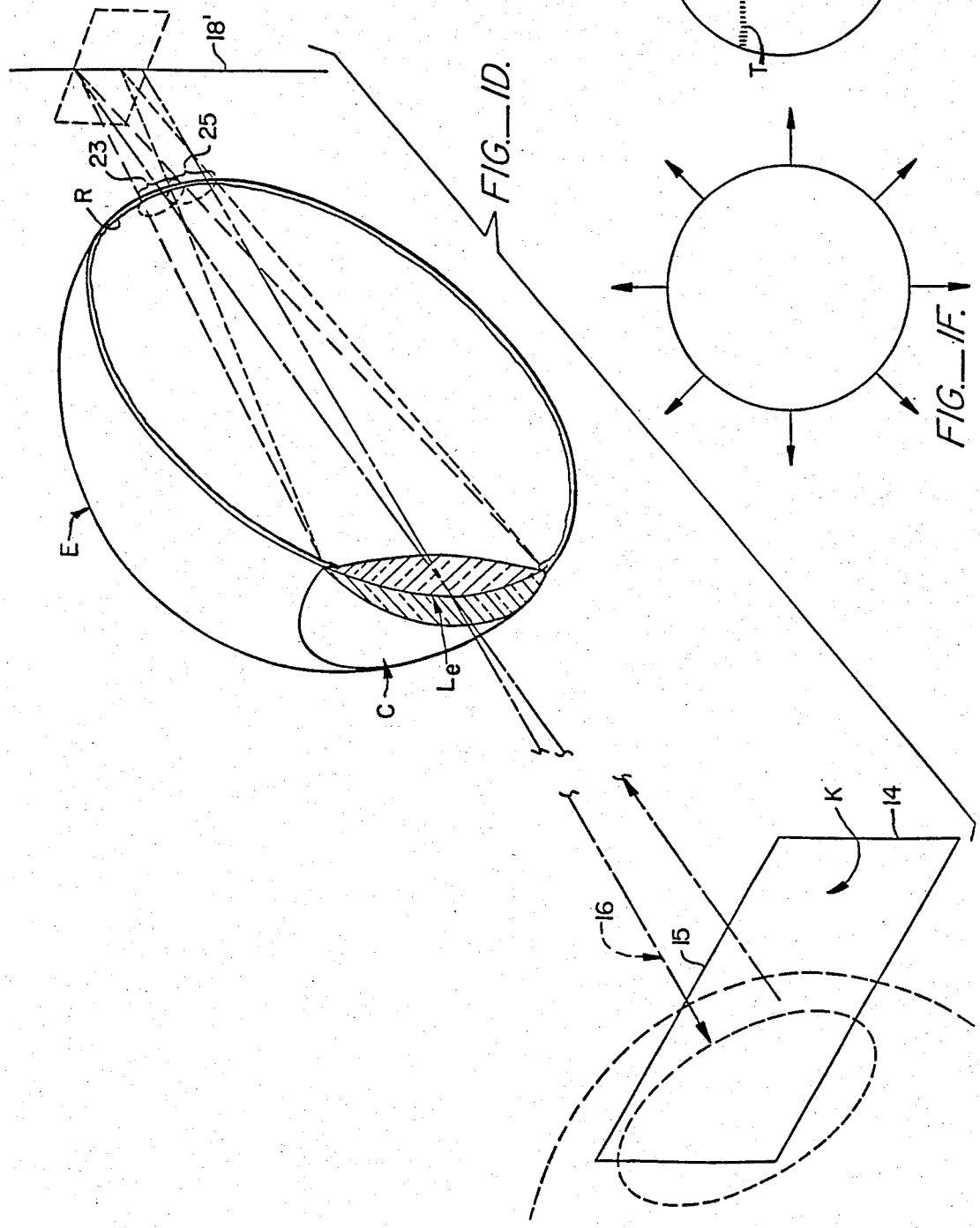

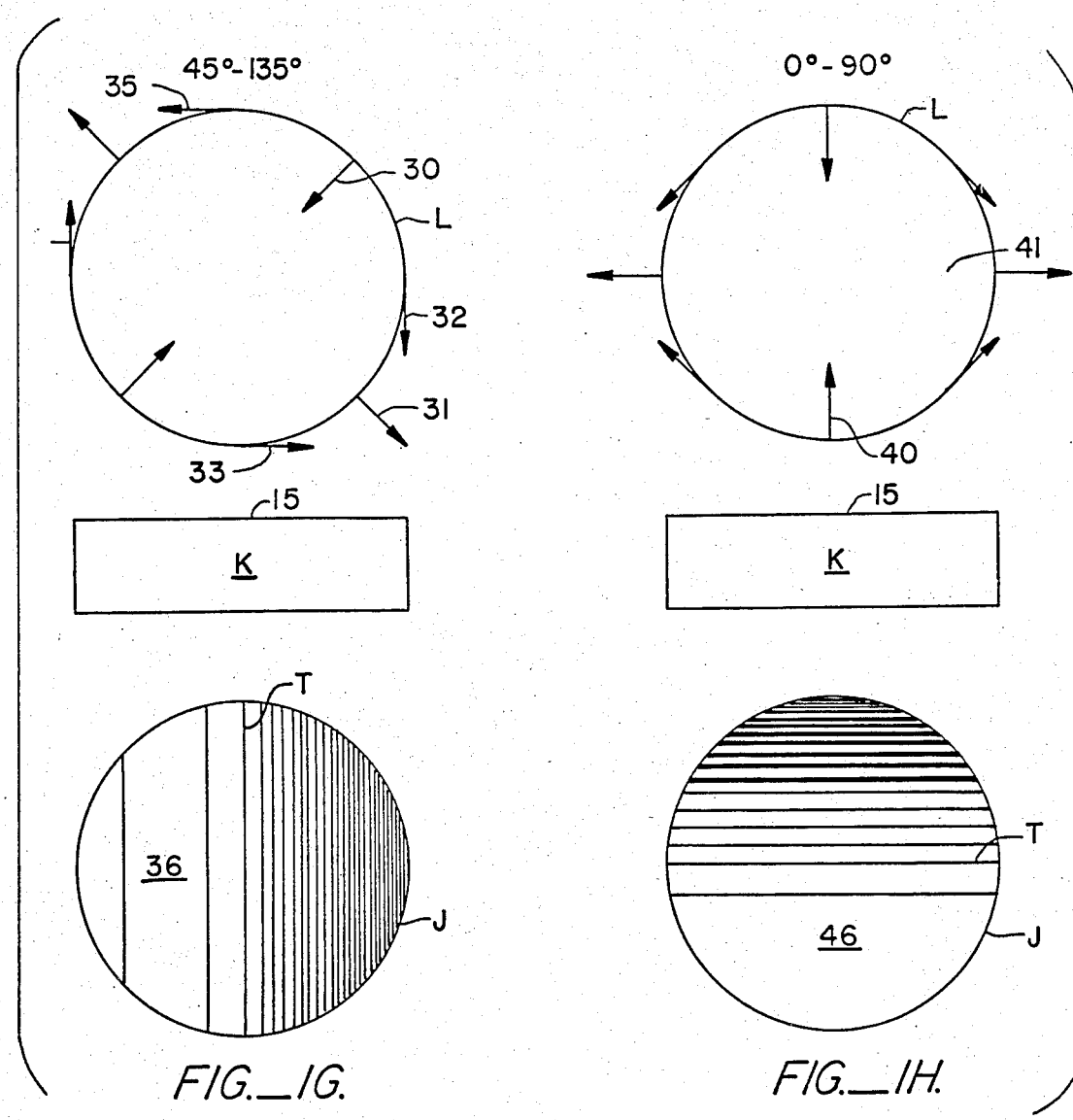
FIG._1G.   FIG._1H.

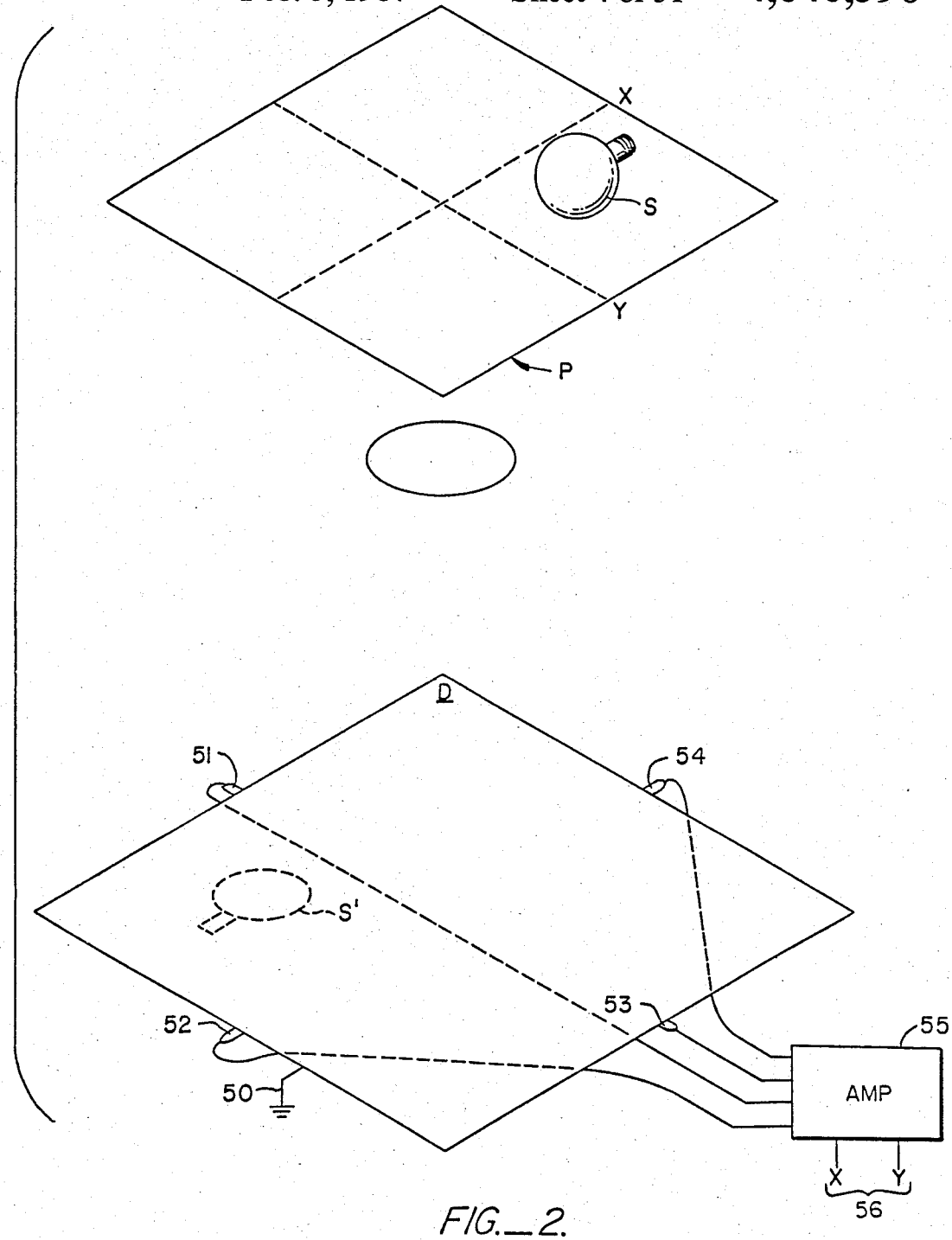
FIG._2.
PRIOR ART

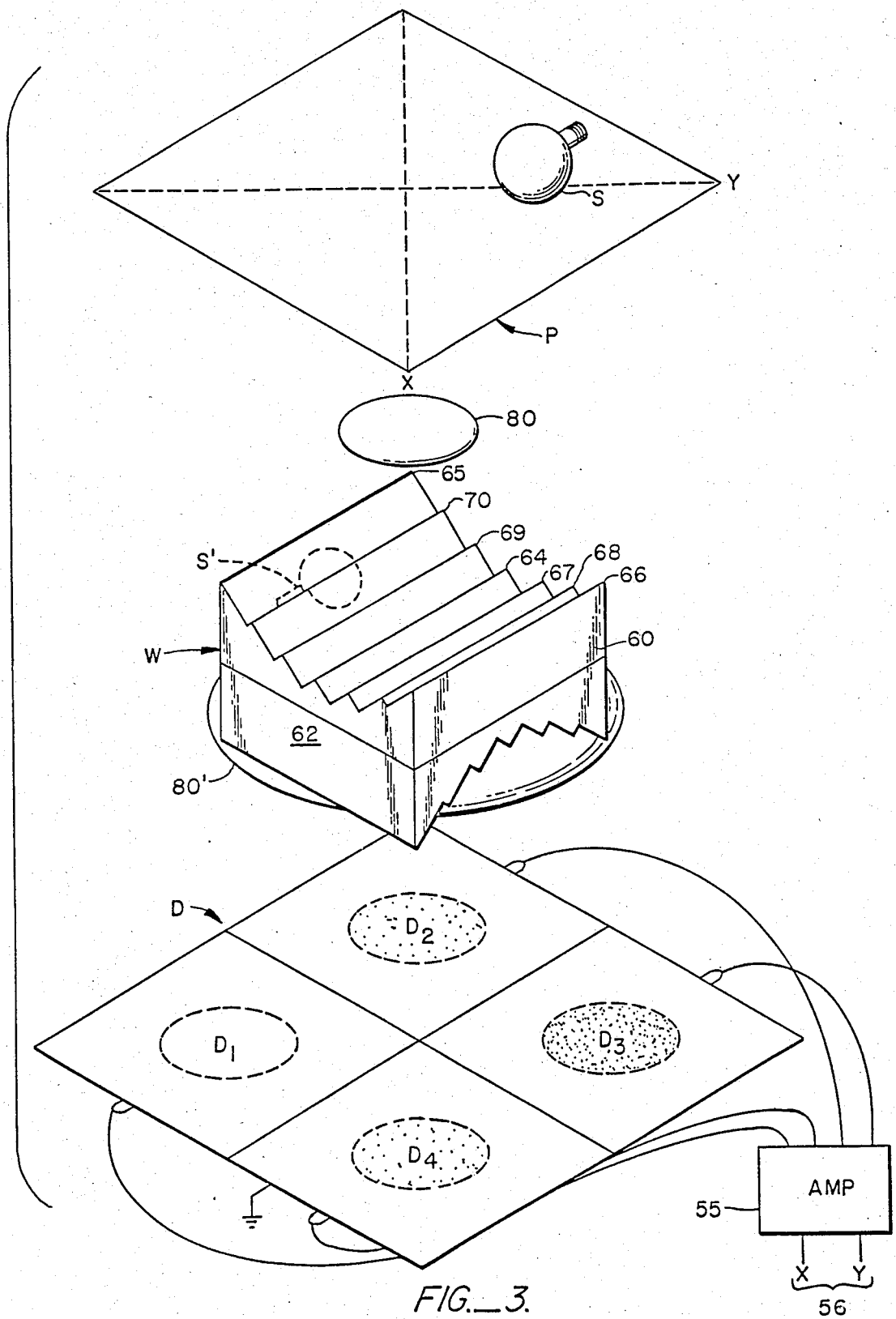
FIG._3.

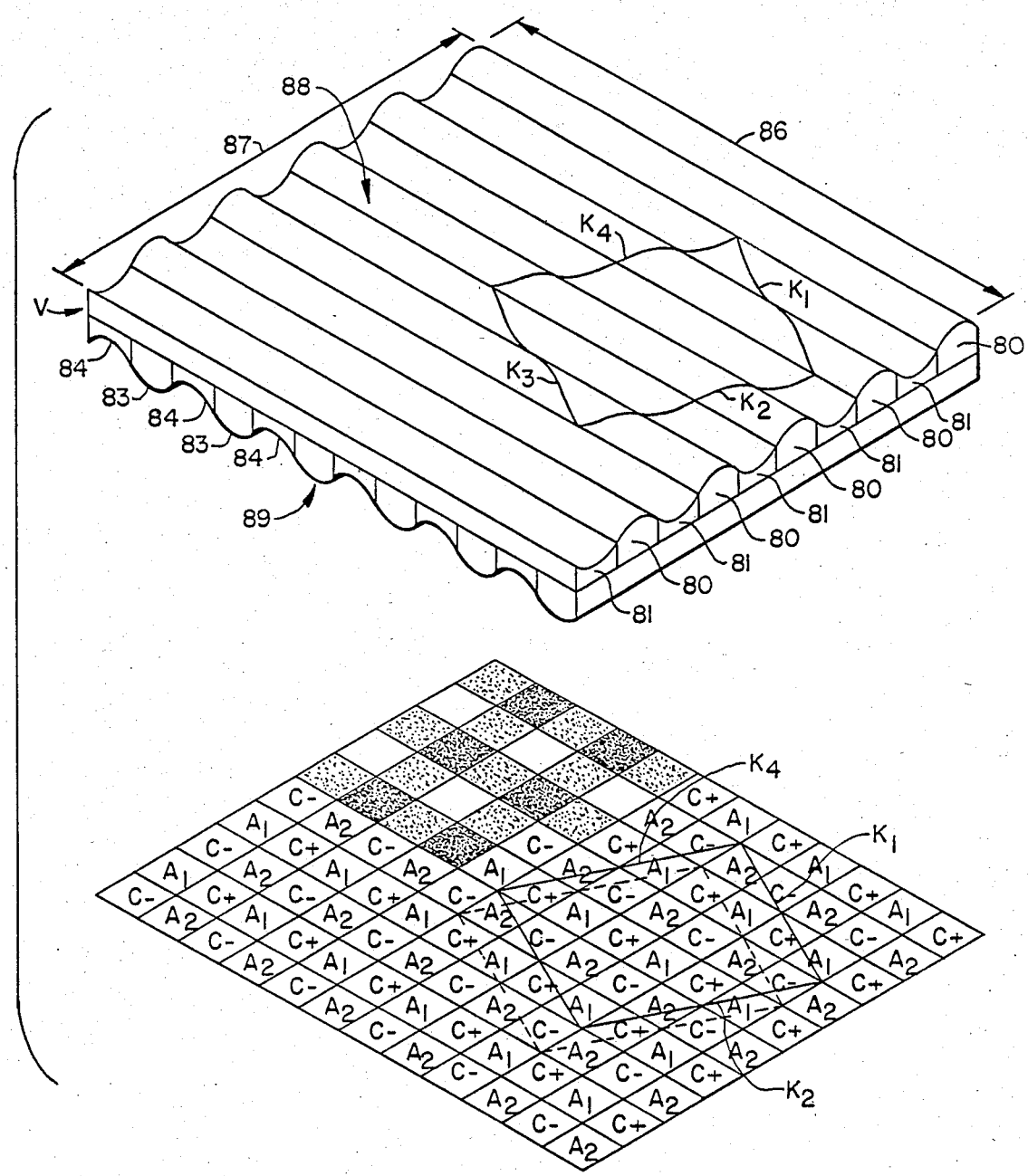
FIG._4A.

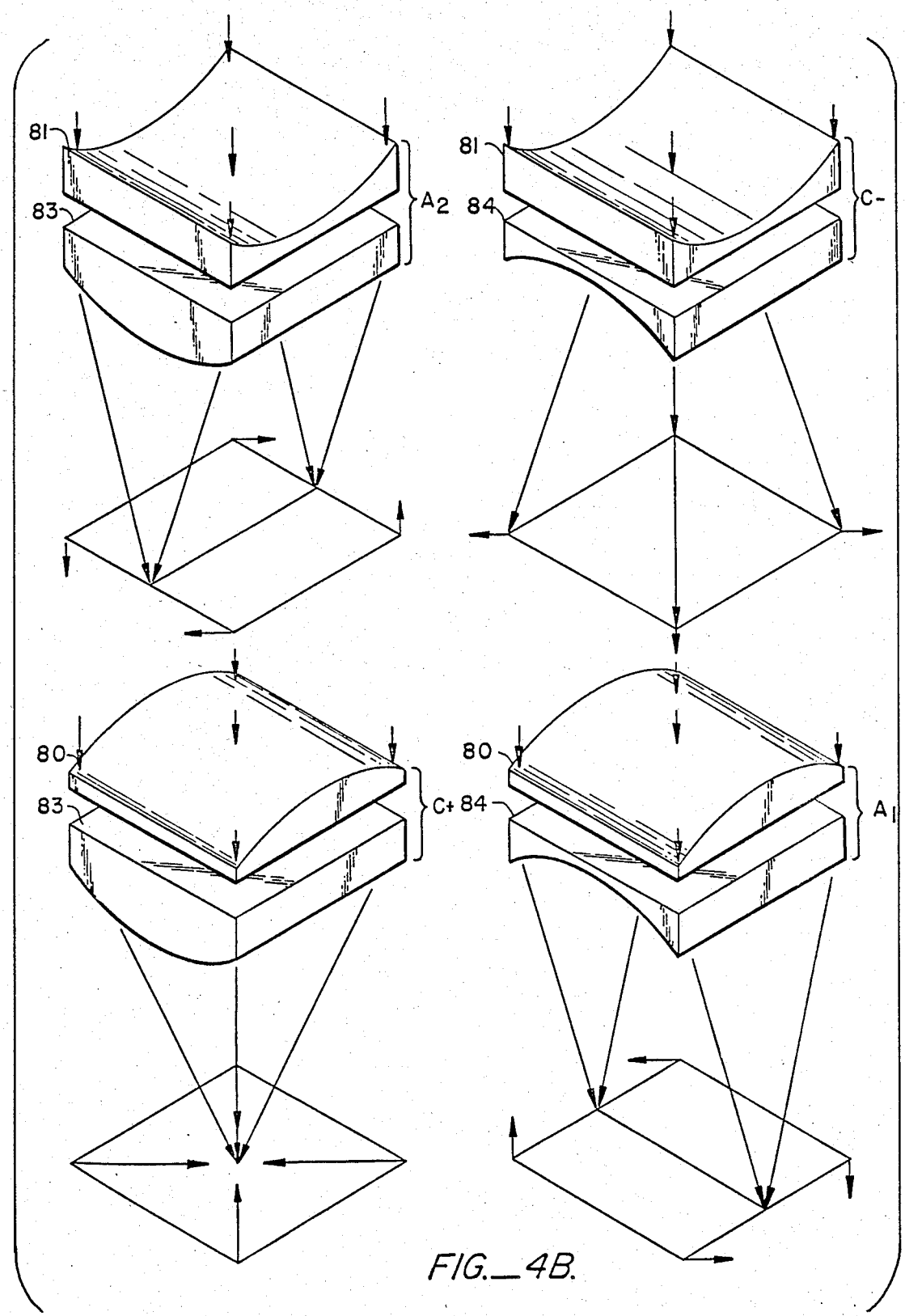
FIG._4B.

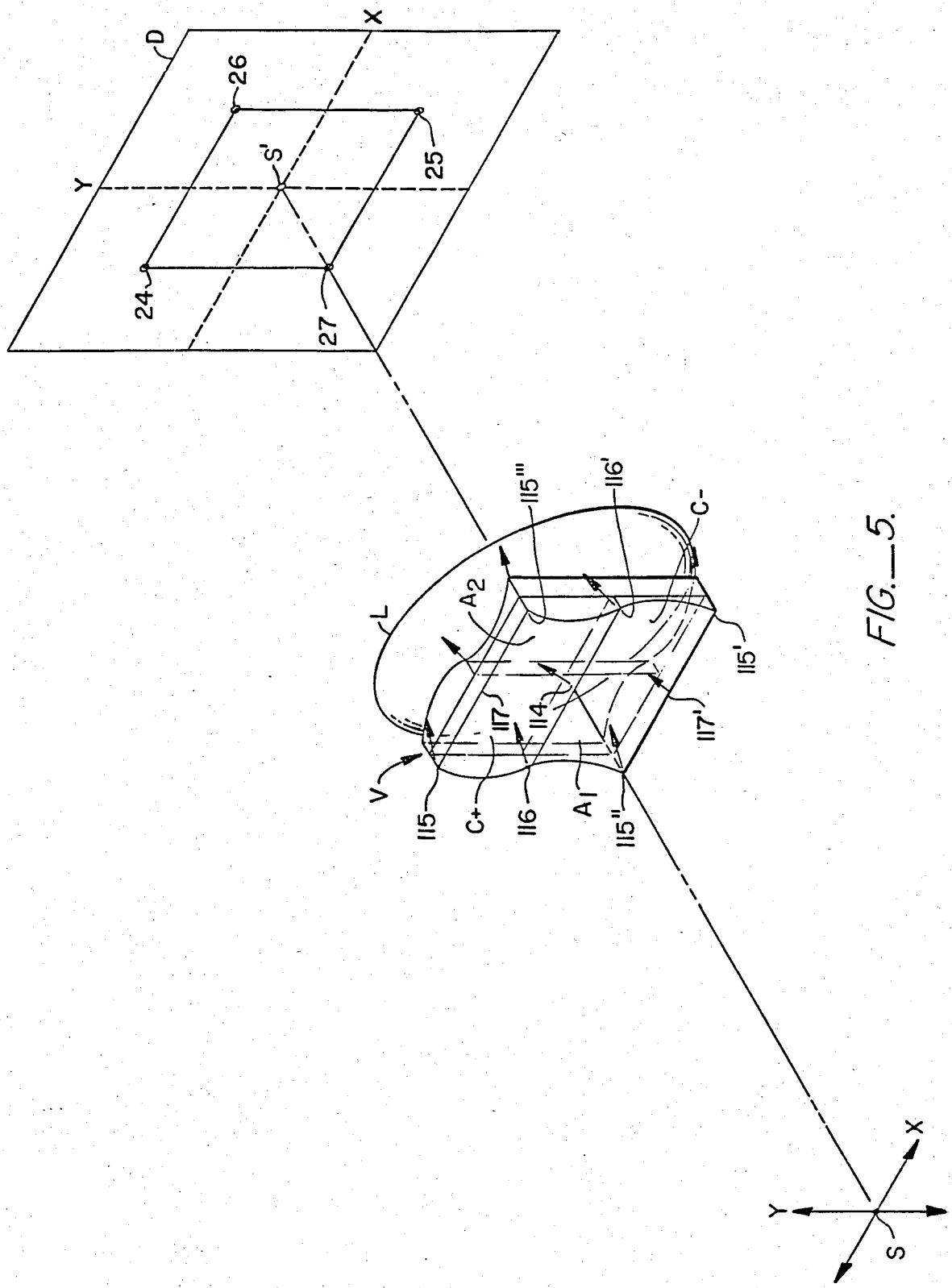
FIG._5.

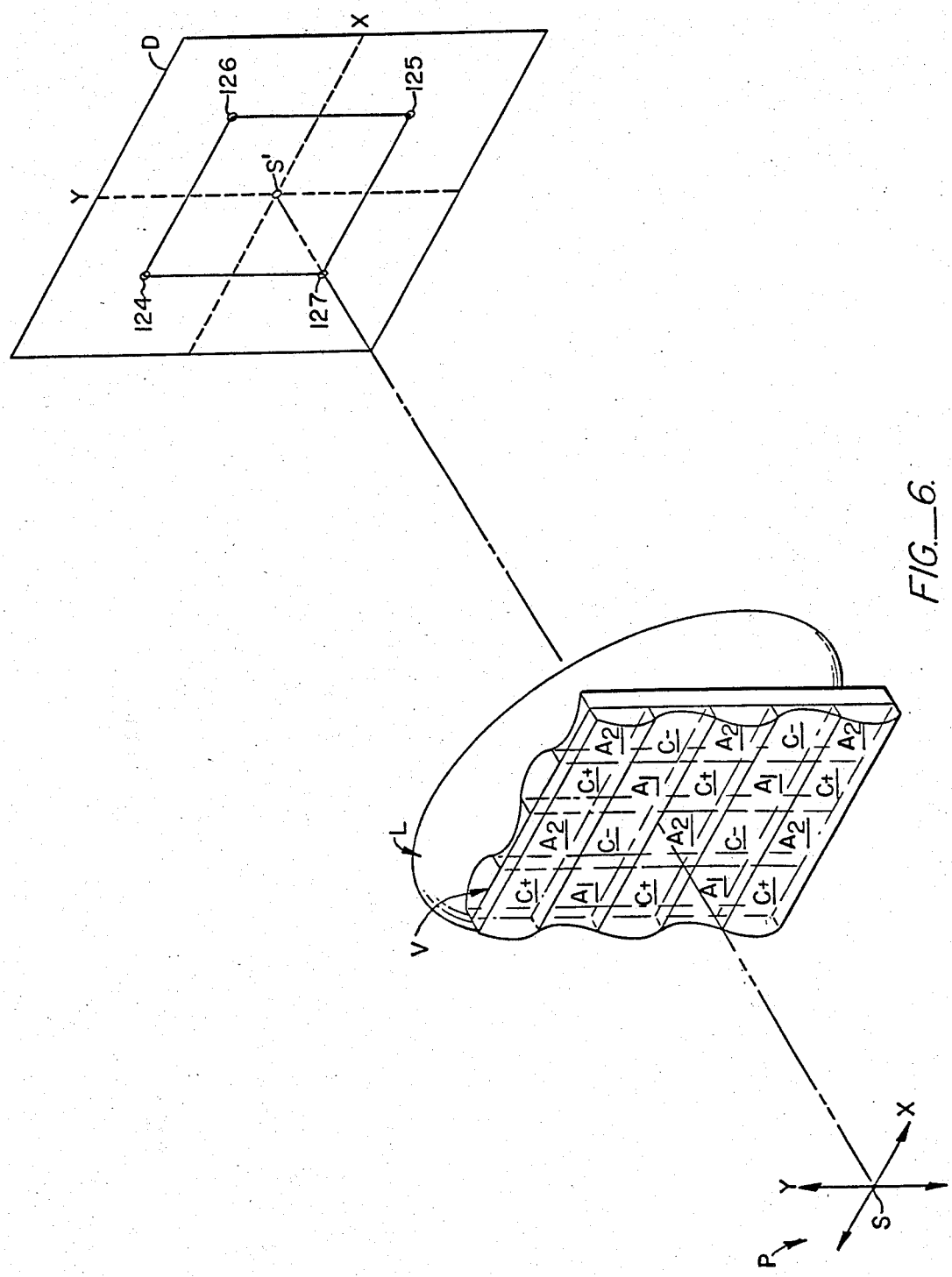
FIG._6.

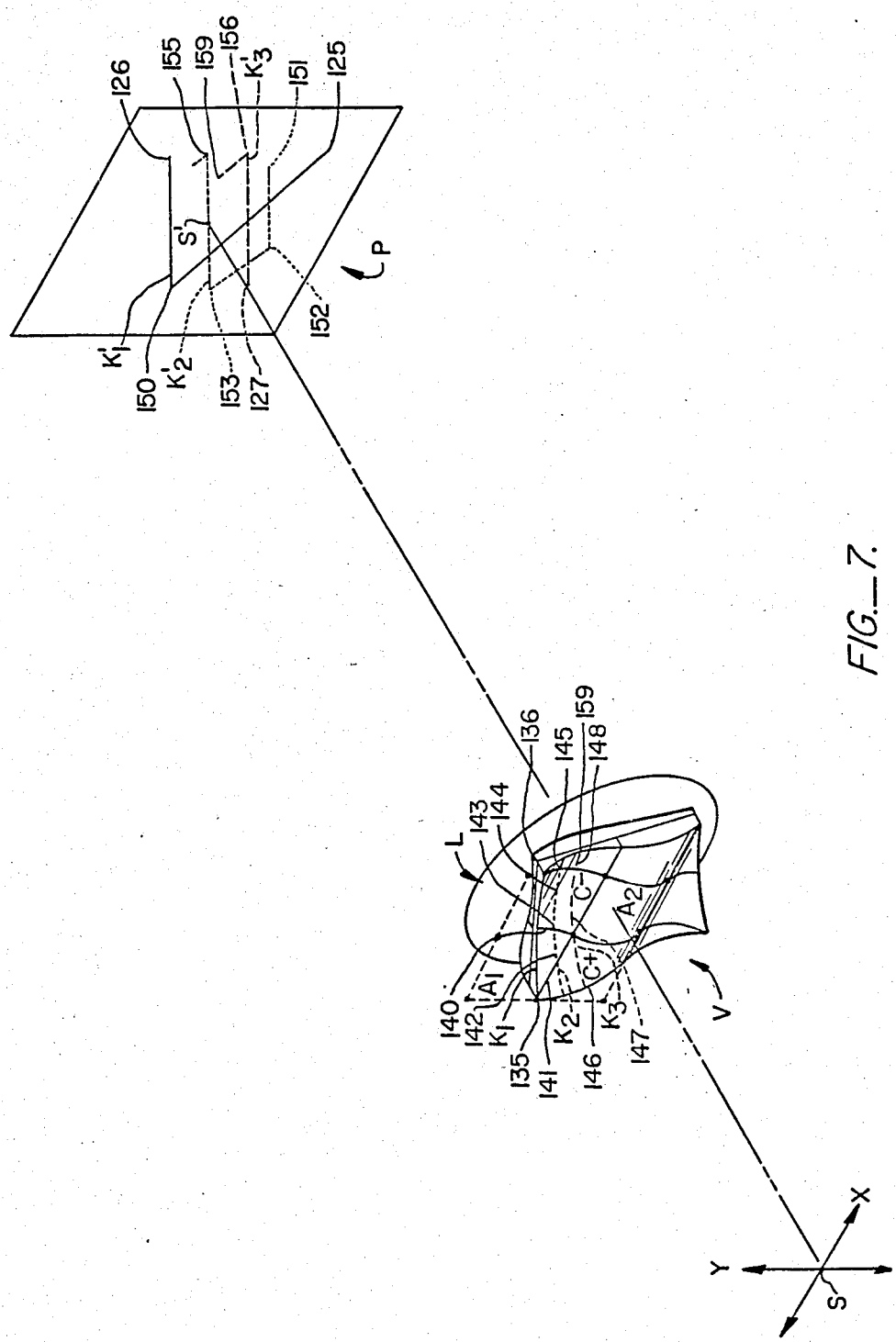
FIG._7.

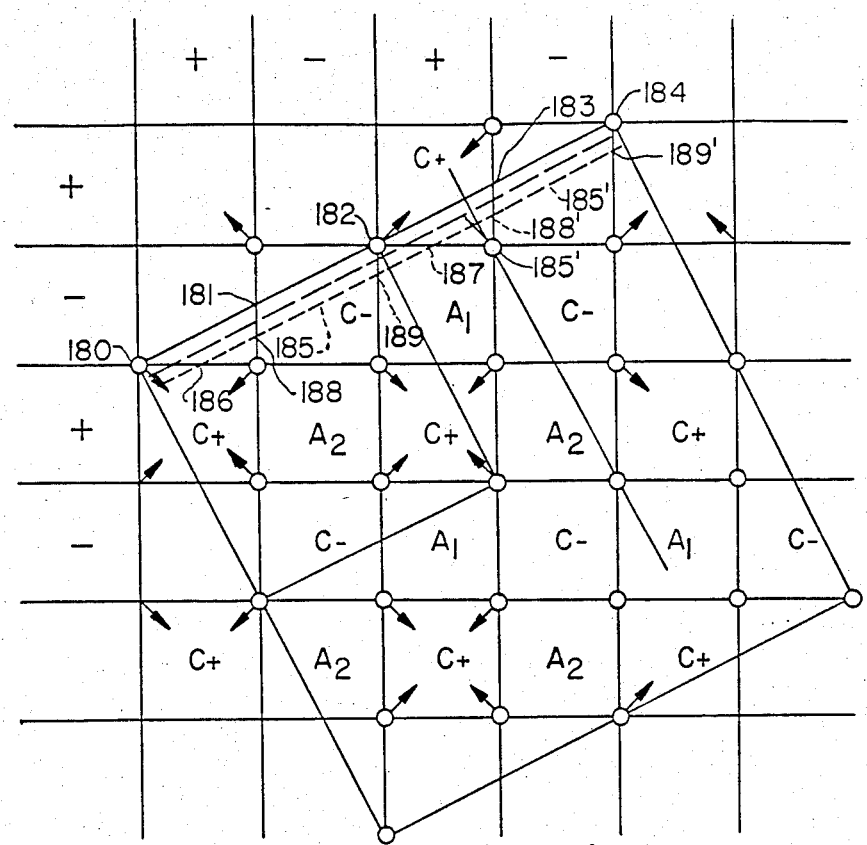
FIG._8A.
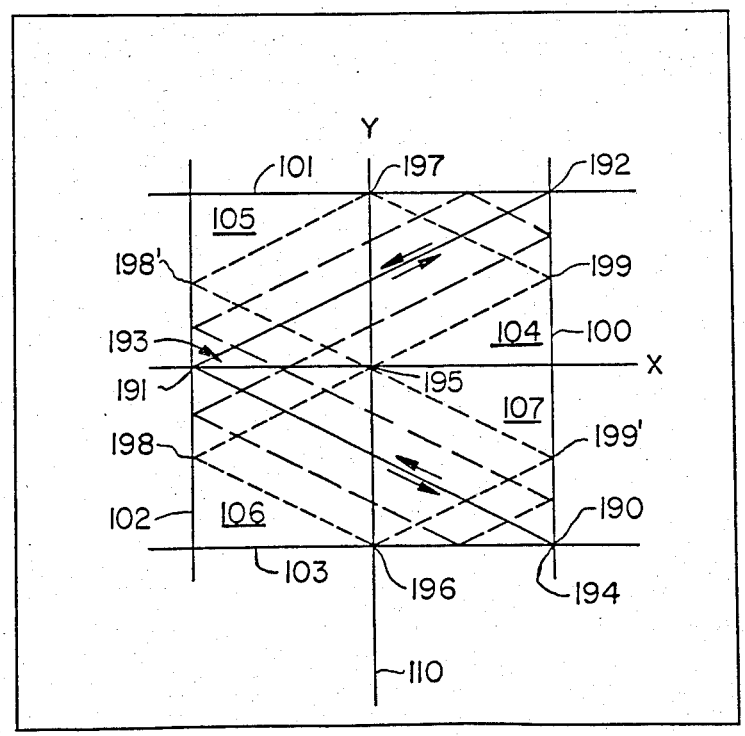
FIG._8B.

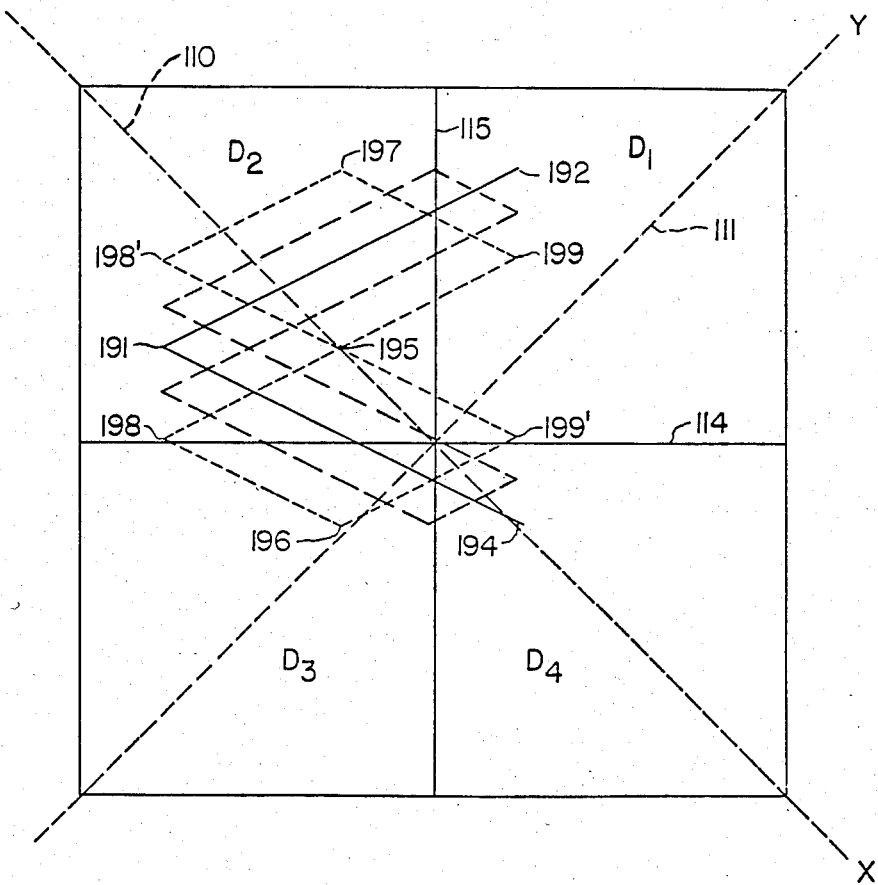
FIG._8C.

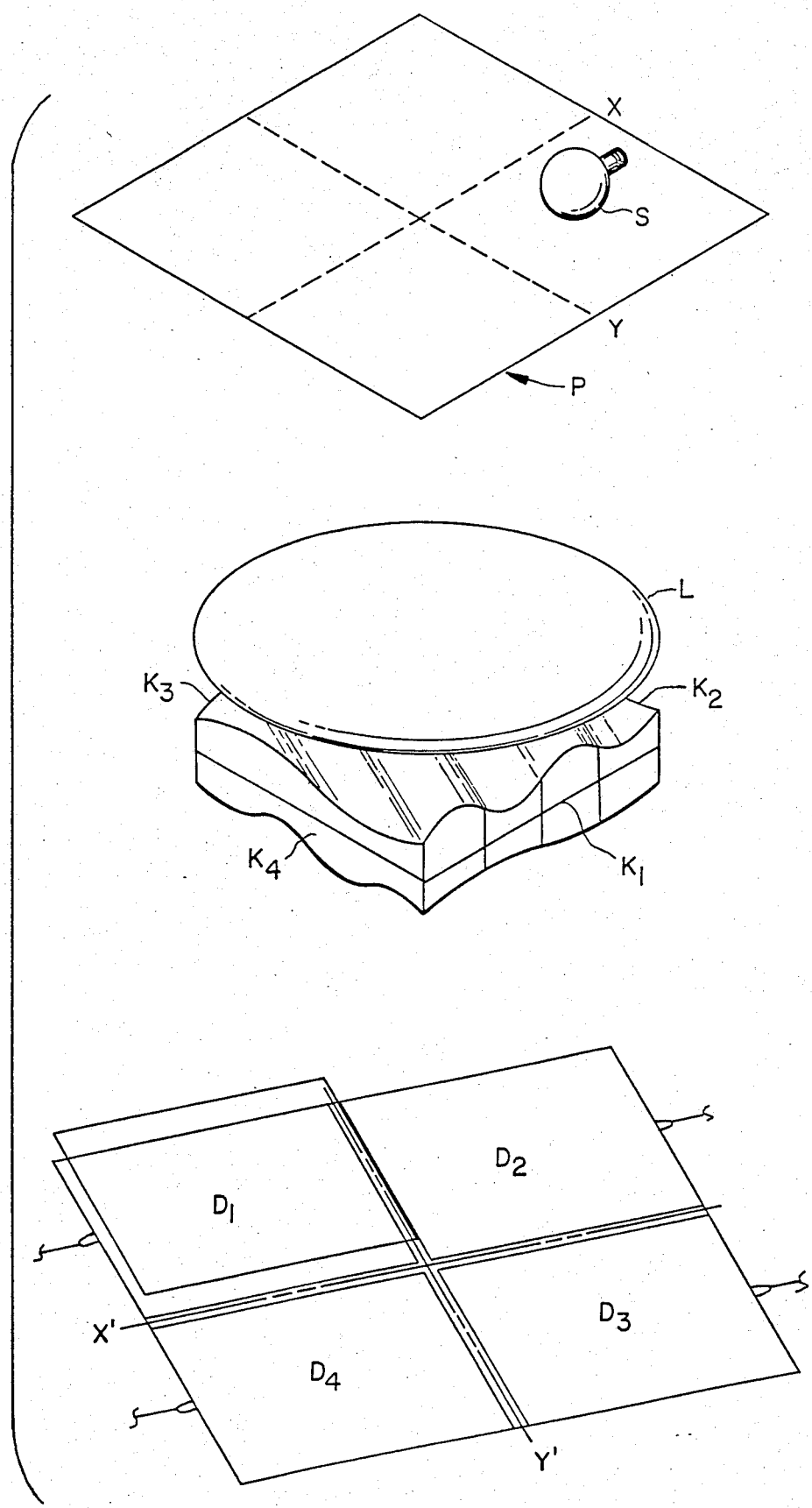
FIG._9.

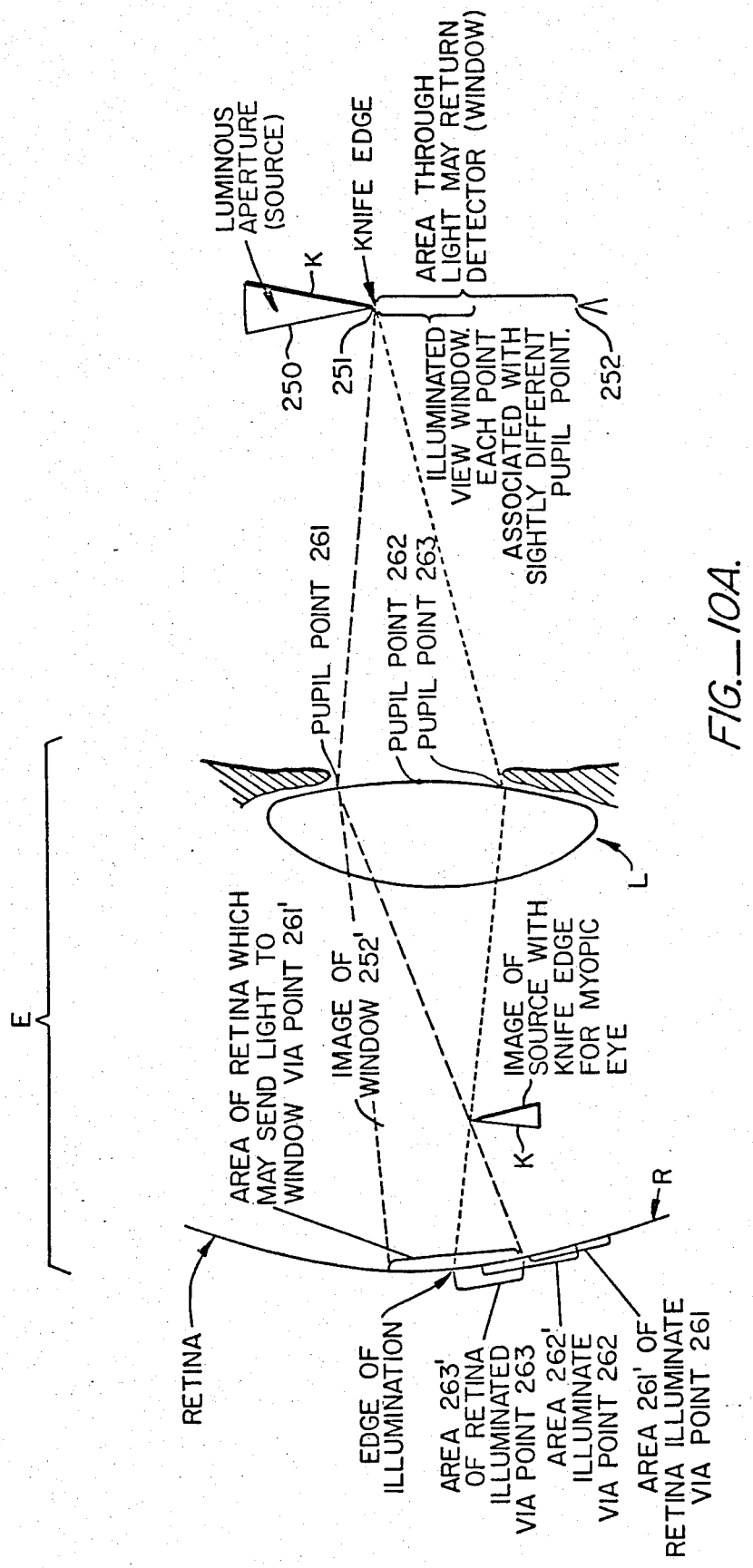
FIG._10A.

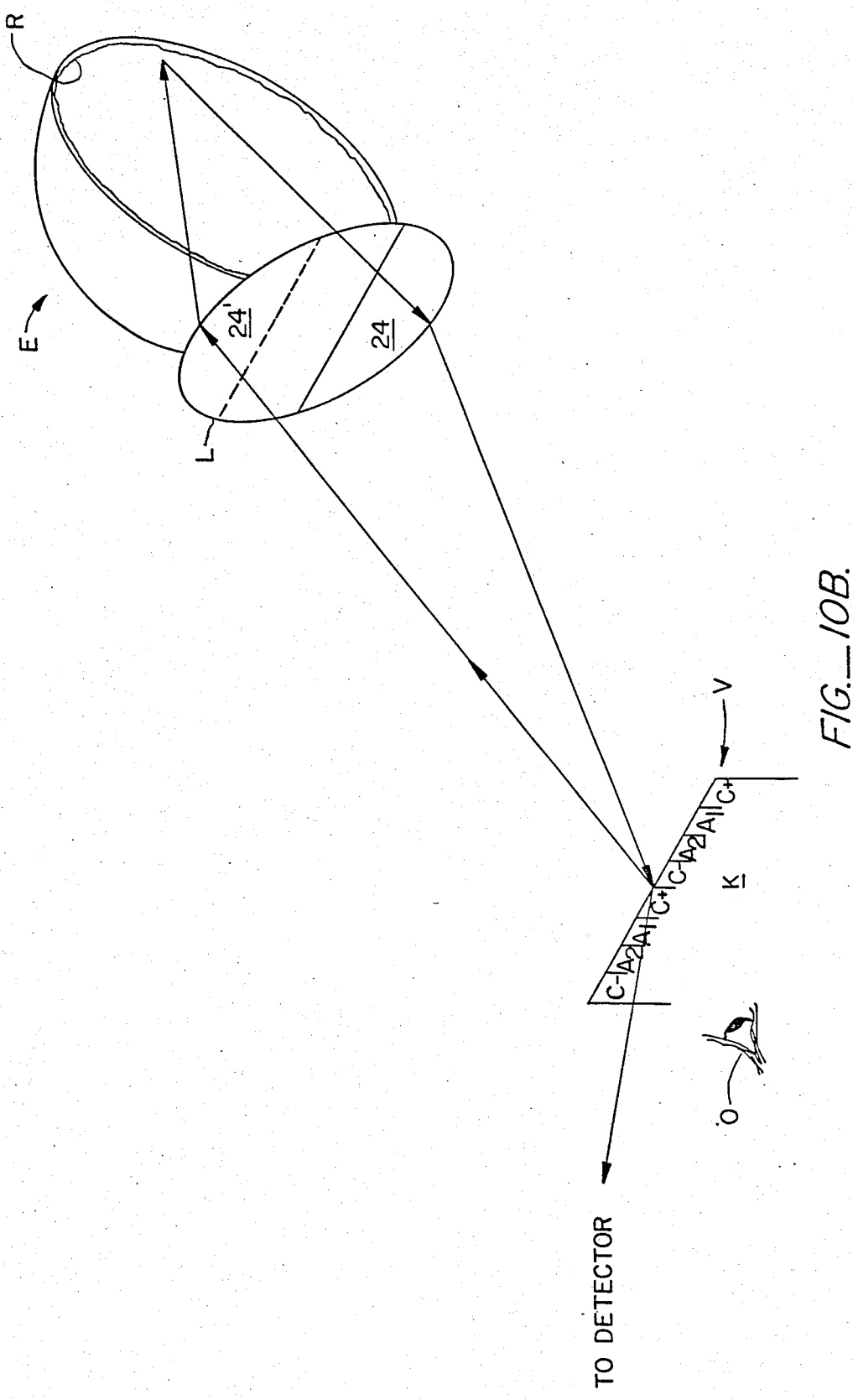
FIG._10B.

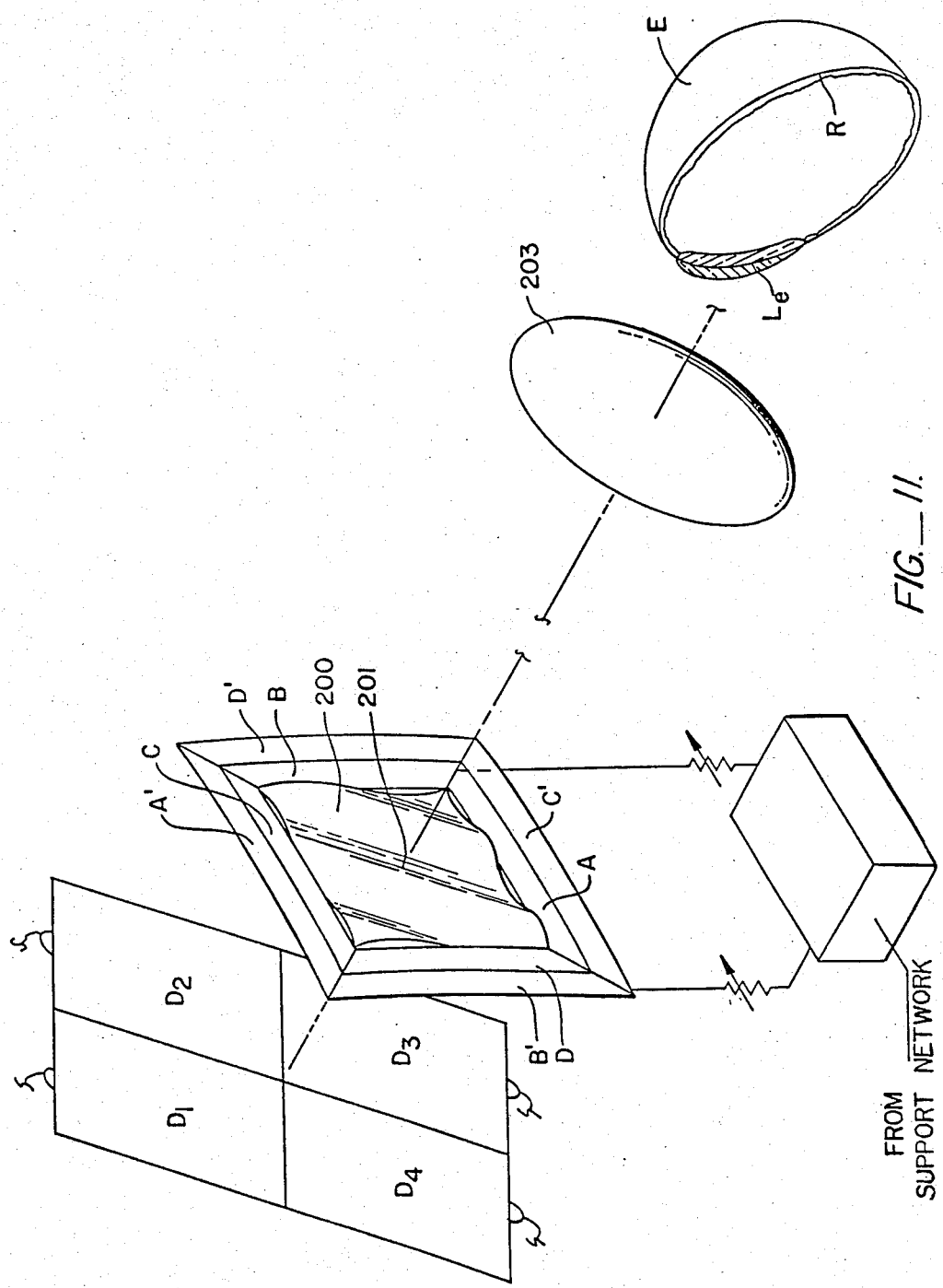
FIG._11.

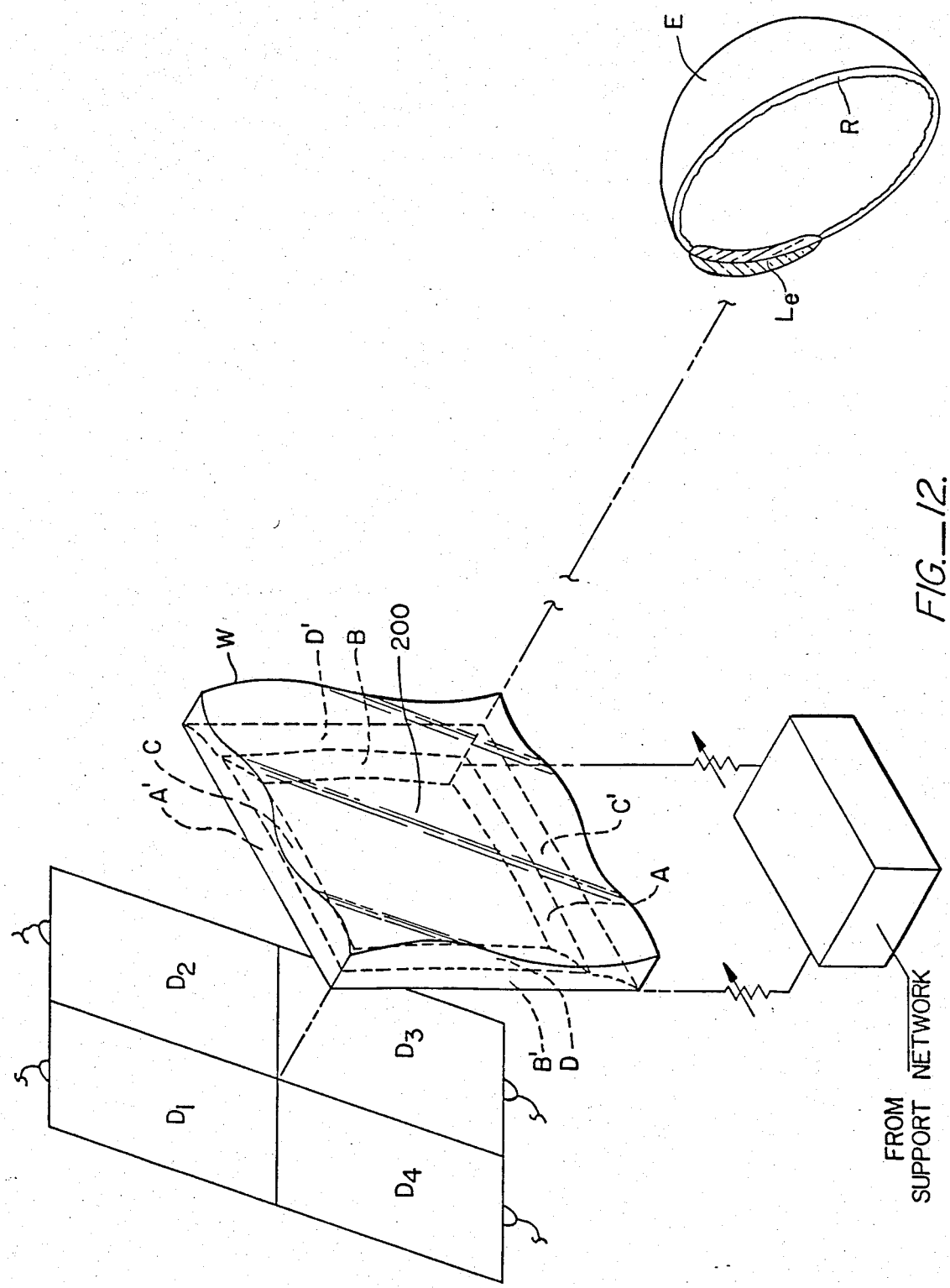
FIG._12.

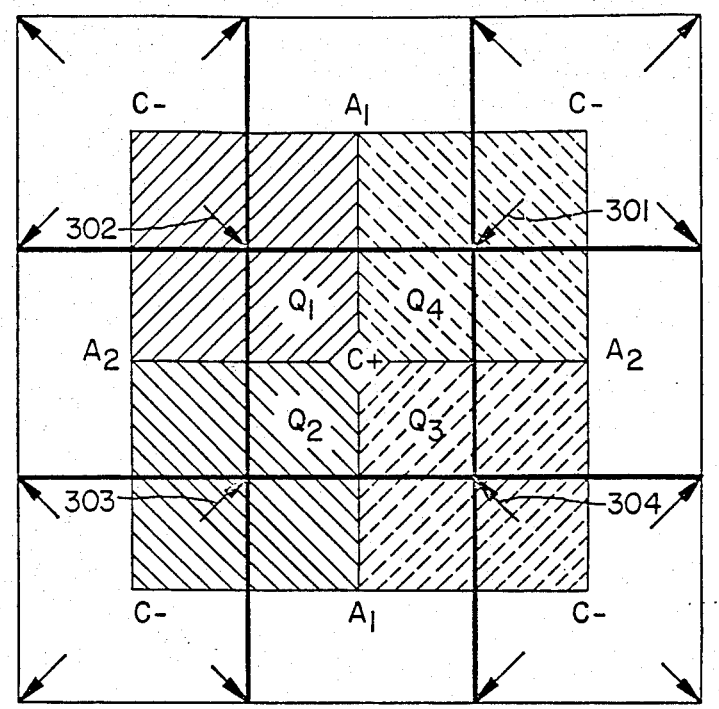
FIG._13A.
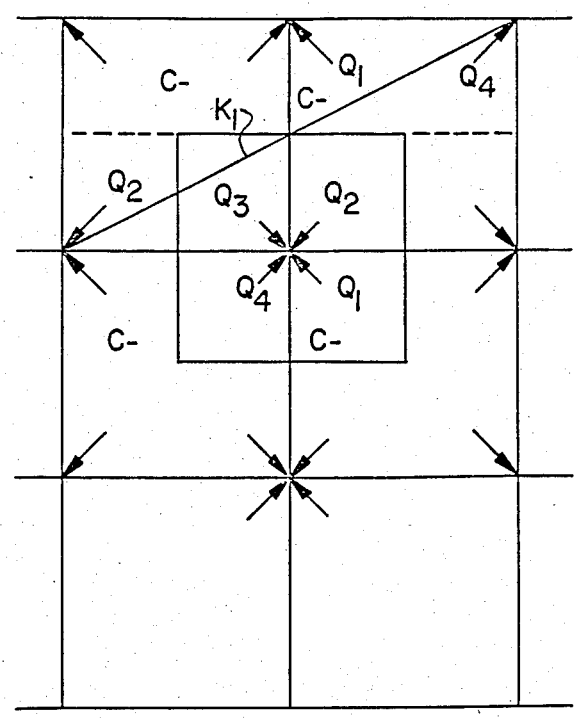
FIG._13B.
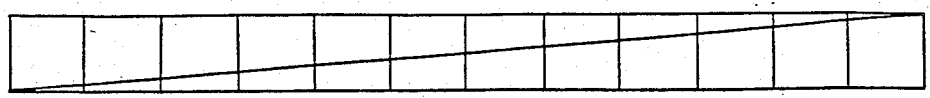
FIG._13C.

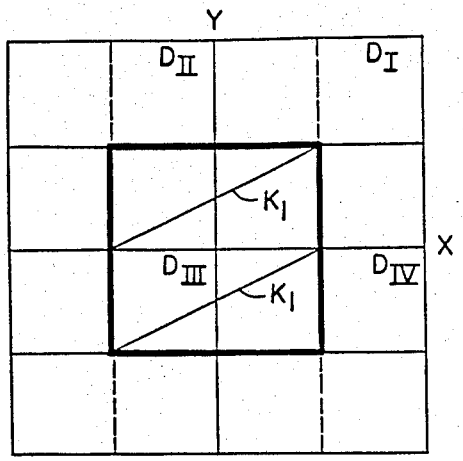 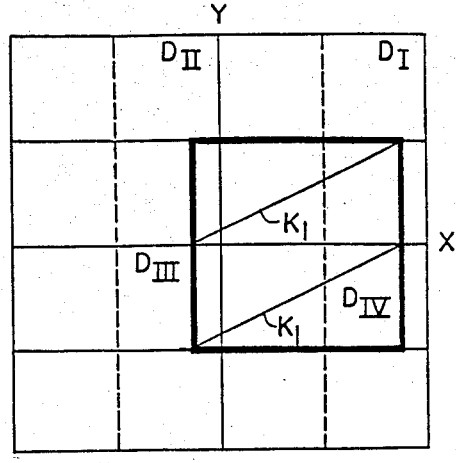
FIG._14A.  FIG._14B.
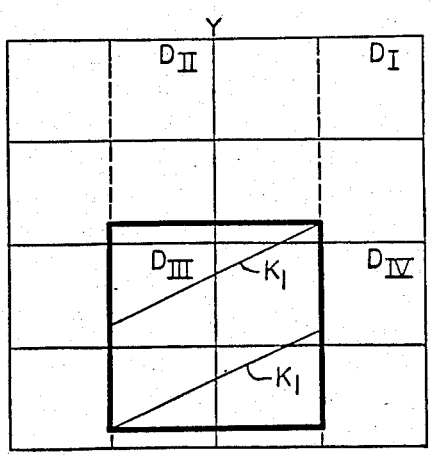 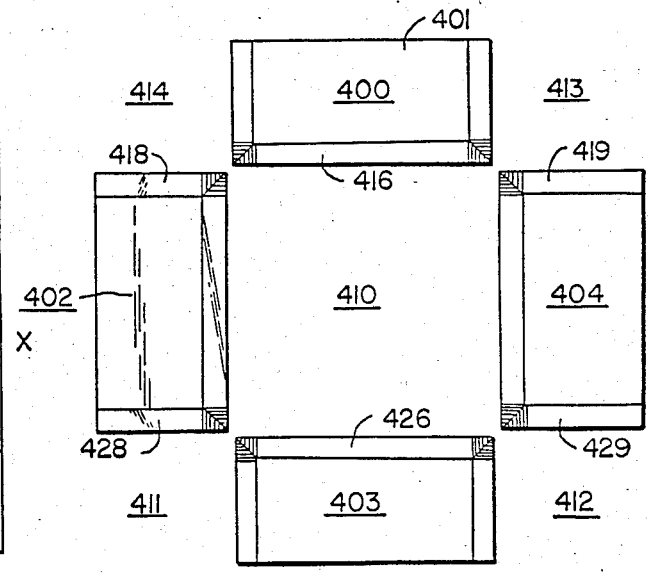
FIG._14C.  FIG._15B.

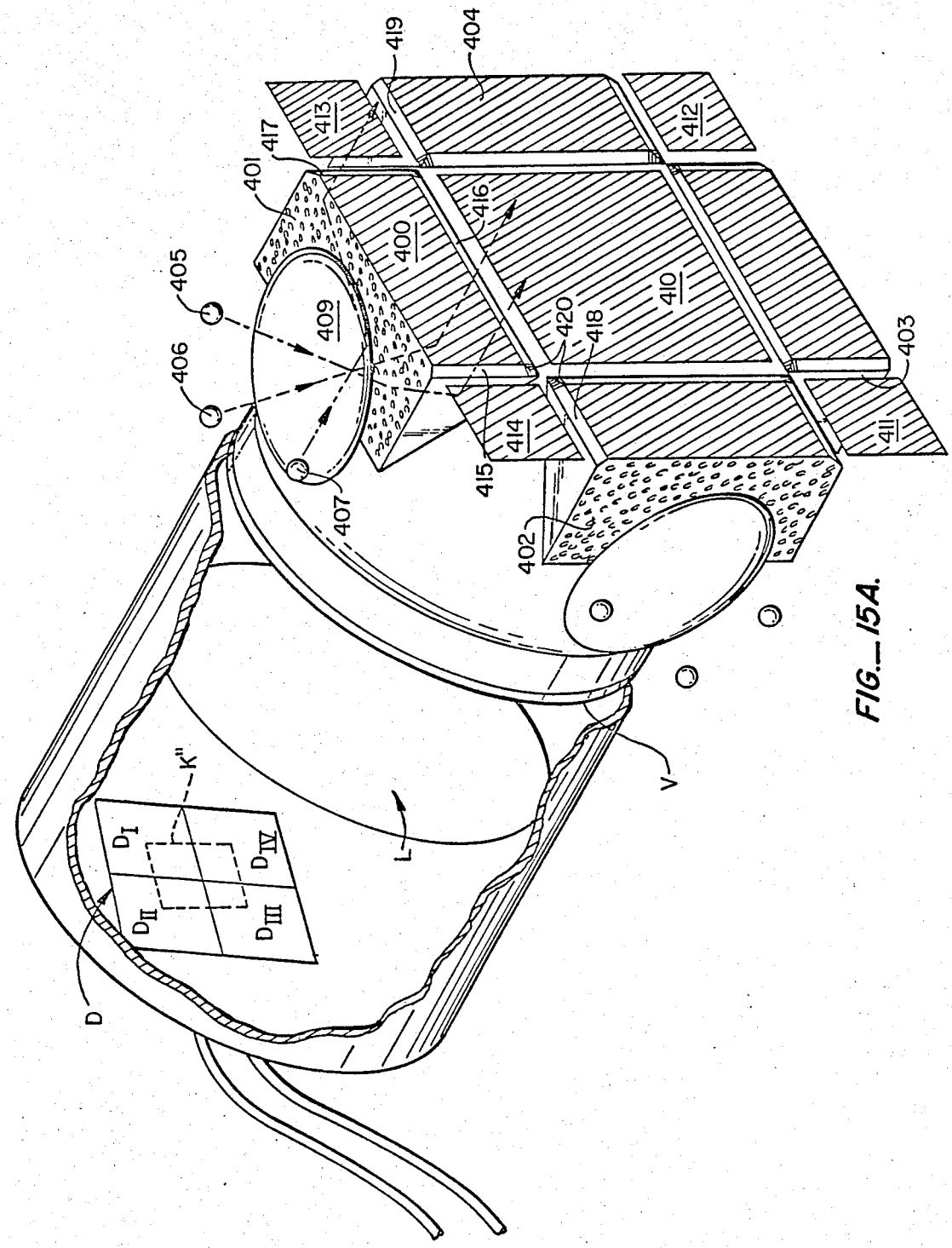
FIG._15A.

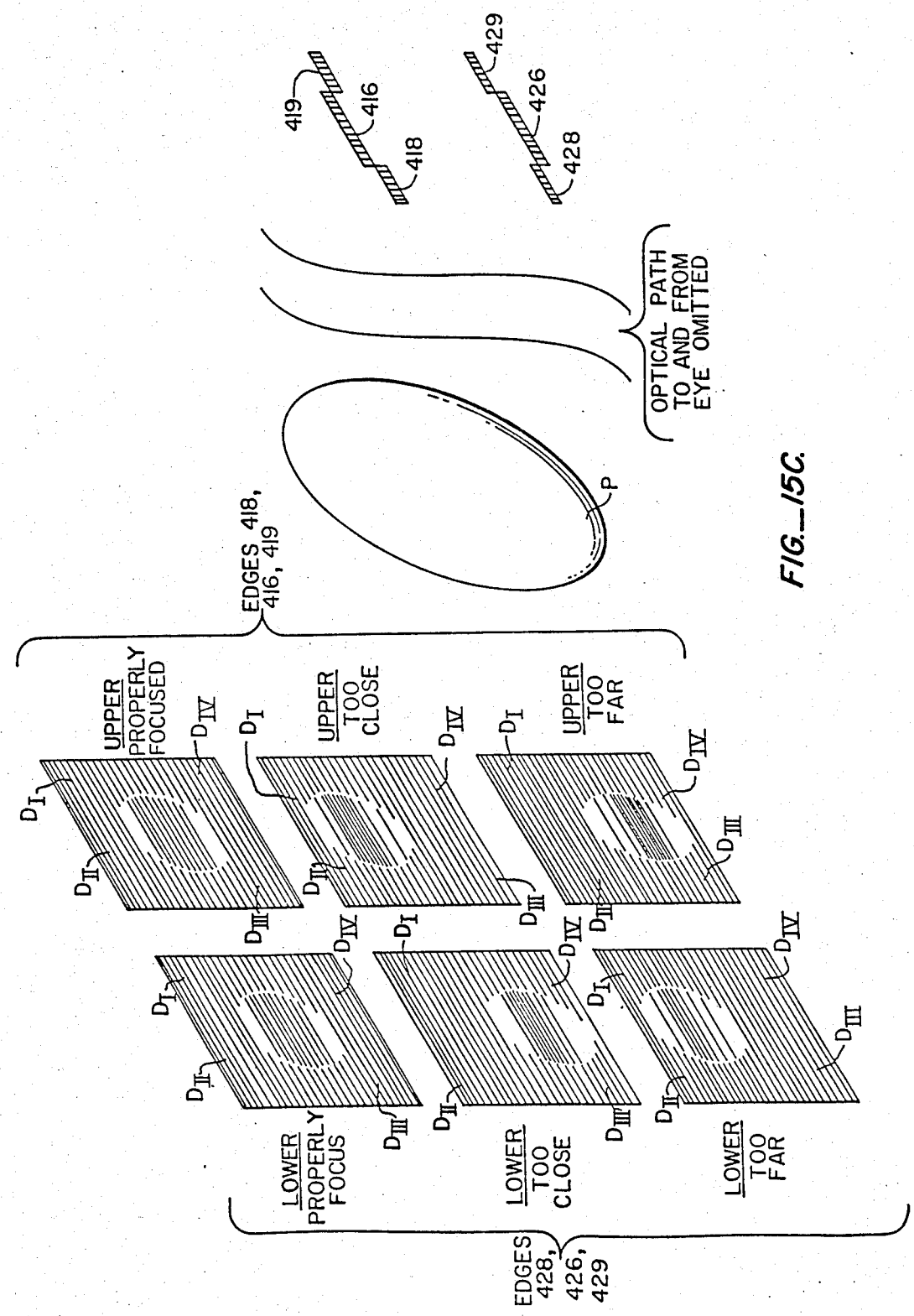
FIG._15C.

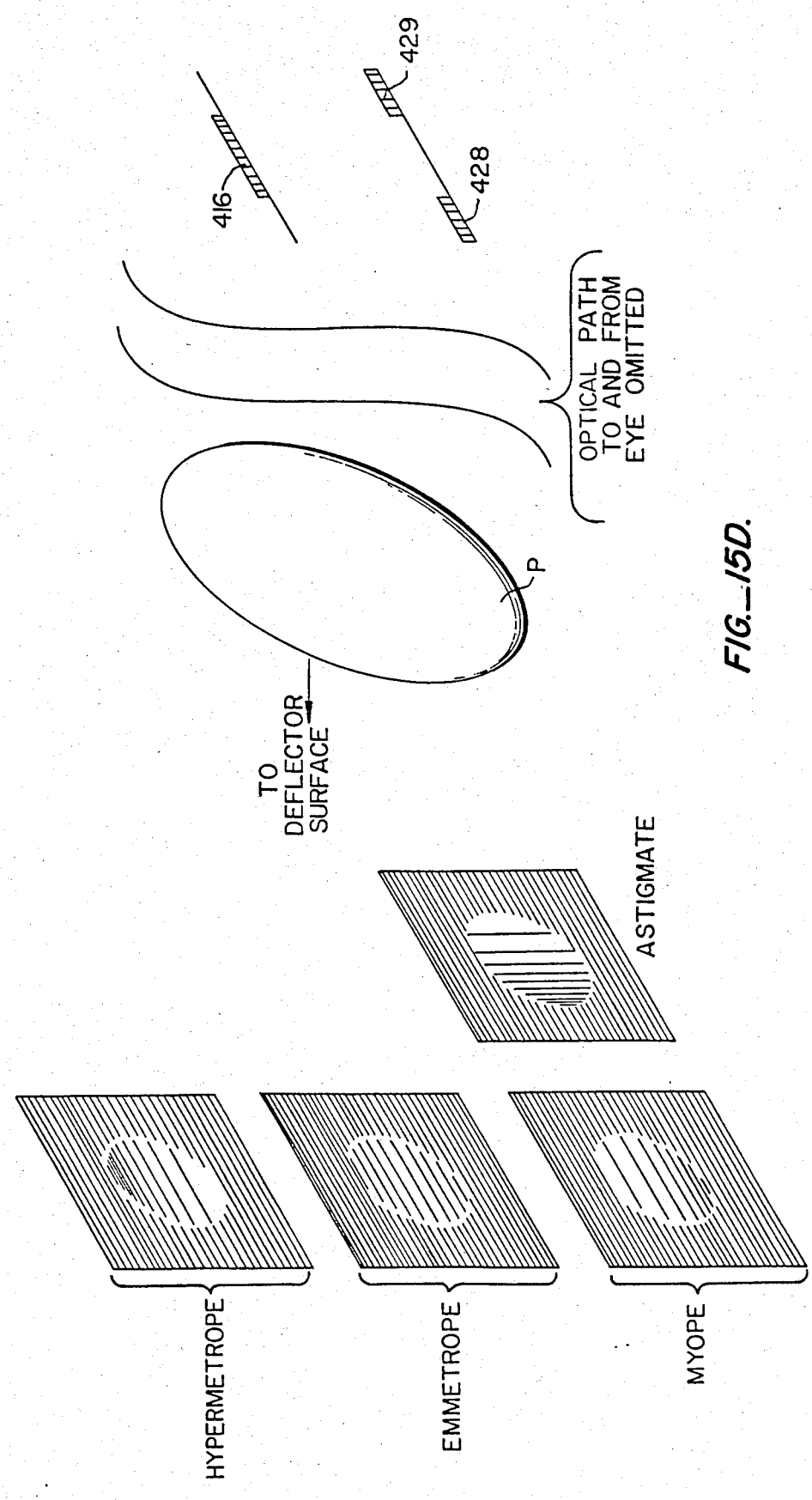
FIG.—15D.

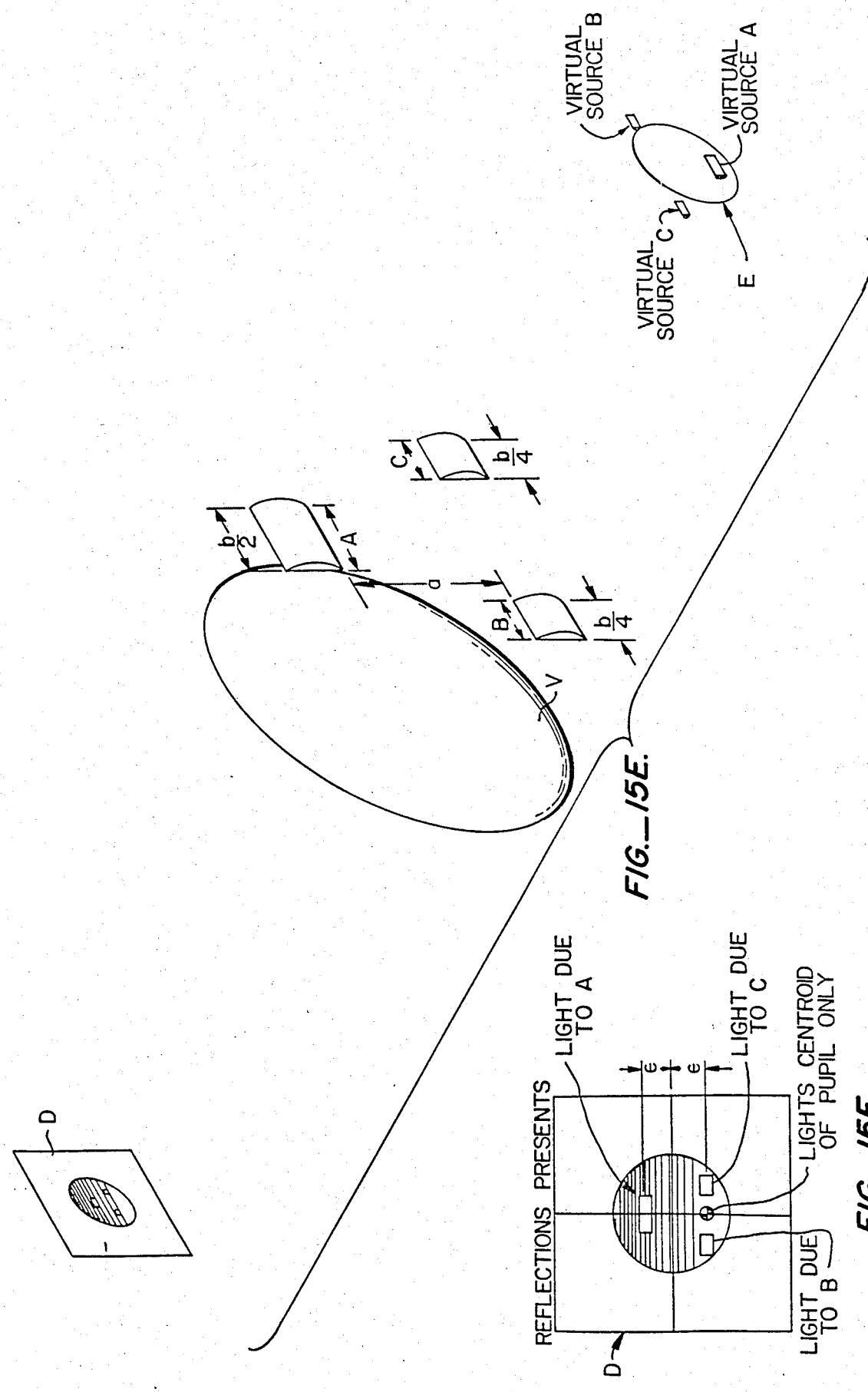
FIG._15E.
FIG._15F.

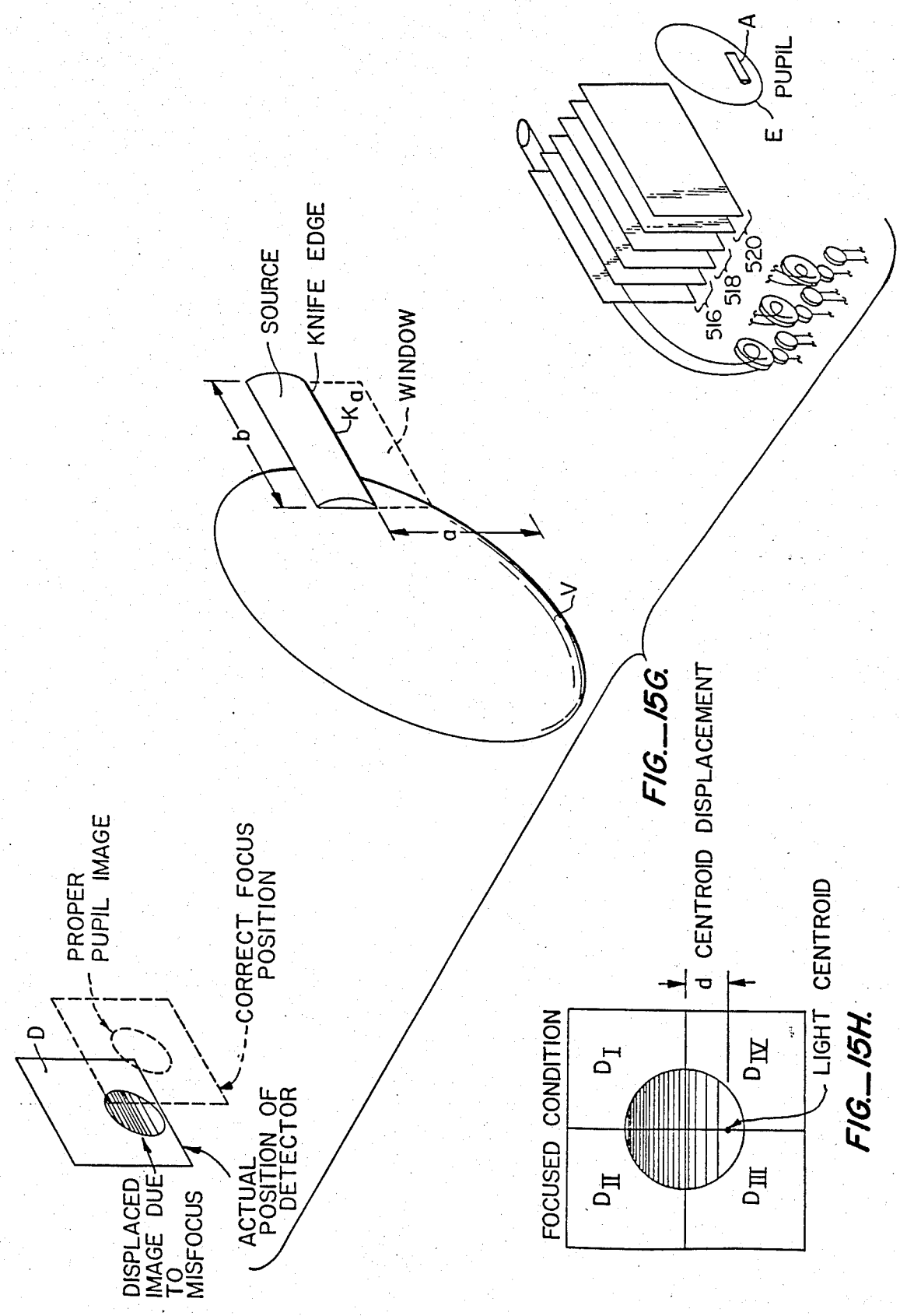
FIG._15G.
FIG._15H.

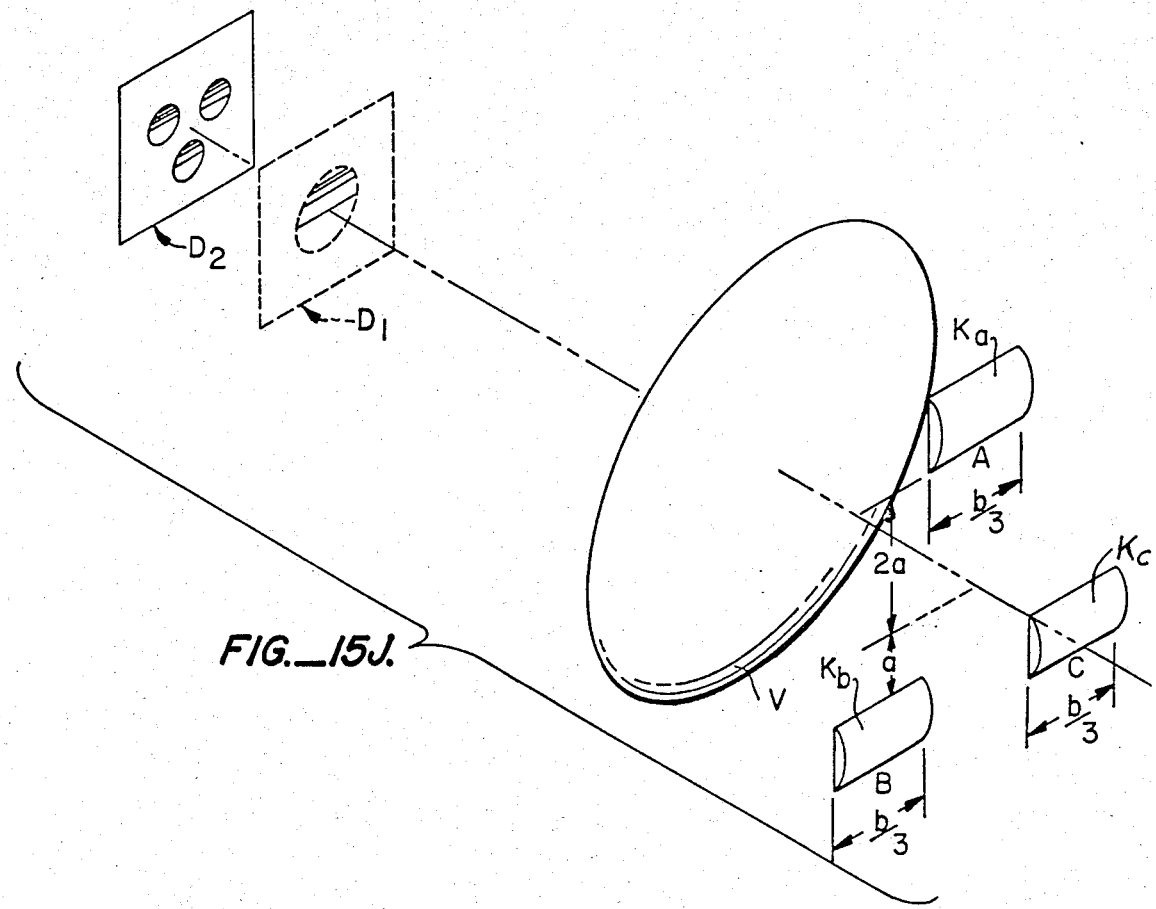
FIG._15J.
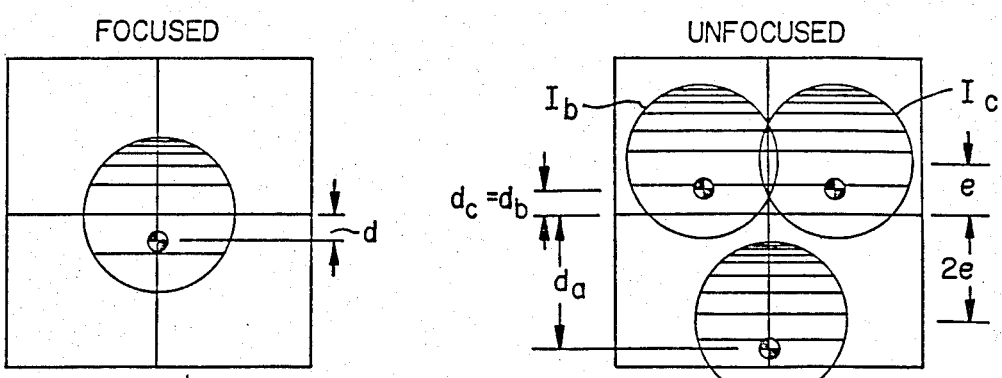
FOCUSED
FIG._15K.
UNFOCUSED
FIG._15L.

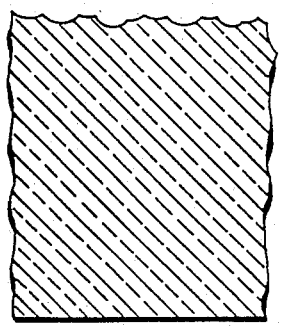
FIG._16A.
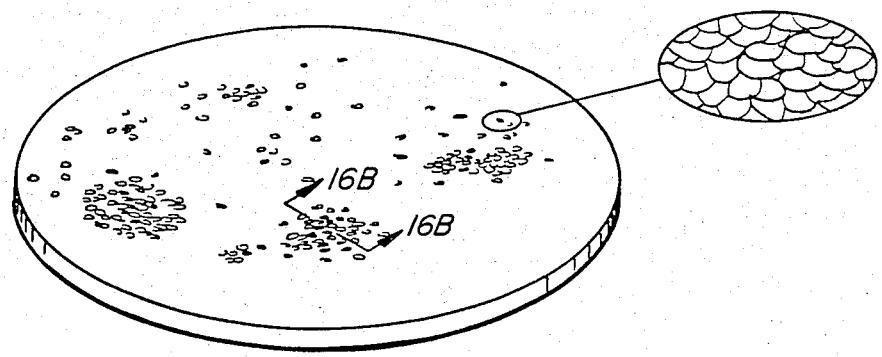
FIG._16B.

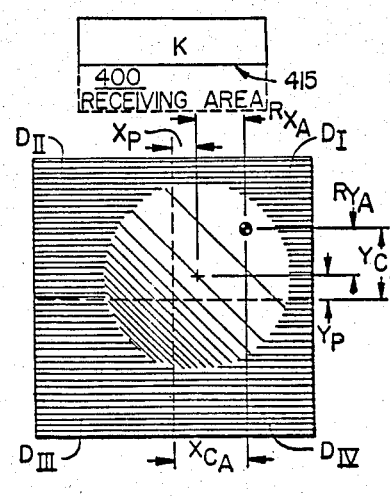
FIG._17A.
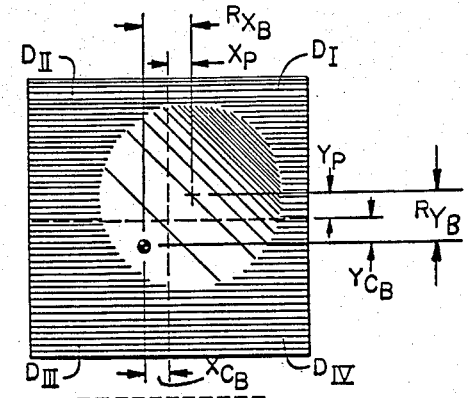
FIG._17B.
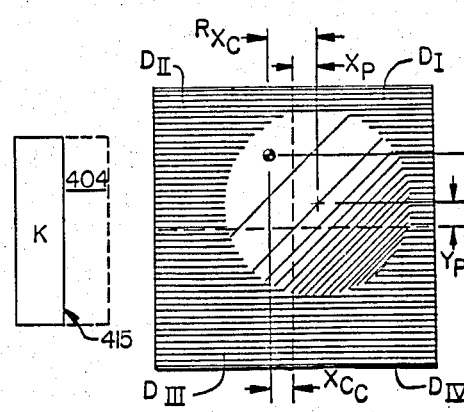
FIG._17C.
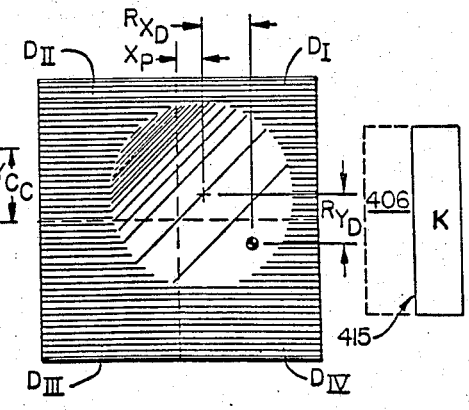
FIG._17D.

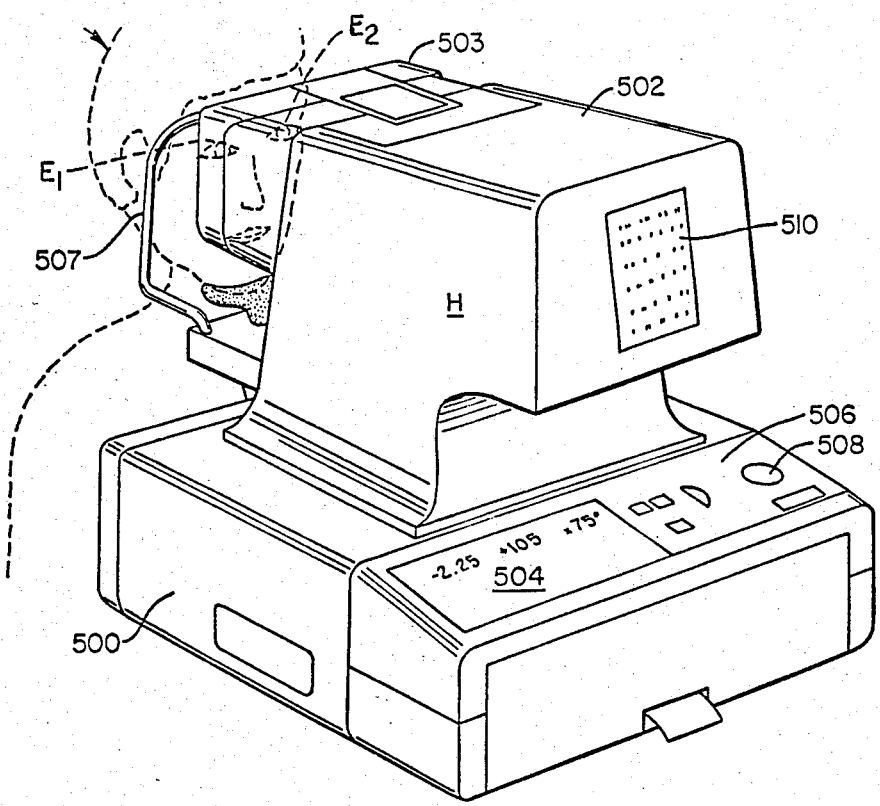
FIG._18.
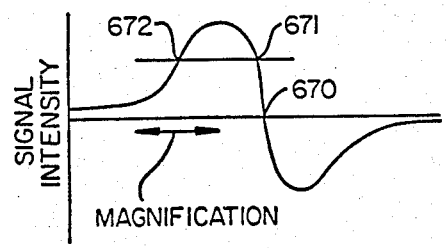
FIG._21.

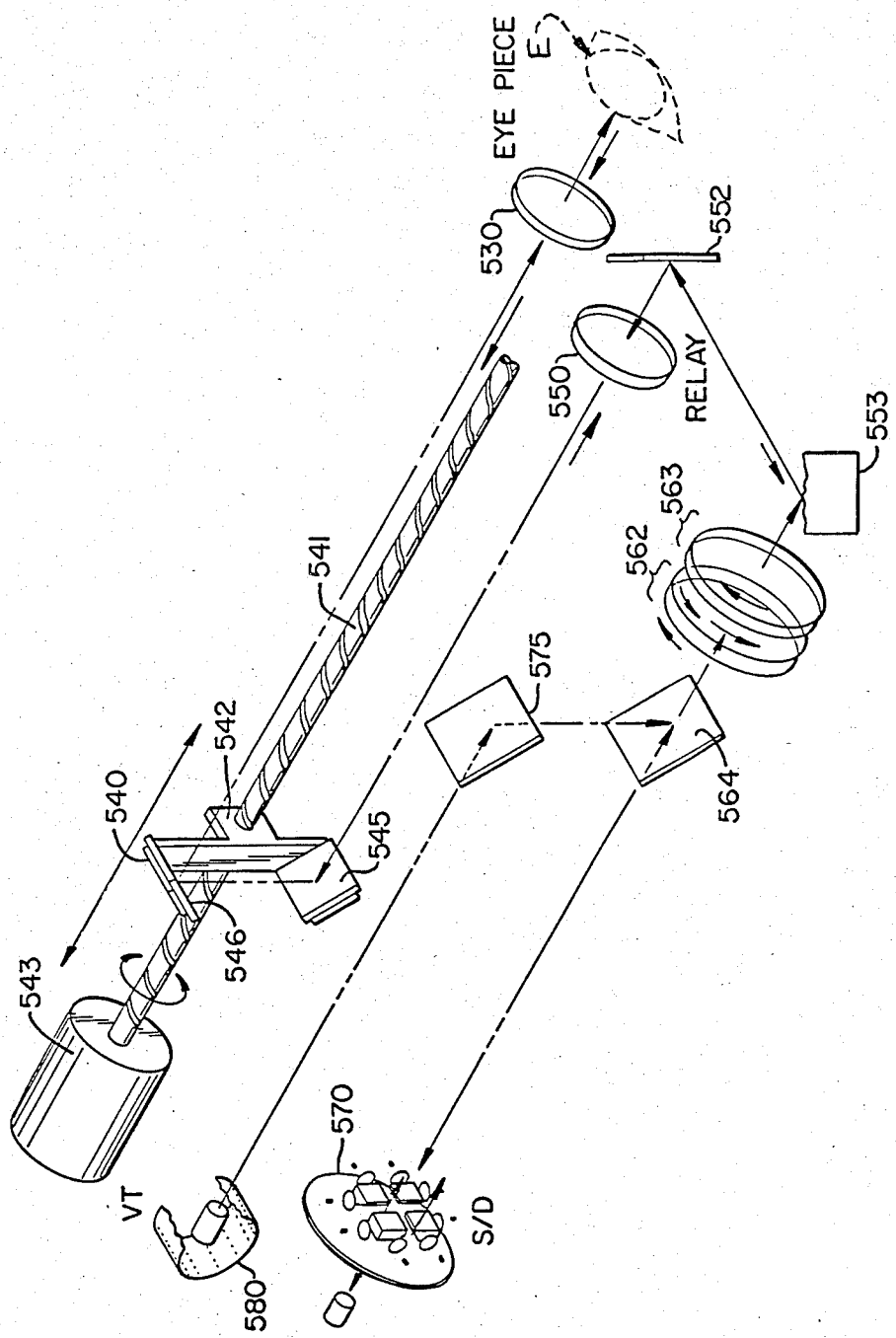
FIG._19.

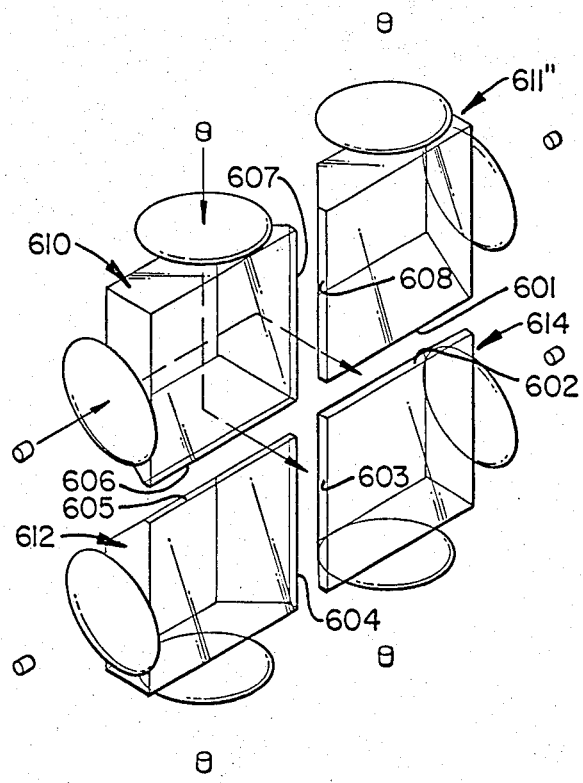
FIG._20.

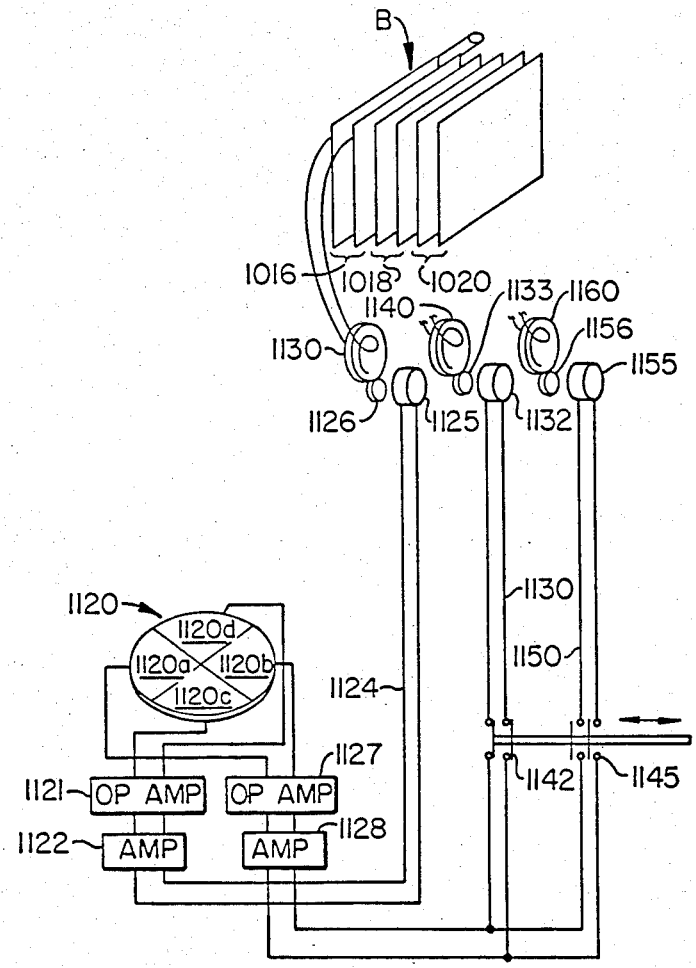
FIG.__22.

OBJECTIVE REFRACTOR FOR THE EYE

This invention relates to objective refractors. More particularly, this invention discloses an objective refractor utilizing knife-edge optics and remote image detection at necessarily low light levels.

This is a continuation-in-part patent application of U.S. patent application Ser. No. 202 536, now abandoned filed Oct. 31, 1980, by William E. Humphrey, entitled "Objective Refractor for the Eye."

SUMMARY OF THE PRIOR ART

Knife-edge optics have not heretofore been practically used with remote objective refractors. This is because the images produced by knife-edge optics in conjunction with the eye are of extremely low light levels. These low light level images are extremely difficult to remotely detect.

Low light level detectors are subject to noise. Specifically in detecting across a broad detection surface a difference of photosensitivity, the impedance or resistance between adjacent portions of the same photosensitive surface is low. Where the resistance is low, and the corresponding electron movement high, the signal-to-noise ratio quickly becomes destructive of the image difference trying to be sensed. There results a severe practical difficulty in trying to detect low light level images.

Objective refractors have heretofore been sensitive to the positioning of the eye. Precise positioning of the eye has been required before accurate objective refraction can be made. Automatic positioning has not been provided for, especially in a form where the positioning information is non-interactive, separate and distinct from the refractive information.

Moreover, prior art objective refractors have included sensitivity to the light level returned from the eye. Where, for example, a retina has a variation across its surface on light returned to the observer, heretofore variations in the prescriptive readings have occurred.

SUMMARY OF THE INVENTION

An objective refractor for the eye is disclosed in which knife-edge optics are utilized. The knife-edge optics cause characteristic illumination of the retina so that components of sphere and astigmatism can be identified. Provision for remote reading of the characteristic images is provided with the result that two orthogonally disposed knife-edge images can identify the sphere, cylinder and axis required for prescriptive patterns giving the direction and magnitude of required prescriptive change. A system of at least two orthogonally disposed, (and preferably four), knife edges with weighted lighting is disclosed for detection. Utilization of the knife-edge images is made possible by the detection of the low light level images at a detector having low noise level. A photo-sensitive element divided into a plurality of photo-discrete segments has light from the images proportionally dispersed over its surface. Such dispersion occurs through a matrix of wedge-shaped segments or alternately in the form of optical elements having cylindrical components. This dispersion of the light when used in combination with push-pull knife-edge patterns herein disclosed produces detectable low level refractive signal. An embodiment using an optic having a plurality of side by side optic elements, each element having the effect of crossed cylinders is disclosed with the detector. Separate independent and non-interactive positional information on one hand, and refractive information on the other hand is provided. Consequently the disclosed refractor is insensitive to adjustment and can accommodate a large range of pupil configuration with insensitivity to local retinal variations in light emission.

OBJECTS, FEATURES AND ADVANTAGES

Since the original filing of the first patent application, extensive development and experimentation has occurred. Applicant therefore has filed this application as a continuation-in-part updating as of the filing date of this application the preferred embodiment of the invention.

It is an object of this invention to disclose a knife-edge test with tell-tale illumination patterns on the retina of the human eye. According to this aspect of the invention, a light source with a knife-edge terminator projects collimated rays to the eye. Typically, a projection system is incorporated between the knife edge and the eye and is simultaneously used to project the resultant image from the eye to an image detector. The light patterns returned from the pupil of the eye have characteristic shape relative to the knife edge. Boundaries between light and dark portions of the pupil with components parallel to the knife edge indicate components of sphere and astigmatism. Boundaries with components normal to the knife edge indicate components of astigmatism along axes at an angle to the knife edge.

An advantage of utilizing knife-edge testing with respect to the human eye is that a tell-tale pattern of pupil illumination is present, which pattern indicates not only refractive error, but gives the sense and magnitude of correction required. Consequently, the output of the detector does not require hunting in order to determine optimal correction.

A further object of this invention is to disclose measurement of the human eye by objective refraction utilizing at least a light source, at least one knife edge, combined projection and reception optics and a photodetector. The source shines into the eye through an aperture formed such that at least a portion of the aperture boundary has a straight terminator, thereby acting as a knife edge barrier on the outgoing beam. The outgoing beam passes through the optics in a projecting capacity; images on the eye and thereafter is passed to the detector by the same optics acting in a reception capacity. A single knife edge can be used, and functions as a knife edge for light projected to and returning from the eye. Indeed any such boundary which is straight and knife edge like in character and which serves as an aperture edge for both outgoing and returning light simultaneously will do, providing that the side of the boundary which is clear for the outgoing beam is opaque for the returning beam and vice versa.

A further object of this invention is to disclose a sequence of edge illumination of preferably four knife edges for interrogation of the eye. These knife edges are preferably divided into opposing pairs. One pair of knife edges is illuminated from opposite directions parallel to a first axis; the other pair of knife edges is illuminated from opposite directions parallel to a second axis, this second axis being at right angles to the first axis. This opposing and opposite illumination of knife edges produces a "push-pull" effect in the resultant images. Image changes due to changing optical prescription in sphere, cylinder and axis can be segregated out from other image degradations, such as specular reflection from other portions of the eye as well as optical flare and the like from within the interrogating optical train. Additionally, reduced sensitivity to eye position is achieved.

An advantage of the disclosed push-pull knife edge interrogation of the eye is that two separate and non-interactive information bases are generated. The first is positional information. The second is refractive information. Each of these respective positional and refractive information bases are separate and non-interactive.

A further advantage of the disclosed detector is that accurate refractive measurements of the eye can be taken over a wide area. The instrument contains insensitivity to adjustment. Hence, accurate refraction can occur even though relatively substantial movement of the patient may take place during the measurement.

A further advantage of the disclosed detector is that it can accommodate a large range of pupil configurations. Moreover, pupil retinas having irregularities in their light transmission to the downstream detector can be measured. Such refractive measurement is insensitive to local retinal variations in the amount of light returned to the detector.

An advantage of this aspect of the invention is that a single detector can interrogate peripheral illuminating edges in sequence. By this sequential interrogation, the components of required optical correction can be identified sequentially in magnitude and sense.

An additional advantage is that the knife edges can each be separately provided with frequency coded light. Simultaneous interrogation of multiple knife edges can occur.

A further object of this invention is to disclose a preferred matrix of four knife edges for interrogating the eye. Knife edges are aligned in normally disposed pairs.

An advantage of the disclosed knife edge projection systems and light level detectors is that they can be incorporated in instruments of varying length. Moreover, and by using infrared illumination, the subject can view along a first path an illuminated target and be interrogated along the same path for perfection of the retinal image. A preferred embodiment of light-emitting diode interrogation in the infrared spectrum is disclosed.

An object of this invention is to disclose a preferred detector matrix for detecting low level light returning from an eye subject to knife edge testing. According to this aspect of the invention, the detector matrix is divided into four discrete quadrants. Each of these quadrants is photodistinct in that the photosensitive elements are electrically isolated one from another. By the expedient of delivering light to a photodistinct portion, a signal is emitted from the photodetector which has a low signal noise ratio.

A further object of this invention is to disclose in combination with a detector having photodistinct elements specialized optics for the distribution of light. According to this aspect of this invention, multi-element lenses are inserted between a low light level image in the pupil of the eye and the detector. When the low light level image is centrally located, light is equally distributed to all four detector quadrants. With a linear change of position of the centroid of the low level light image, a corresponding linear change of image intensity occurs on all detector quadrants. The detector emits a signal in proportion to the displacement of the centroid of the low light level image.

An advantage of this aspect of the invention is that the detector is particularly suited for detecting the center of low light level images such as those returned from knife edge testing of the eye. The optical center of a low light level image can be rapidly indicated. Corresponding corrections can be applied to the eye to determine objectively the refractive correction required.

Yet another object of this invention is to disclose a mode of measuring at the detector segments the returned low level light images. According to this aspect of the invention, a summing process is disclosed in which the image on a pair of quadrants is summed and differentiated with respect to the image on a remaining pair of quadrants. By the expedient of striking a ratio of the image intensity differences relative to the light received on all quadrants, an image signal is received which is proportional to the displacement of low light level images projected.

Yet another object of this invention is to disclose lens configurations for utilization with low level light detection aspects of this invention. According to a first embodiment, the resultant knife-edge image is relayed to a matrix of deflecting optical wedges or prisms. This matrix of deflecting prisms varies in deflecting intensity as displacement is varied from a neutral position.

A further object of this invention is to disclose a class of image dispersing optics, which optics may be utilized for the displacement of light with optical detectors preferably of the discrete photoquadrant variety. According to this aspect of the invention, an optic matrix is generated having an overall optical effect that may best be described using lens optics of the cross cylinder variety. A first group of cylinders (of either positive or negative power) are laid in a first direction to in effect generate a first light deflective effect. A second group of cylinders are laid in another direction (preferably at right angles) and disposed to generate a second light deflective effect. The cylinders used may be chosen from pairings which are positive and positive, negative and negative, or positive and negative (regardless of order). There results an overall matrix of optical elements, which matrix of optical elements causes distribution of light to each of the quadrants of photodiscrete detectors.

An advantage of the disclosed lens elements for utilization with photodiscrete detectors is that the greater the number of discrete elements, the less critical the alignment of the lens elements with respect to a knife edge becomes. For example, where a large number of randomly placed elements is used, the need for precise alignment of knife edges with respect to the elements disappears altogether.

Yet another object of this invention is to disclose other configurations of lens elements that will serve to distribute light among photodiscrete detector segments in proportion to the displacement of low intensity images. By way of example, conical and randomly aligned prismatic segments all have an effect which can be used with the photodiscrete detectors herein disclosed.

An additional and preferred embodiment of this invention includes a matrix generated by cylindrical lenses of positive and negative power. These cylinders are laid in side-by-side disposition. Along one side of the lens positive and negative cylinders are aligned in a side-by-side array. Along the opposite side of the lens positive and negative cylinders are aligned in a side-byside array at preferred right angles to the first array. There results a matrix of crossed cylinder lenses, including positive sphere, negative sphere, cylinder in a first orientation and cylinder in a second and 90° rotated direction. This specialized lens has the advantage of dispersing light evenly in a pattern not unlike that generated by the trace of various Lissajous figures.

An advantage of this lens is that when it is combined with a knife edge cutting across the lens matrix, the knife edge at the boundary can generate symmetric patterns for detection. These patterns evenly distribute light over a given area, which distributed light may then be detected to photodiscrete detecting elements.

An advantage of the knife edges utilized with the matrix of cylindrical lenses is that the electrical signal out from the detector is directly proportional to the intensity of the image and the image displacement. Moreover, extremely low light levels can be sensed. Segments of the photosensitive surface can all be electrically isolated one from another.

An advantage of the cylindrical embodiment is that the overall projection system required for the detection of light is shortened. Consequently, this projection system lends itself to compactness in the disclosed detector.

A further object of this invention is to disclose a preferred embodiment of the lens elements in front of a four quadrant detector. According to this aspect of the invention, negative lens surfaces are distributed in side-by-side random relationship over an optical surface, preferably a refractive surface. Specifically, these surfaces are of random alignment and closely spaced. An easily constructed lens element results.

An advantage of this aspect of the invention is that the optical surface can be easily constructed. For example, it has been found that by utilizing a positive mold, such as a ballbearing impressed upon an optical surface or replicating media for an optical surface, one obtains a perfectly satisfactory optical element.

A further advantage of this invention is that the disclosed randomly made optical surface or "pebble plate" does away with the need for precisely aligning the knife edge with respect to an axis of the plate. Instead, both the pebble plate and the optic elements utilized with it can be randomly placed one with respect to another.

A further object of this invention is to disclose a preferred embodiment of the matrix of cylindrical lenses in combination with a knife edge. Light from the knife edge is projected through the specialized optics to the eye and light received from the eye passes again through adjacent portions of the specialized cylindrical lens. There results in the passage of light to the eye a Lissajous-like dispersement of light along the knife edge. Consequently, only a portion of the light so projected can be seen over the knife edge. The remaining portions of the light projected to the eye from the knife edge are not returnable to the detectors as the physics of the knife edge test renders these rays not visible. The portion seen over the knife edge images back to a position immediately above the segment of the cylindrical matrix from which projection originally occurred. At this segment of the lens a complimentary deflection of the light occurs. There results an enhanced displacement of the light.

An advantage of this aspect of the invention is that the physics of a knife-edge test is used in combination with the predictable dispersion of light at the knife edge to screen out all that light, save and except that which has a desired projection angle which can be seen upon return. There results a low level light signal of enhanced sensitivity returning from the eye.

A further advantage of this invention is that the returning light hits a segment of the cylindrical matrix lenses, which segment produces a complimentary defection. This complimentary deflection not only further deflects the light, but produces an image center of gravity which is an enhanced, and improved signal.

A further object of this invention is to disclose a flare control illumination pattern. According to this aspect of the invention, the projected light is weighted in intensity about the center of the detector. Preferably, two light sources are projected on opposite sides of the knife edges being utilized. One area is remote from the knife edge, the other area is adjacent the knife edge. Specularly reflected images are a function of the illumination of both areas and are symmetrical or cancelling in their effect. These specular reflections form a uniform background to the detector which can be ignored. The remaining image changes are solely a function of the knife edge, which knife-edge images can be utilized to determine the sense of required correction.

A further object of this invention is to disclose a knife edge and aperture combination for a detector utilizing the invention set forth herein. According to this aspect of the invention, a detector with five apertures is disclosed. The detector includes a central aperture having a dimension of approximately two units by two units. Four peripheral apertures are placed for the sensing of light with each aperture being on a one by one basis. Knife edges are aligned to each aperture. The central aperture includes four inwardly mounted knife edges about the periphery of the two by two central aperture. The peripheral one by one apertures include paired knife edges. These knife edges are each aligned parallel to a knife edge of the central aperture and faced in an opposite direction.

An advantage of this aspect of the invention is that all the light sources in the detector head are active. No light sources are located merely for the emitting of light, which light is not utilized in a knife edge testing.

A further advantage of the detector head is that it is particularly adapted to use in opposing detecting configurations. For example, the detector head can be utilized for examination of the produced images on a push-pull basis.

A further advantage of the knife edge configuration of this invention is that the eye positional information and the eye refractive information are separate and non-interactive.

A further object of this invention is to disclose an apparatus and method for locating an eye first for tests. This apparatus and process utilizes the specialized detector head immediately described above. First, knife edges are illuminated along co-linear borders of the central aperture and the two peripheral apertures. The single knife edge of the central apertures faces in a first direction and is generally of two units of length. The paired knife edges of the peripheral aperture face in the opposite direction and are each one unit of length. All knife edges are examined together. The central two unit length of knife edge illuminates the eye on one side of an axis. The paired and peripheral portions of the knife edge illuminates the eye on the opposite side of the same axis. Since the eye is illuminated from both sides of the optical axes sensitivity to refractive error is eliminated. However, by using parallel spaced apart co-linear borders, both positioning of the optical axis to the eye and proper distancing of the eye can occur. There results a detector which is particularly sensitive to the placement of the eye in front of it.

An advantage of the disclosed sequence for positioning the eye is that prescriptive refractive effects are cancelled. As each of the knife edges are opposed and of equal length, the resultant projection of light is not sensitive to the particular refractive error possessed by the eye. Instead, the detectors evenly illuminate all classes of eyes and permit these eyes to be centered both transversely and towards and away from the detector.

A further object of this invention is to disclose a particularly suitable knife edge combination, which combination is sensitive to prescriptive errors and insensitive to the positioning of the eye. According to this aspect of the invention, portions of the apertures are illuminated at their knife edges. Typically, a knife edge faced along the central aperture is illuminated. Corresponding knife edges on the peripheral apertures are illuminated. The corresponding knife edges face in the same direction, are parallel, but are separated by the width of the central aperture. There results a knife edge alignment all in the same direction.

An advantage of this aspect of the invention is that prescriptive refractive effects only are picked up; effects due to the positioning of the eye are in large measure ignored.

Yet a further object of this invention is to disclose a sequence of examination of the eye. According to this aspect of the invention, the eye is first positioned utilizing knife edges illuminated in opposite directions along co-linear portions of the aperture. Thereafter, knife edges aligned in the same direction along differing portions of the aperture are illuminated. During this last knife edge measurement, the optical prescription of the eye is determined.

An advantage of the sequence of examination of the eye using the detector of this invention is that two discrete measurements with the preferred detector can occur. First, and using knife edge pairs, each member of the pair being co-linear but opposed knife edges, the centroid of the eye is determined. Thereafter, and using different knife edge pairs, each member of the pair being parallel aligned spaced apart but with knife edges faced in the same direction refractive information is determined. This information originates in the difference sensed at the detector in the light level returned from the eye between the interrogations of the second and different knife edge pairs. This difference contains prescriptive information which is insensitive to and separate from the positional information.

A further advantage of this invention is that the output of the detector readily adapts itself to driving motors in corrective optics. Motors can be activated to null errors and produce emmetropic refraction of the eye through corrective optics.

An advantage of this apparatus and method is that the eye is first positioned with precision with respect to the objective refractor. During this position, all ambient optical errors in the eye are ignored. Thereafter, and once the eye is properly measured for position, the optical errors of the eye are determined. This is determined even though minute movements of the eye being tested may naturally occur. Such minute movements are ignored.

A further object of this invention is to disclose an overall and automated sequence of operation. According to this aspect of the invention, the instrument is first grossly aligned by an operator to acquire the pupil of the eye to be examined. Secondly, and in response to tromboning of roof mirror system in the first Badal optics, overall instrument movement occurs until the eye is acquired at a sensed optical null in the detection. Once the null position is found, both spherical and astigmatic testing of the eye using the knife-edge sequences previously disclosed are utilized. These respective sequences determine the prescription -- this all being determined in the infra-red wave length.

An advantage of this aspect of the invention is that the instrument first adjusts itself optically to acquire the eye being examined. This optical acquisition can be compared to the use of a finder in the large astronomical telescope. The finding mode of the instrument allows the eye to be acquired and the rough prescription of the individual eye to be determined in sphere.

Yet another advantage is that once the eye is roughly located, the disclosed and discrete optical tests utilized herein can occur. These tests comprising sequential interrogation by knife-edges, with corresponding objective variations of the prescription in sphere and cylinder. Tests occur in the infra-red.

Yet another advantage of this invention is to illustrate how an identical optical path can be utilized for testing the results of the objective refraction by displaying to the tested eye a target to be seen visually. According to this aspect of the invention a beam splitter detouring part of the path to a visual target is disclosed. Discrete movement of the optics of the invention is set forth. Guidelines for affecting the amount of movement are prescribed. An advantage of this aspect of the invention is that immediately after objective refraction has occurred in the infra-red, the refracted subject is displayed a visual eye chart. This eye chart includes the determined refraction. Rough subjective testing of the individual can occur.

Other objects, features and advantages of this invention can be understood after referring to the following specification and attached drawings in which:

FIGS. 1A–1H are respective illustrations and projections of light rays through the human eye from a knife edge and illustrating in schematic form the shape of knife-edge images to be viewed;

FIG. 1A illustrates an eye with a "near-sighted" or myopic condition;

FIG. 1B is a schematic of the characteristic image produced by such eye;

FIG. 1C is a deflection schematic of a positive spherical lens producing such a condition;

FIG. 1D is a schematic of an eye with a "far-sighted" or hyperopic condition;

FIG. 1E is a schematic of the characteristic image produced by such an eye;

FIG. 1F is a vector schematic of a lens for producing such a condition;

FIG. 1G is a combined vector schematic, knife edge and characteristic image schematic of an eye having astigmatism oriented along a 45°/135° axes; and FIG. 1H is a combined vector schematic, knife edge and characteristic image schematic of an eye having astigmatism oriented along 0°/90° axes;

FIG. 2 is a perspective view of a prior art image detector illustrating an embodiment in which high noise levels are present;

FIG. 3 is an embodiment of a low level light detector according to to this invention wherein an image of a light source is focused to dispersing prism wedges and these wedges proportionally displace the resultant image to discrete photosensitive surfaces;

FIG. 4A is a perspective view of a specialized cylindrical lens matrix utilized with this invention, the cylindrical lens matrix having an underlying schematic drawing for explaining the function of the lens;

FIG. 4B is a diagram of illustrated segments of the cylindrical lens, this diagram illustrating respective segments of positive sphere, negative sphere and two components of astigmatism along opposite axes;

FIG. 5 is a perspective illustration of a four element lens projected by a spherical lens system from a light source to an imaging plane;

FIG. 6 is a perspective similar to FIG. 5 with multiple lens segments being illustrated;

FIG. 7 is a perspective view similar to FIG. 6 with three knife edges disposed at an angle over the face of the lens element;

FIGS. 8A, 8B and 8C are respective representations of lens elements and resultant images on detecting planes of a plurality of knife edges disposed over the specialized lens element of my invention;

FIG. 9 is a perspective view of a low light level detector according to the preferred embodiment of this invention, special note being made that the resultant matrix of photodiscrete segments is subject to coordinate transformation to measure the applicable deflection;

FIG. 10A is a side elevation schematic of a knife edge test on the eye of a myope illustrating the factors involved in the image produced in the eye during knife edge testing;

FIG. 10B is an illustration of a knife edge with the cylindrical matrix of this invention only schematically shown illustrating the preferred enhancement of the image utilizing the cylindrical matrix and knife edge in combination;

FIG. 11 is a preferred embodiment of the projection system of this invention utilizing a projection lens, with weighted illumination surfaces being present for both control of flare and background specular reflection; and, FIG. 12 is an alternate embodiment of the system of this invention utilizing a lens matrix to both project light to the eye and receive light from the eye.

FIG. 14A is an optical schematic illustrating with respect to the lens element originally illustrated in FIG. 4A how adjacent optical elements detour light to particular detector quadrants;

FIG. 14B is an illustration of detector quadrants fabricated from equal cross cylinders, here shown as negative cylinders combining to be negative lenses, which detector quadrants in turn may be divided into four portions with each portion detouring the light impinging thereon to a particular and discrete detector segment;

FIG. 14C is an illustration demonstrating how a multiplicity of elements reduces the criticality of knife edge alignment with respect to the lens segments;

FIG. 15A is a schematic illustration of knife edges cutting the lens element of FIG. 14B with distribution of the light being shown over the detector segments;

FIG. 15B is a schematic illustration of displacement in the X direction of the image shown in FIG. 15A, and particularly useful for explaining the weighting of the image with respect to the Figure;

FIG. 15C is an illustration similar to FIG. 15B with the displacement of the image here occurring in the Y direction;

FIG. 16A is a schematic of the improved detector head of this invention illustrating the two by two central aperture, and the four one by one peripheral apertures with the respective alignment of the knife edges set forth;

FIG. 16B is a plan view of the detector of FIG. 16A illustrating the apertures and knife edges;

FIG. 16C is an illustration omitting a portion of the optical train and illustrating how the detector of this invention is utilized to place an eye in proper position for measurement, three detector states being illustrated, the detector states being the eye too close for examination, the eye too far away for examination, and the eye properly positioned for examination;

FIG. 16D is an illustration similar to FIG. 16C with the knife edges being illuminated in an interrogating sequence designed for determining the refractive corrections necessary for the eye;

FIG. 16E is a perspective embodiment of an eye having imaged light sources therein with the light sources relayed to a position in front of the specialized optics with resultant projection to a detector illustrated;

FIG. 16F is an illustration of the detector plane illustrating how specular reflection is eliminated as a consideration where interrogation by the objective refractor occurs;

FIG. 16G is a perspective representation similar to FIG. 16E utilizing one knife edge, which knife edge when incorrectly placed towards and away from the detector screen produces error in the resultant signal;

FIG. 16H is a view of the detector of FIG. 16G;

FIG. 16J is a perspective view similar to FIG. 16E, 16G with the utilization of three knife edges being illustrated;

FIG. 16K is a view of the detector surface of FIG. 16J illustrating the detector correctly placed and focused;

FIG. 16L is a view of the detector of FIG. 16J showing a placement of the detector in an incorrect alignment with the respective images on the detector still registering the correct optical prescription;

FIG. 17 is a perspective view of the preferred "pebble plate" of this invention wherein side by side negative lens surfaces are impressed on a refractive element; and FIGS. 18A–18D are respective schematic illustrations of a knife edge and detector surface illustrating the so-called "push-pull" knife edge interrogation of the eye.

FIG. 19 is a perspective view of the instrument of this invention as actually developed for objectively refracting the eye of the viewer;

FIG. 20 is a view of the double Badal type optical train utilized with this invention;

FIG. 21 is a schematic view of the improved detector head of this invention illustrating the four opposed knife-edges in a cross-alignment for interrogating the eye once the eye is acquired;

FIG. 22 is a plot of the intensity of the signal received as the eye is initially acquired; and, FIG. 23 is a reproduction of portion of U.S. Pat. No. 4,070,115 incorporated in this patent by reference.

Referring to FIG. 1A, a human eye E having a cornea C and a lens L is shown viewing a knife edge K. Knife edge K includes an illuminated portion 14 and an edge portion 15. A line 16 is shown passing immediatly above edge 15 and terminating in a point (shown by an X) on the side of the knife edge opposite the side facing the eye E. Observation of the illuminated portion of the pupil of the eye is made from point X. The knife edge is typically placed at an optically infinite distance from the eye by the expedient of collimating optics (not shown). Alternatively, projection of the knife edge may occur to any known optical distance.

It will be appreciated that although the side 14 of knife edge K is illuminated or luminous, this illumination terminates along edge 15. Thus no light can be incident through lens $L_e$ onto the rear retina R of the eye from points above edge 15.

Hereinafter, when the term "knife edge" is utilized, it will be understood that three discrete functions are referred to.

First, there is a light source. Secondly, the light source terminates along a boundary defining a straight line or knife edge terminator. Thirdly, the knife edge terminator defines immediately thereover an optical path to a detector element.

The illuminated surface below knife edge 15 will produce illumination on the retina R. FIG. 1A assumes that eye E is afflicted with myopia. The image plane 18 of knife edge K through lens L will be in front of the plane of the retina of the eye. A point along this image plane will form an illuminated oval shape 20 on the retinal surface of the eye.

An observer placed at point X and peering over the top of the knife edge will thus see the lighting returning from oval area 21 on the retina of the eye.

It will be seen that the area of illumination 20 and the area 21 overlap. This area of overlap is identified by the numeral 24. Rays from area 24 may be traced back to the portion of the lens $L_e$ that will appear to an observer at 16 to be illuminated. Specifically, the light will appear to be apparently from the bottom of lens $L_e$.

Referring to FIG. 1B, an image of how lens $L_e$ will appear is drawn. This image of lens $L_e$ shows the illuminated portion caused by light returning from sector 24 within the circle of possible returning light 20 as viewed from point X along line 16 above knife edge 15.

It is important to note that this view is a characteristic of the knife edge. It indicates that lens $L_e$ is excessively positive and the eye E has myopia.

Immediately above FIG. 1B is a schematic diagram 1C. Schematic diagram 1C illustrates in vector format the excessive positive power of lens $L_e$ and/or C in FIG. 1A.

Turning to FIGS. 1D, 1E and 1F, farsightedness or hypermetropia is illustrated. Knife edge K with illuminated portion 14 stopping at terminator 15 projects light to the retina R of an eye through a cornea C and a lens $L_e$. As previously shown, the focal plane 18' is here behind the retina R. Projection of the knife edge to optical infinity is assumed and not shown.

Taking projected light from the eye, an oval of illumination 23 from one point of source area 14 will be shown on the retina.

Viewing from a point behind the knife edge (on the side away from the eye) along line 16 above the terminator 15, will allow the person to collect light from oval area 25. The viewer will see light returning from an illuminated portion 23 of area 25.

FIG. 1E is a view of lens L and how lens L appears to be apparently illuminated. Referring next to FIG. 1F, a schematic representation of the negative deflection of the lens $L_e$ or C is illustrated in vector format.

Referring to FIG. 1G, only a schematic representation of a lens L, a knife edge K and a retina R is illustrated. Lens L is illustrated in the schematic vector format similar to FIGS. 1C and 1F. In FIG. 1G, lens L is a cross-cylinder lens having power obliquely aligned to edge 15. This lens has astigmatism along 45°–135° meridians. Lens L has a positive power along meridian 30 and a negative power along meridian 31. It will be noted that the respective meridians 30 and 31 are at preferred 45° angles to edge 15 of knife edge K. Noting the meridians 30, 31, the deflecting power in the vicinity of these meridians can be shown. For example, and commencing clockwise from the right, at the three o'clock position 32, light will be deflected downwardly. At the six o'clock position 33, the light will be deflected to the right. At the nine o'clock position 34, light will be deflected upwardly. Finally, at the 12 o'clock position 35, light will be deflected to the left.

Analyzing the action of such a lens in conjunction with a knife edge K can be quickly understood. Light on one lateral half of the lens passing above the knife edge K will be deflected to the examined eye where it can be viewed. Light on the opposite segment of the lens L will be deflected into the knife edge K where it may not be viewed. Consequently, the image of the retina R will have a terminator T at right angles to the edge 15 of knife edge K. One segment of the lens L will be illuminated. The illuminated portion of the lens L is shown at 36. As previously set forth, the terminator will not be sharp but rather have a blurred edge. The term "terminator" should be understood in this manner as it is used hereafter.

The case of a lens L having 0°–90° astigmatism can be understood with reference to FIG. 1H. Specifically, in FIG. 1H, positive cylinder is placed along meridian 40 which is normal to edge 15 of knife edge K. Negative cylinder is placed along meridian 41 which is parallel to edge 15 of knife edge K. The image at the retina R includes an illuminated portion 46 with a terminator T that is parallel to knife edge K.

Referring back to FIGS. 1B and 1E, it can be seen that the terminators T are in substantially the same horizontal direction as the knife edge. This being the case, it will immediately be realized that astigmatism with axes either parallel to or normal to the edge 15 of knife edge K will appear the same as spherical components. Consequently, and when utilizing only one knife edge, only one component of astigmatism can be measured. The measurements of components of astigmatism normal to or parallel to the knife edge cannot be made. We can only say that the information produced from such a measurement is an indication of a "meridiodinal" power. This measurement can be shown to make sense and be collated to knife edges K having alignments normal to the edge 15. For example, the reader is invited to review my U.S. Pat. No. 4,070,115, issued Jan. 24, 1978, wherein knife edges of differing angles are utilized for the testing of common lenses.

Having set forth the characteristic light patterns that may be produced on the retina of the human eye with knife-edge testing and directly observed, reference can now be made to the problems encountered in using knife-edge images for remote detection.

Specifically, and where any kind of an image is projected onto the retina of the human eye, the intensity of that image must necessarily be low. Where the image is in the visible spectrum, the glare problems on the retina are obvious. Where the image is either visible or infrared, the images must be of a sufficiently low intensity so that the eye is not burned. Remembering that the rays are in effect focused by the lens L on the retina R of the eye, one can immediately understand that the projected light must simply be of a low light level.

When the optics of the eye are utilized to view the illuminated retina, as in the classical case of conventional objective refraction, only a faint image will be visible. This faint image must be remotely detected if an objective refractor is to be automated. Moreover, the edge or "terminator" of the image will be far from sharp. The overall image must then be located on "weighted" basis. The problems associated with the projection of such faint images will now be discussed.

Referring to the prior art apparatus illustrated in FIG. 2, a low level light detector is illustrated. Light source S movable about an XY plane P is imaged through a lens L to a photosensitive surface D. Photosensitive surface D typically includes a single and continuous photosensitive surface, either of the photoconductive or photoresistive variety. Typically, such surfaces have a "common" first connection 50 and are monitored by evenly spaced electrodes 51, 52, 53, 54.

Terminals 51–54 are symmetrically spaced about the periphery of photosensitive surface D. Each of the terminals is typically connected by leads to the input of an amplifier 55. Amplifier 55 is of conventional design and amplifies the difference in electrical signal to produce an output proportional to X and Y at 56.

When the embodiment of FIG. 2 is applied to a source S of extremely low light level, a difficulty arises. Typically, all the terminals 51–54 are connected to a single continuous and conductive layer of the photosensitive material. All these terminals have substantial conductivity between them. This relatively low resistance and high conductivity must be sensed at amplifier 55 in order to generate a signal at terminals X and Y which is proportional to the displacement of image of source S.

Where a high conductivity and hence low resistance is present across electrical terminals, the intervening random motion of electrons creates noise. This noise when received at amplifier 55 and suitably amplified along with the outputs for X and Y results in a low signal to noise ratio. Signal is rapidly lost as the intensity of source S diminishes. For example, where source S images at S' on detector D, the predominant signals at terminals 51, 52 could well be lost in the resultant noise.

The problem therefore becomes one of designing complimentary optics and photodetectors which suppress the tendency of the detector shown in FIG. 1 to produce resultant noise at low image intensity levels.

I will disclose two embodiments. The first of these embodiments will be illustrated with respect to FIG. 3 and illustrates a first conceived and less preferred way of acquiring low light level sensitivity.

Thereafter, and with respect to the remaining illustrations, I will illustrate a preferred knife edge and lens array. This preferred knife edge and lens array illustrates not only a new and useful lens, but additionally discloses the new light detector of my invention.

Referring to FIG. 3, and in understanding my first invention, I will first set forth the configuration of a plate W. After discussing my plate W, I will thereafter set forth the remaining optics and operation of the system.

Plate W consists of a matrix of optical wedges. This matrix has a first and upper side 60 and a second and lower side 62.

For the convenience of the understanding of the reader, lens W here is shown of composite manufacture. A first roof prism 64 is positioned in the middle of lens W.

The processing of light received uniformly over the top of prism 64 is easy to understand. A first portion of the light will be directed to detector segments $D_1$ and $D_2$. A second portion of the light incident upon prism 64 will be deflected to detectors $D_3$, $D_4$.

Turning now to an outboard prism 65, it can be seen that this prism 65 only includes one facet. This facet will cause light incident uniformly over the top of prism 65 to be deflected only to segments $D_1$, $D_2$. No portion of prism 65 is disposed to deflect light to detector segments $D_3$, $D_4$.

Prism 66 on the opposite edge of lens W is configured in the opposite direction. Specifically, light passing from the direction of source S through prism 65 will be incident upon detector segments $D_3$, $D_4$; no light will be incident upon detectors $D_1$, $D_2$.

The intervening prisms 67 and 68 can now be easily understood. Prism 67 has a first portion biased increasingly in favor of segments $D_3$, $D_4$ and a second portion or slope biased to a lesser extent to deflect light onto the detector segments $D_1$, $D_2$. Prism strip 68 has segments similarly constructed but biased more in favor of detector segments $D_3$, $D_4$, and less in favor of detector segments $D_1$, $D_2$.

Stopping here and understanding the right hand and upper portion of lens W, it will be immediately seen that the further light is deflected towards the right hand portion of lens W, the more light will impinge on detector segments $D_3$, $D_4$ and the less light will impinge on segments $D_1$, $D_2$.

The intervening prisms 69 and 70 on the opposite edge of lens portion 60 can just as easily be understood. Prism 69 has a first facet biased increasingly in favor of segments $D_1$, $D_2$ and a second facet so biased to a lesser extent to deflect light onto detector segments $D_3$, $D_4$. Prism strip 70 has facets similarly constructed but biased more in favor of detector segments $D_1$, $D_2$, and less in favor of segments $D_3$, $D_4$.

Stopping here and understanding the left hand and upper portion of lens W, it will be immediately seen that the further light is deflected towards the right hand portion of lens W, the more light will impinge upon detector segments $D_1$ and $D_2$ and the less light will impinge upon segments $D_3$, $D_4$.

The prisms of side 62 of the lens are constructed in an analogous fashion. Here, however, the prisms run left and right. Deflection is divided between detector segments $D_1$, $D_4$ on one hand and $D_2$, $D_3$ on the other hand.

Recognizing that the matrix of prisms is formed by the plate W, it will be seen that each area of the matrix consists of the effect of an overlying and underlying prism. These prisms will deflect light to the detector segments proportional to the location at which a source S is imaged.

Passing onto the remainder of the detector, a source S is schematically shown movable in an XY plane P. This source S is imaged through a lens 80 so that the image of the source S falls upon plate W at S'. Assuming that the image at S' is equal to or larger than one of the areas formed by overlying prisms strips, deflection of the light onto the detector segments $D_1$–$D_4$ will be weighted in accordance with the position of the image S' on the plate W. A lens 80' underlies plate W to relay the deflected images to the detector plane. Use of this lens is optional, but not required.

Detector D is typically a photodetector and can include photoconductive cells, photodiodes, photoresistors, phototransistors, and any other light sensitive detector. Specifically, the segments $D_1$, $D_2$, $D_3$, and $D_4$ are all photodiscrete; that is to say they are electrically separate one from another. Each segment $D_1$–$D_4$ has only one electrical connection and the current between "common" and the electrical connection is indicative of the amount of light incident upon that particular detector segment.

By way of preferred example, a photosensitive cell including layers of doped silicon of P and N types bonded to an aluminum surface with appropriate electrical connectors on top and bottom, such as manufactured by the United Detector Technology Company of Culver City, Calif. can be used.

The amplifier 55 is a conventional current to voltage converter and amplifier.

In operation and assuming that an image S' is projected to plate W, light is proportionately distributed by the prism segments in the matrix to the respective detector segments $D_1$–$D_4$. By amplifying and logic circuitry standard in the art, a signal indicative of the X,Y position of the image S' on the plate W is produced. Note that "X" and "Y" as shown in FIG. 3 are along the diagonals relative to the detector boundaries.

It will be noted, that as distinguished from the embodiment of FIG. 2, the respective detectors are photodiscrete. The resistance between any two of the terminals is essentially infinite as it constitutes an open circuit. Only the amount of light falling on the detector segments produces the desired proportional current flow. Hence, and even with incidence of low levels of light, the disclosed detector arrangement is essentially free of noise from the electrical interaction of the detector segments.

Turning to FIG. 4A, I will now illustrate the preferred lens array and preferred knife edge. This embodiment will first be discussed illustrating the make-up of a new lens utilizing FIG. 4A. Referring to FIG. 4B, I will illustrate the optical characteristics of each of the lens segments.

Referring to FIG. 4A, lens V consists of a series of side-by-side cylindrical lens strips. Positive cylindrical lens strips 80 have inserted intermediately negative lens strips 81. These strips 80,81 alternate in side-by-side relationship with the lens strips themselves extending along the width of the lens parallel to arrow 86. Together the side-by-side lenses make up a first half of the lens generally denominated as 88.

A second and lower half of the lens 89 consists of side-by-side positive lens strips 83 and negative lens strips 84. As was previously the case, the side-by-side strips extend across the lens parallel to the dimension arrow 87 and form together the second side of the lens 89.

The reader will realize that the lens here illustrated has been shown of composite make-up. In actual fact, the divisions between the cylindrical segments 80, 81 and 83, 84 are not visible. Typically, the entire lens is fabricated from molds and is made up of a uniform optical material which can be impressed with the desired shape, such as a lens plastic. As with the earlier example, this optical element may also be fabricated with one flat surface and an opposite composite surface having the desired deflections herein described. Having set forth the make-up of the lens with respect to FIG. 4A, the optical effects of the underlying matrix will be set forth with respect to FIG. 4B.

Referring to FIG. 4B, it will be remembered by those having skill in the optical art that two cylinders of equal powers set at right angles one to another can combine to be the equivalent of a spherical lens.

Looking at a first segment comprising cylinder segments 80, 83, it will be immediately seen that a positive spherical lens effect C+ results from the combination of the crossed cylinders. Conversely, and referring to crossed negative cylindrical lenses 81, 84, it will be just as quickly realized that the crossed negative lenses result in a negative spherical lens effect C−.

It will be just as quickly remembered that the combinations of crossed positive and negative cylinders have an overall cylindrical effect. In this way, it will be seen that segments 80 and 84 at the juncture where they cross form a combined crossed cylindrical lens $A_1$. Similarly, crossed negative and positive cylinders 81, 83 form a combined cylindrical lens $A_2$.

Stopping here and referring back to FIG. 4A, it will be seen that each of the discrete lens segments can now be labeled. They can be labeled according to their power. As the pattern in FIG. 4B is repetitious, such labeling of a small portion of the matrix continues throughout the entire lens.

Returning to FIG. 4B, various parallel rays in their passage through discrete lens elements have been illustrated as deflected. These illustrated deflections of light can be used to generate a vectorial description of lens deflection.

Referring to the illustrated lens deflections, it will be seen that each lens segment shown in FIG. 4B has arrows drawn in the corners of a figure, which figure is a projection of the area of the segment. These arrows can be seen to be descriptive of deflections produced. They will hereafter be used to describe deflection produced by my invention.

Referring to FIG. 5, a point source of light S projects light through a spherical lens L to an image plane D. We all know that for all points within the system, that the light will again project to a center point S' on the image plane D.

We now put in lens element V, which I have invented. When plate or lens V goes in, we have a matrix of four side by side lenses. Only one such matrix of four lenses is illustrated in FIG. 5. In the preferred embodiment this matrix is repeated many times.

Denominating the respective segments, we can put in the designations C+, C− for the respective positive and negative spherical lenses. Likewise, we can put in the designations A1 and A2 for identifying the astigmatic segments of the lens.

We may study another constraint of the system.

Remembering that all points S when imaged through lens L converged on the points S', we may now ask ourselves what happens to rays passing through neutral points of the lens segments C+, C−, A1 and A2. In each case, we find that the rays against must end up on the point S'. The question then becomes, how are the remaining rays deflected?

We know that we can use vector descriptions developed with respect to FIG. 4 to describe the deflection of light. This vector description can be made for each of the lenses about its neutral point. We therefore can sequentially describe what occurs at each of the remote segments of the C+ lens. Taking the principal ray of the system passing through point 114, we know that in the absence of specialized lens V that impingement would be on point S'. However, and due to the vector deflection towards the center of the spherical lens C+, we instead will have incidence upon a point 24.

An analysis of a point diametrically opposite the positive spherical lens C+, can be similarly made. Deflection will occur from the normal impingement S' to a new point 25 on the image plane.

Similarly, for a point 116 on the plate V, a deflection to the point 26 on image plane S will occur. This deflection detouring light that was originally intended for point S'. Finally, and from point 117 on lens C+, we find imaging occurring at a point 27.

We may now discuss the case of a negative lens.

Negative lens C— includes a remote point 115' which point 115' again images at point 25. Similarly, it includes a point 116' and 117' which points again image about point S' as previously described.

It will of course be appreciated at this point with respect to the astigmatic segments of the lens A1 and A2 that only two remaining deflections may be described. Specifically, these deflections are 115" and 115'" at the respective corners. Light rays at these points will be deflected to point 25.

It will be hereafter seen that what results from the projection of the source S passing through lens L with the specialized lens V substituted therebetween is an evenly distributed square light pattern on the focal plane D. This image on the plane D has a square shape. With movements of S along the X and Y axes, corresponding movement of the square image on plane P will likewise occur.

Turning to FIG. 6, we again have a source S movable in an XY plane. Source S has an image on imaging plane D through a lens L. A specialized lens element V causes a deflection pattern with light contained inside a square boundary, as explained in the case of the matrix of four sections.

Lens V is divided into lenses C+, C—, A1, and A2 as previously described, this time in a matrix of well over four such sections. Due to the complexity of the figure, only some of each of the representative lens segments are labeled with the appropriate designations C+, C—, A1 and A2.

Continuing on with the view of FIG. 6, we note again that all segments of the lens project light in square patterns. The light falls within a boundary of a square delineated by the points 24–27 as previously described.

Similar to the case previously described, we know that where translation occurs, this translation will result in a deflection of the entire square image formed by the boundaries 124–127.

Placement of knife edges at varying alignments across the lens element can be instructive. Turning to FIG. 7, a source S images through a lens L to an imaging plane P. Again, the specialized lens V is interposed this lens having a configuration the same as previously described in FIG. 6. This time, however, a knife edge is placed across the lens element at position K1, forming a limiting aperture through which light from source S can pass through lens V and hence be imaged by lens L on image plane P.

As will hereinafter be more fully set forth, it is required that two conditions be met by a knife edged aperture disposed on the lens V.

First, the edge of the aperture must traverse equal portions of each of the four element types comprising specialized lens V (C+, C—, A1, A2).

Secondly, the edge of the aperture must be disposed across the lens V, at an especial slope to the boundaries of the lens elements of the matrix and not parallel to these boundaries.

A particularly preferred embodiment is a slope of 2:1. The preferred slope is shown in FIG. 7. Every time the illustrated knife edges traverse two elements disposed in the horizontal direction, the knife edges traverse one element disposed in the vertical direction. Other especial slopes, designed a b, will also obtain the desired effect if and only if a is odd, when b is even, or b is odd when a is even, where a and b are whole numbers.

Knife edge K1 passes through point 135 on lens A1 and point 136 on lens C—. It is known from the example of FIG. 5 that at these two points, that it will image at respective points 125, 126 on image plane P. The question then becomes where will imaging occur medially for light rays passing between points 135 and 136, say at point 140. Realizing that point 140 is the peripheral edge of a negative cylindrical lens C—, the problem is simplified. Specifically, it can quickly be seen that a full negative deflection will be to the periphery of the square at a point 150. Thus, taking the case of parallel rays passing sequentially across a knife edge from the point 135 to the point 136, it will be quickly seen that the light rays will image along a line 125, 150, 126.

Taking the case of knife edge K2 and passing from left to right the deflection may be understood by superimposing thereon a similar vectorial analysis. Starting at point 141 on the left hand edge of knife edge K2, it will be remembered that we are in the middle of a positive spherical segment C+. Deflections will be vectorially distributed towards the neutral portion of the element. Impingement of light at point 151 will result. Taking light incident upon knife edge K2 at point 142, it will be seen that this point is at the upper segment of a positive spherical lens. Deflection will therefore be downwardly and to the neutral point of the lens with resultant impingement of the light at a point 152.

At point 143, the light will impinge upon at a boundary between the two lens elements, the boundary here being that of a fully negative lens, C—. This fully negative lens will cause light incident at that point to be incident at point 153.

At point 144, it will be noted that knife edge K2 passes through the neutral portion of a negative lens. Consequently and in passing through the neutral portion, it will be incident upon the center of the square at the point S'. Finally, and in passing point 155, light will be incident on the edge of the square at 155. There results the shown traced zigzag pattern of traced K2'.

We now for purposes of instruction trace the path of ray grazing knife edge K3 as it passes through the element. We note that knife edge K3 begins at point 146. Point 146 is a section of a positive spherical lens C+ and projects to point 156 on image plane P.

At point 147 we note that the light ray is at a corner of a positive spherical lens C+ and a negative spherical lens C—. Light projected from point 147 following the same logic as in FIG. 5 ends up point 127 on plane P. Light from point 148 plots similarly. This light at a periphery of a negative lens element ends up at point 158. Thereafter, light from point 159 deflects to point 159.

We thus have traced knife edges K1, K2 and K3. There therefore remains the problem of tracing a more complex array in a similar manner. This has been illustrated with respect to the schematic plots of FIGS. 8A and 8B.

Referring to FIG. 8A, it is instructive to illustrate deflections of knife edges disposed along FIG. 8A on the square image trace of FIG. 8B. Here, the observer will note that the light source S and the lens L have been omitted. All we are now going to view is the knife edge as it is disposed across the lens element V (identified in FIG. 6), such knife edge being shown on FIG. 8A and the resultant traced pattern as it appears in FIG. 8B.

Taking a knife edge defined by the points 180, 181, 182, 183 and 184, the trace can be rapidly generated. Taking point 180, it is observed that this point is at the edge of a positive spherical lens. Remembering that in the absence of plate V it would have been deflected to the center of the diagram at point 195 and remembering also that it is given a vectorial deflection by the lens element along the diagonal direction, it can be seen immediately that it arrives at point 194. Taking point 181 along the knife edge, 181 will be seen to be a portion at the edge of a negative cylindrical lens. This point is horizontally located from a neutral segment of a negative lens C−. Accordingly, the lens ray will be incident at a point 191. By the same logic, light rays intermediate point 190 and 191 will fall along a straight line connecting points 190, 191.

Light from point 182 will project to the upper righthand corner at point 192. Remembering that it would originally have been directed at point 195 and remembering also that it is at an edge of a lens C+, it will be directed to the upper righthand corner of the diagram.

Light from point 183 will be incident upon the same point as light from point 181. Remembering that light at point 183 is on the edge of a positive spherical lens and that the positive sphere is directed to the left, deflection will be to the boundary on the left.

Finally, light from point 184 will project to point 194 which is coincident to previously alloted point 190.

We thus see that light along a knife edge intersecting the diagonal points of the lens always plots as a V.

It is interesting now to investigate light which passes through neutral points of the segments of the specialized lens V. This has been plotted along the line which runs 186, 188, 185, 189, 187, 188', 189'.

First, the case of light at point 185 can be easily demonstrated. In that case, we know that the light will in no way be deflected. No deflection will result at impingement of point 195.

Light incident on the lens of FIG. 8A at point 186 falls on the edge of a positive spherical lens. Falling on that edge, it must be deflected to point 196 on FIG. 8B.

Likewise, light incident at 188 falls on the edge of a negative spherical lens. This negative spherical lens plots out at point 198 on the diagram of 8B. Similarly, light at point 189 falls on the opposite edge of a negative lens. This light plots out at point 199 after passing through the neutral point 195 of the lens. Thus, as the knife edge traverses the negative lens C−, we see that we get a linear deflection from points 198 to 195 and finally to point 199. At point 187, we are at the edge of a positive spherical lens. This will deflect to point 197 as illustrated in FIG. 8B. Light at point 188' will be at the edge of a positive spherical lens. This will plot out at point 198'. The traverse of the knife edge from point 188' to point 189' must pass through a neutral segment of the lens at 195. It will be found that point 188' plots on the lefthand edge at 198' and point 189' plots at the righthand edge at 199'. Thus we see we get a pattern that almost looks like a figure 8 drawn with straight lines that repeats upon itself. It is not unlike a Lissajous pattern drawn with straight lines.

FIG. 8B is written on a background. This background includes horizontal axis X and vertical axis Y. The figure projects along boundaries 100, 101, 102, 103 (labeled clockwise).

We can also see that each of the lines traces into respective quadrants of these figures. These quadrants themselves can be labeled quadrant 104, 105, 106, 107.

An interesting observation can be made. The length of line resultant from the projections of the knife edge in each of the quadrants is equal. It is equal in linear length. It is also equal in the center of gravity sense. Specifically, it will be found that the center of gravity of the line segments in all portions of the images falls symmetrically about point 195.

We now go to FIG. 8C. FIG. 8C is a diagram of the matrix of FIG. 8B superimposed upon a detector. The detector includes photodiscrete quadrants $D_1$, $D_2$, $D_3$ and $D_4$. Each of these quadrants has approximately the same area as the boundary square which includes the deflection patterns produced by the respective knife edges. At this point, it will be seen that the image in FIG. 8C has been moved along a diagonal 110 to the upper left. As previously illustrated, the detector segments are photodiscrete or separate along lines of division 114, 115.

In order to measure a deflection of the image on a proportionate basis, it is necessary that the amount of line cut from a given knife edge always be proportionately distributed in each of the detector segments $D_1$–$D_4$. This proportionate distribution should be equal to the direction and amount of displacement which has occurred. Therefore, where a displacement is along and parallel to a diagonal 110, respective detector segments $D_1$ and $D_3$ should have equal amounts of light incident upon them. There should be no difference in signal registered between them to indicate a displacement other than along diagonal 110.

In FIG. 8C, the trace of the knife edge of point 180, 181, 182, 183, 184 of FIG. 8A has been generated. This trace plots is given the same numeric designation.

It can be demonstrated and is indeed apparent from a visual inspection of the drawing, that the linear length of light line appearing in detector segments $D_1$ and $D_3$ is equal. The linear length of light line appearing in segments $D_2$ and $D_4$ is not equal. The difference is proportional to the displacement as it is occurred along the diagonal 110. Plot of the knife edge designated by points 186, 188, 185, 189, 187, 188', 185', 189' of FIG. 8A yields the same results, and it will be found that the amount of line residing in detector segments $D_1$ and $D_3$ is the same. The amount of light line remaining in detector segments $D_2$ and $D_4$ however is again different and by the same amount as before.

Displacement along the opposite diagonal 111 will yield a similar result. Moreover, I have found that displacements on any direction followed the above rule. The difference in the amount of light line that is laid down between any opposite quadrants will be proportionate to the displacement. It is this result which allows me to apply this detector for the detection of low level light sources with photodiscrete detector segments.

It will be seen that the center of gravity 195 will thus be tracked in its displacement according to the difference in amount of light received at each of the detector segments. It is therefore possible to get a linear output.

Putting an infinite number of knife edges or narrow bands of light across the lens elements, it will be immediately realized that the result will be a solid, evenly distributed patch of light inside a boundary of the same shape as the lens elements. This patch of light will be the conjugate image of every point source of light in a faint and measured image. By utilizing a summation of these conjugate distributed images, each bounded in a square, I have a peculiarly useful detector image which incident upon a detector plane will read out X and Y positions for the center of gravity of a faint and remote image. It is this characteristic of being able to recognize the center of gravity of a faint image that enables this detector to be peculiarly useful.

Having described the construction of the lens element and the deflection that is utilized within the lens element, the apparatus of FIG. 9 can now be set forth. Referring to FIG. 9, a light source S is illustrated in XY plane P. This source S projects past a lens L and lens element V. Lens element V projects an image of light onto a detector surface D having photodiscrete quadrants $D_1$–$D_4$.

In the embodiment of FIG. 9, it will be noticed that source S illuminates the upper righthand quadrant of plane XY. The low level intensity image is projected from source S through the combined lens L and specialized lens V.

Specialized lens V is surrounded by knife edges K1–K4. These respective knife edges all establish an opaque terminator to the otherwise transparent lens V previously described.

Two optical effects are present when source S projects its light past lens V and the knife edges K1–K4.

First, the knife edges when projected to the surface of the detector D including the photodiscrete segments $D_1$–$D_4$ are at an angle to the square sides containing the illumination.

Secondly, the resultant light from any point on the image forms an evenly distributed square image, which evenly distributed square image is translated on the detector segments in accordance with the translation of the source S at the plane P. Thus, where the source S moves to the upper right hand quadrant of the source P in FIG. 5, the square patch of light would move to the lower left relative to an XY plane. Moving to the lower left relative to an XY plane, the detector of FIG. 9 when connected to a standard circuit such as that shown in the amplifier of FIG. 1 can read out in the XY position.

It will be realized, however, that due to the properties of the image, a coordinate transform will have to be applied as the edged directions and coordinate directions will differ. Since such coordinate transforms are wellknown in the art, they will not be repeated here.

The disclosed lens element has an unexpected result, when utilized to project light and receive light over a knife edge to and from an eye. FIG. 10A is a schematic diagram of light from a knife edge test impinging upon the eye of a myope. FIG. 10B is a schematic illustrating the principle of how as light comes to a focus a signal enhancing displacement occurs.

Taking the case of the eye previously illustrated in FIG. 1A, it will be remembered that this eye suffered from the vision defect of myopia.

Returning to FIG. 10B, a series of light rays passing from knife edge K can in sequence be considered. Each of these light rays when passing from the knife edge must first pass through lens V. In passing through lens V, the light rays dependent upon their respective left to right points of origin encounter from left to right across the top of the knife edge lens segments A1, C+, C− and A2 at the lens V point of meridiance.

Referring to FIG. 10A, a schematic of the knife edge test of FIG. 1 on the eye of a myope is illustrated. This figure illustrates the physics of the resultant rather indefinite image produced on the retina. A knife edge K illuminated at a portion 250 below a terminator 251 is imaged through the lens L of the myope. This produces in accordance with the myopic deficiency of the eye E an image of the knife edge K' in front of the retina plane R.

Viewing the respective points on which an image of the knife edge terminator 251 can be projected through 3 points on the eye can be instructive. First, and through the central portion of the eye, 262, it will be seen that the illuminated knife edge 250 will be projected on the retina through an enlarged illuminated area 262'. Secondly, the same knife edge when projected through point 261 on the eye will be projected through an additional and enlarged area 261'. Finally, projection through point 263 will produce an enlarged image 263'. Thus the total image will be spread over an enlarged area of the eye, which area of the eye must then, in accordance with the limitations of knife edge imaging, be viewed over the top of the knife edge terminator 251. This will be the portion immediately over the terminator 251.

Constructing a straight line from point 261 to and across the image of the knife edge to retina of the eye, one immediately can determine a terminator of that portion of the retinal plane which may be viewed. Constructing a terminator of the viewed area over the knife edge, one can project an image of the terminator at 252'. Constructing terminators from point 263 through the terminator image 252' to the retina gives a window through which light impinging on the retina may be returned immediately over the knife edge K.

It will be appreciated that the terminator of the image on the retina will be indefinite and out of focus. As correction is made to the eyes of the myope through intervening optics, the image K' of the knife edge will approach the retina R of the eye. As it approaches the retina R of the eye, the terminators will sharpen. When the terminators sharpen, the unexpected result of utilizing the displacing lens to project light to the eye and receive light back from the eye will be enhanced with the sharpness of the image terminator.

In encountering these respective segments A1, C+, C− and A2, the light will be deflected as it passes immediately over the edge of the knife in the patterns previously described with respect to FIGS. 8A and 8B. The light will attempt to generate a square pattern on the lens L of the eye E and finally pass to the retina of the eye R where the myopic condition is illustrated.

Knife edge tests even through a specialized element such as the element V have one thing in common. This factor is that light returning to a knife edge always returns to a spot immediately adjacent the light area from which light was originally emanated assuming a moderate state of refractive error. Thus in the illustrated case, light emanating from the illuminated edge of the knife (the reverse edge in the illustration of FIG. 10B) will return to the knife edge K at a position immediately above C+. The light will pass through the particular lens segment $A_1$, C+, C−, or $A_2$.

Observing further the diagram of the myopia illustrated in FIG. 10B, we know that the light incident upon an area 24' will return from an illuminated area 24 from the lens L of the eye E. It will return and again receive an upward deflection. When it receives this upward deflection, it will pass to a detector.

Two effects will occur because of the passage of light to lens L of eye E through the specialized lens V.

First, rays deflected by the elements of the lens V to any portion of the eye other than the upper portion 24' *will never be seen.* Thus, the total amount of light received back from the knife E over the top of the knife edge will be diminished; only those rays which are emanated to the upper portion of the eye will have enhanced reception upon their return.

Secondly, and since in knife edge testing of the eye rays return from diametrically opposite portions of the eye, light rays will have a greater total deflection when received back from the eye.

There results an image of increased deflection with increased contrast.

Another way to understand this aspect of my invention is to analyze the case of parallel rays sequentially left to right leaving the knife edge. Upon passing through the specialized lens or "wobble plate" V, all the parallel rays will be sprayed in patterns, which patterns have been previously illustrated. Only that portion of the pattern which is sprayed to the upper portion of the eye L will be seen over at the corresponding point along the top of the knife edge K upon return. Moreover, the portion that is returned will be returned from the lower segment of the eye 24 and have a second deflection upwardly upon passing by the knife edge K for the second time. This second deflection when received at a photodetector such as that illustrated in FIG. 11 will give enhanced contrast through enhanced light ray displacement in analyzing the resultant image.

Review of the images returned from the eye by other optical defects is analogous. In each case, the light that can be accepted from a knife edge test enters the eye at one portion and exits at a diametrically opposite portion. It can therefore be seen that the enhanced deflection principle above-entitled will work for all vision defects. For example, in the case of "farsightedness" illustrated in FIG. 1E, light entering the bottom portion of the lens 23' will exit the top portion 23. Likewise and with respect to FIG. 1G, light entering the lefthand segment of the lens L at 36' will exit area 36. The resultant enhanced deflection will be the same.

Referring to FIG. 11, the specialized lens V of this invention is shown placed over a detector aperture 200. Aperture 200 is surrounded by four knife edge pairs, the respective knife edge pairs being denominated by the designations A, A', B, B', C, C' and D, D'.

Observing these knife edges placed in a square pattern about detector aperture 200, it will be noticed that only the light emitting apertures A, B, C and D are immediately adjacent the detector aperture 200. These light sources having their knife edge adjacent the aperture 200 form the four knife edges previously illustrated.

It has been found in addition to the retinal reflections observed, there will be certain corneal and iris reflections going back to the detector $D_1$. If only one side of the detector aperture is illuminated, one knife edge will have the effect of weighting the image received at the detector segments $D_1$, $D_2$, $D_3$, $D_4$. Since this is the case, it has been found expedient to illuminate the knife edges in pairs. Thus when knife edge segment A is illuminated, segment A' is also illuminated.

Regarding segment A', it will be noted that it is separated a distance from the knife edge formed by light element C. Since it is separated by the width of the element C from the detector aperture 200, substantially no light will return from source A' due to the retinal knife edge effect. The only light that will return will be that light which is from other reflected sources, such as corneal reflections, iris light, and the like. In order to relay light from the knife edges and to the eye, and from the eye to the detector, a lens 203 may be optionally placed between the light sources and eye.

In order to assure that the combinations of illuminated light sources A, A' contribute no weight to the overall displacement of the image, both light sources are given an effectivity which is symmetric to the center of the light-receiving aperture 201. In order to do this, light source C is given an intensity slightly greater than light source C'; this intensity is such that the product of the distance from point 201 to light source C equals to the product of the distance from point 201 to light source C'. Naturally, the same illumination scheme is utilized in light sources B, B'; C, C'; and D, D'.

Relay of the image to the eye E is shown occurring via a lens 203. This relay system is only schematically illustrated. Any number of relay systems can be used.

It will be observed that each of the light sources A–D' is covered with a portion of a lens. Preferably, the cylindrical lens is given a focal length so that in combination with the other optics, the knife edge is projected to the retina R of the eye E. Light returning from the faint image of the retina R of the eye E will pass through the lens element V, the detector aperture 200 and to and on the detector segments $D_1$–$D_4$ previously described.

Referring to FIG. 12, a preferred embodiment of my objective refractor is disclosed. According to this embodiment a wobble plate W is illustrated overlying not only the detector aperture 200 but additionally each of the light sources as well. Resultant deflection from each knife edge occurs as it is illustrated schematically with respect to FIG. 10. Thus, each of the four knife edges has an optical pattern imaged to the eye and each of the optical edges in return passes light to the detector segments $D_1$–$D_4$ in the manner previously illustrated. It can be thus seen that the plate W herein can be operable either over that portion of the knife edge emitting light to the eye, that portion of the knife edge receiving light from the eye, or both (as illustrated in FIG. 12).

During the development of this invention, I have made a surprising discovery. Specifically, I have determined that any optical element composed of cross cylinder lenses is sufficient for the practice of this invention. I have further determined that the cross cylinder lenses can be formed from any repetitive combination of cylinders including the case where the cylinders are positive and positive, negative and positive, positive and negative, and/or negative and negative. Specifically, and with respect to matrices composed of negative lenses, I find these to be a preferred embodiment, especially if they are placed in a random pattern with respect to the knife edge.

I have further determined that other optical surfaces will work for the distribution of light. So long as the light is evenly distributed from a central detector position to all detector quadrants and light is proportionally moved between the detector segments with detected image movement, an optic element containing multiple deflecting facets will work.

By use of the word optic, I intend to cover both mirrors and lenses. By use of the word deflection I intend to cover both refraction and reflection.

As examples of the diverse surfaces which may be used, cylinders, randomly aligned pyramids and the like may all be utilized as the deflecting surfaces.

Referring to FIG. 14A, I have caused a diagram to be displayed illustrating negative lenses. In the diagram of FIG. 14A, a schematic representation of lens surfaces similar to that representation contained in FIG. 4B is used. However, arrows 301-304 are utilized to illustrate the deflection of light at portions of each of the optical segments of each of the regularly placed lens elements. As before, the lens elements are labeled C+, C−, $A_1$ and $A_2$.

Examining each of the elements, it can be seen that with respect to the contiguous quadrants of each element C+, C−, $A_1$ and $A_2$, all of the light impinging upon contiguous or adjoining quadrants will be directed to the same detector quadrant. Thus, and with respect to the lower right quadrant of element C+, the upper right quadrant of element $A_1$, the upper left quadrant of element C− and the lower left quadrant of element $A_2$, all light impinging upon these elements will be deflected to the same direction. Moreover, it will be seen that the contiguous quadrants together define an area the equivalent of each of the lens elements and having its boundary described about deflection arrow 304. This area of common deflection has been commonly shaded. If one were to place the lenses of FIG. 14A over the detector segments of FIG. 15A, a light impinging upon that shaded area will be directed to quadrant $D_{IV}$ of the detector.

Similarly, and with arrow 303, all light will be directed to quadrant $D_{III}$; and with respect to arrow 302, all light within that quadrant will be directed to quadrant $D_{II}$. Thus it can be seen that from areas of the lens matrix having the same size and shape as each of the lens elements C+, C−, $A_1$, and $A_2$, all light falling upon contiguous quadrants of the lens elements causes all light to impinge upon the same detector quadrant.

I have discovered that the detouring of light at lens elements that are of all the same power can be utilized to detect low level light image displacement. Specifically, I have found that either positive cylinder lenses, negative cylinder lenses or astigmatic lens elements of opposite overall cross cylinder alignment can be utilized to generate the optic displacement utilized in my invention.

An example of this utilizing a negative lens element can be illustrated with respect to FIG. 14B. Referring to FIG. 14B, a series of negative lens elements C− are all illustrated in side by side relation. Lens elements C− can in turn be divided into quadrants. These quadrants labeled counterclockwise in accordance with the convention previously described for detector quadrants fall into subquadrants $Q_1$ deflecting light generally to the 10:30 counterclockwise position; $Q_2$ directing light to the 8:30 counterclockwise position; $Q_3$ deflecting light to the 4:30 clockwise position; and $Q_4$ directing light to the 1:30 clockwise position. Section $Q_1$ will be directed to the detector quadrant I, all light impinging on detector segment $Q_2$ will be directed to detector quadrant II, all light impinging upon detector segment $Q_3$ will be directed to detector quadrant III.

Attending to the schematic of FIG. 14B further, it can be seen that a knife edge $K_1$ laid out on a two to one slope will have equal portions of the knife edge passing to all segments of the detector. For example, referring to knife edge $K_1$ it can be seen that equal linear portions of the knife edge will be deflected by each lens quadrant to a particular detector segment. For example, comparing FIG. 14B and FIG. 15A and examining the knife edge $K_1$ from left to right, it is seen that a first quarter of the knife edge will be deflected to and across detector quadrant $D_{II}$. A second segment of knife edge $K_1$ will be deflected to and across detector quadrant $D_{III}$; the third segment of knife edge $K_1$ will be deflected to and across detector quadrant $D_I$ and finally the fourth segment of knife edge $K_1$ to and across detector quadrant $D_{IV}$. It can quickly be seen that equal portions of the knife edge $K_1$ will all go to different detector quadrants.

It will be recalled from the foregoing discussion that two respective rules have to be followed when faint images are detected by the detector of my invention. The first of these rules is that when a centered image is detected, light is equally distributed among all the quadrants. The second rule that needs to be followed is that when displacement of the image occurs, the light impinges with a weighted impact on the detector quadrants. In effect an indication of the displacement of the light is given by the distribution of light at the particular detector quadrants.

In actual fact, this is not the case with the regular lens elements illustrated in FIG. 14B. In place and instead of such a straight detection of the quantity of light hitting the photodiscrete segments, I have found it necessary to differentiate between the current at certain locations as compared to the overall light signal received on all four quadrants. This aspect of the invention will be discussed more specifically hereinafter with references to FIGS. 15A-15C.

I have additionally found that by passing the knife edge over a multiplicity of elements, the criticality of the oblique alignment of the knife edge with respect to the lens matrix generated is reduced. Referring to FIG. 14C, such an alignment of a knife edge is illustrated.

It will be remembered from the foregoing discussion that the knife edges when placed must follow two rules.

First, the edge of the aperture must traverse equal portions of each of the segments of the lens elements so that light from equal portions of the knife edge are all directed to separate detector quadrants.

Secondly, the knife edge must be disposed across the lens at a slope with respect to the boundaries of the lens elements and not parallel to these boundaries. A particularly preferred slope of two to one has been previously illustrated, the requirement there being present that the boundary traverse at least one set of four separate discrete elements.

Where the lens elements here illustrated are laid out in a regular side-by-side pattern with rows and columns of such elements occurring, it has been found that placing of the knife edges in alignment with the rows and columns, or precisely obliquely to the rows and columns results in a detector configuration which will not reliably measure the displacement of the images.

Referring to FIG. 14C, it can be seen that the knife edge can traverse large number of discrete elements and closely approximate the prohibited horizontal alignment described above. Specifically, and where multitudinous elements in a side-by-side array are all created, the angle of the knife edge can more closely approach the axis of a row or a column of discrete lens elements or alternately an oblique alignment of the elements without rendering the knife edge inoperative.

I have even found as illustrated with respect to FIG. 17, that the lens elements can be placed in side-by-side random alignment. With respect to such a random alignment where multitudinous lens elements are utilized with respect to each knife edge, I find that the distribution of light in equal proportion to each of the quadrants in accordance with the weighting of the overall image is closely approximated. Accurate measurement can occur with such a configuration.

Referring to FIG. 15A, I illustrate a detector quadrant with knife edge illumination falling on the quadrant with respect to knife edge $K_1$ as disposed across a lens element similar to that illustrated in FIG. 14B. It can be seen that the respective detector quadrants are labeled counterclockwise segment $D_I$, segment $D_{II}$, segment $D_{III}$ and segment $D_{IV}$. Likewise, it can be seen that the knife edge $K_1$ cuts respectively across segment $D_{III}$, $D_{IV}$, $D_{II}$ and $D_I$ in sequence. It will be noted that the detector quadrants are larger than the projected images from the knife edge. Specifically it is preferred if the detector area is four times the size of the image to prevent signal disparities due to image excursion beyond the photosensitive surface.

Displacement of an image in the X direction, however, from the configuration illustrated in FIG. 15A to the configuration illustrated in FIG. 15B produces an interesting result. Specifically, it will be immediately observed that with displacement merely in the X axis direction, the amount of knife edge in detector segments $D_I$ plus $D_{II}$ or $D_{III}$ plus $D_{IV}$ remains unchanged. However, this is not the case with respect to detector segments $D_I$ plus $D_{IV}$ or $D_{II}$ plus $D_{III}$. For example, the length of knife edge $K_1$ in detector segment $D_{III}$ is reduced. This knife edge segment appears instead at segment $D_{IV}$.

Displacement of the image in the Y direction from the configuration illustrated in FIG. 15A to the configuration illustrated in FIG. 15C likewise produces an interesting result. Specifically, it will be observed that with displacement merely in the Y axis direction, the amount of knife edge in detector segments $D_{II}$ plus $D_{III}$ or $D_I$ plus $D_{IV}$ remains unchanged. However, this is not the case with respect to detector segments $D_I$ plus $D_{II}$ or $D_{III}$ plus $D_{IV}$. Looking at the amount of light in each quadrant during the motion from the configuration in FIG. 15A to the position of FIG. 15C does produce some non-linearity. First, and during the first part of the motion, it will be seen that the amount of knife edge in quadrant $D_{II}$ reduces until all of the knife edge $K_1$ passes out of quadrant $D_{II}$ When this motion has occurred, the knife edge will then pass out of the detector quadrant $D_I$. There will be at detector quadrant $D_{II}$ no further light reduction. In short, there is a non-linearity resulting from the displacement in the Y direction for each quadrant seen separately, but the sums of $D_I$ plus $D_{II}$ or $D_{III}$ plus $D_{IV}$ behave in a linear fashion with translational motion in Y.

I have found that by differentiating the sums of total light received with respect to the light received at certain quadrants, a signal proportional to the displacement in the X and Y directions can be generated. For example, where displacement occurs in the X direction, I find that by the following formula a signal with respect to displacement in the X direction can be generated:

$$D_x = \left[ \frac{L_I - L_{II} - L_{III} + L_{IV}}{L_I + L_{II} + L_{III} + L_{IV}} \right]$$

Similarly, because of the non-linearity appearing in displacement along the Y axis as illustrated in FIG. 15C, I again have found that by differentiating certain of the segments with respect to the other detector segments in comparison to the total light received, a signal with respect to the Y axis displacement can be generated. Such a displacement can be obtained by the formula:

$$D_y = \left[ \frac{L_I + L_{II} - L_{III} - L_{IV}}{L_I + L_{II} + L_{III} + L_{IV}} \right]$$

where:
$D_x$ is the displacement in the X direction;
$D_y$ is the displacement in the Y direction;
$L_I$ is the light impinging upon quadrant I;
$L_{II}$ is the light impinging upon quadrant II;
$L_{III}$ is the light impinging upon quadrant III;
and,
$L_{IV}$ is the light impinging upon detector quadrant IV.

In the use of most objective refractors, there is a problem of positioning which is commonly encountered. Specifically, the eye must be acquired. Acquisition includes placing the eye in the proper alignment to the optical axis of the instrument or in what may be described as a "XY" positioning. Moreover, once the eye has been acquired along the optical axis, the towards and away position of the eye is important. For this aspect of the invention, a specialized aperture has been developed. Referring to FIG. 16A, a detector I had utilized with this invention is illustrated. Specifically, four prisms 401, 402, 403, 404 are placed in a square array. The prisms placed in their square array define a central square aperture 410 and four peripheral square apertures 411, 412, 413 and 414. Each prism has an opaque face and three beveled edges from which light is emitted. In the case of prism 401, there is an opaque face 400 and three light emitting edges 415, 416 and 417.

Each of the respective edges has a light emitting diode focused through a lens. The light emitting diode is focused through a lens and thence through the prism so that a greatly enlarged image of the light emitting diode is focused at the eye to be examined. In the case of prism 401, light emitting diode 405 is focused through lens 409 and has two refractions and one reflection from and within prism 401. These light deflections cause the light to be emitted from prism edge 415. Typically, the beveled edge of prism 415 is aligned so that the focused light emitting diode is directed to and upon the eye. Preferably, a "pebble plate" surface is added to the prism optics, preferably at the surface of first incidence of light into the prism.

Similarly, light emitting diode 406 focuses through edge 416, and a light emitting diode 407 focuses through edge 417. It will be understood that each of the respective prisms 402, 403, and 404 have a light emitting edge similar to those of prism 401.

All knife edges are preferably masked so that light incident immediately over them are passed to the detector and the remainder of the light is rejected. This masking is illustrated in the view of FIG. 16A.

It will be noted that the corners of the light emitting edges are masked. For instance in the case of prisms 401 and 402, it will be seen that the corners 420 are covered.

From the respective prisms, light is emitted to the eye to be examined, and returns from the eye being examined by way of projection optics which have been previously illustrated and are not shown here. The received light passes over the knife edge defined by the junction of the prisms and the apertures. The light then passes interiorly of a detector having the square aperture array previously illustrated. When passing interior of the projector, the light passes through the specialized lens element V (preferably the pebble plate illustrated hereafter in FIG. 17) and thence through focusing lens L to the detector D where an image K' is formed. Analysis of a knife edge image occurs.

Referring to FIG. 16B, a view of the imaging apparatus ratus of FIG. 16A is illustrated. Specifically, the detector is shown so that the light emitting edges may be viewed as they are seen from the eye of the patient being examined.

It will be noted that the light emitting edges 416 on one hand and 418 and 419 on the other hand are disposed along a top colinear horizontal edge of the detector. Edge 416 is equal to the lengths of edges 418 and 419 added together. Thus it may be fairly said that the two outside edges when added together have the same length as the inside edge 416.

It will be also noted that edge 416 points in opposite direction from edges 418 and 419. Thus, assuming that the edge comprising edge 416 facing in one direction and edges 418 and 419 facing in the opposite direction are illuminated, an eye will have equal and opposite refractive effects produced therein by the various edges. This is another way of saying that the edge effects will not comprise a weighted image giving a telltale indication of either spherical or cylindrical correction being required. In other words, illumination along a single edge with equal lengths in opposite direction will produce no detectable prescriptive correction.

Referring to the linear edge comprising the illuminated edges 426, 428 and 429, the same statement can be made. Since equal lengths of edge are illuminated in opposite directions, weighting of the images in the eye will not be detected. It can be shown, however, with respect to FIG. 16B that the sequential illumination of these respective images can serve to assist to position an eye.

Referring to FIG. 16C, a schematic diagram is therein shown. The schematic assumes that the eye is illustrated properly centered in the X and Y plane. Naturally, by measuring the image impingements on the quadrants of a detector $D_I$, $D_{II}$, $D_{III}$, $D_{IV}$, centering of the eye with respect to an optic axis can occur.

The question then becomes what is the proper positioning of the eye in the Z axis direction.

In the schematic of FIG. 16C, the respective light emitting edges are schematically shown. Specifically, edges 416, 418, and 419 are all illustrated. Similarly, lower edges 426, 428 and 429 are all illustrated.

It should be realized that FIG. 16C is a schematic. Focusing optics P schematically illustrate the convergence of the image from the edges to an active detector. The specialized optics V as well as the eye of the patient are all omitted.

In FIG. 16C, the images for each of the knife edges at differing distances are illustrated. Referring to the six detector images shown, the upper two images are for when the eye is at the proper distance from the detector. The middle image is an illustration of the detector when the eye is too close. The lower two pair of detector images are illustrations where the eye is too far away.

It will be understood that the right-hand group of images are the image that would be cast where knife edges 418, 416 and 419 are illuminated. The left-hand group of images are where edges 428, 426 and 429 are illuminated. Typically, these images would be produced with first one linear set of knife edges being illuminated and thereafter a second linear set of knife edges being illuminated.

Referring to the upper images where the eye is positioned the proper distance from the detector, it can be seen that the image formed by knife edges 418, 416 and 419 are the same as the images being formed by knife edges 428, 426 and 429.

Where eye is too close, the images formed by knife edges 418, 416 and 419 raise up on the surface of the detector. Great concentrations of resultant images appear at upper quadrants $D_I$ and $D_{II}$. The effect on the image of knife edges 428, 426 and 429 is the opposite. Specifically, the respective images of the knife edges fall in greater measure on quadrants $D_{III}$ and $D_{IV}$.

Typically, the knife edges of the detectors are either modulated with their own discrete signal so that the images can be separated one from another, or are alternately illuminated. In either case, the resultant weighting of the detector signal at the quadrants of the detector gives an indication of the towards and away position of the eye (not shown).

As can be seen in the lower illustration, where the eye is too far away, the effects are reversed. Specifically, for knife edges 418, 416 and 419 the image shifts downwardly. Specifically, the image shifts to detector quadrants $D_{III}$ and $D_{IV}$.

For the knife edge image of knife edges 428, 426 and 429, the effect is reversed. The knife edge shifts upwardly to detector quadrants $D_I$ and $D_{II}$.

It will be observed that the particular knife edge images cast are symmetrical. That is to say, they are equally weighted about a center line. This is because the knife edge images oppose one another for equal lengths. Consequently, it will be appreciated that the particular knife edge images cast are insensitive to the particular optical prescription that may be encountered in the eye.

Thus, it can be seen that the image produced is insensitive to the prescriptive effects the eye might have but is sensitive to the positional effects that the eye imparts in being acquired by the instrument.

Assuming that the eye is properly acquired, the measurement of the eye then occurs by illuminating light knife edges disposed along the same direction but at varying positions. A knife edge examination utilizing only one such group of knife edges will be illustrated, the knife edge examination of other edges being analogous and easily understood.

Referring to the schematic of FIG. 16D, a typical knife edge test is illustrated. Specifically, knife edges 416, 428 and 429 are all illustrated. The knife edges are illustrated passing through projection optics P to a detector consisting of detector quadrants $D_I$, $D_{II}$, $D_{III}$, and $D_{IV}$.

First, it will be noted that all of the knife edges 416, 428 and 429 are addressed in the same direction. As they are addressed in the same direction, the resultant image produced by an eye will be knife edge sensitive as to the prescriptive correction required. This being the case, and assuming that we have an emmetrope, the detector segments illustrated will be a minimal image. As the respective knife edges are spaced evenly about the central axis of the optic instrument so as to produce a centroid of illumination evenly about the optic axis of the instrument, the measurement system will have its position sensitivity minimized. That is to say, its position sensitivity to the positioning of the eye within the instrument would be minimized.

In accordance with the previous illustrations rendered, the hypermetrope will produce an image on one side of the detector, say detector quadrants $D_I$, $D_{II}$. Similarly, the myope will produce an image on the opposing quadrants $D_{III}$, $D_{IV}$. Finally, an astigmat will have an image on the quadrants on one side or the other side, the image here being shown on quadrants $D_{II}$, $D_{III}$.

As will be realized by those having skill in the art, the edges of the detector can be switched. They can be switched so that images opposed to those illustrated can next be taken. This gives the instrument the desired push-pull effect. Moreover, it can also be realized that the imaging can be accomplished left and right. That is to say, a measurement can be taken using a group of edges on the left and then an opposing group of images on the right.

It will be realized at this point that the light emitting diodes can be modulated as can the detectors utilized with them. Specifically, the measurements can all be taken simultaneously with the modulated signals received back from the eye segregated. Moreover, by using a central and visible target for fixation, focusing of the eye to a visual target may result. This focusing of the eye can then have the disclosed objective refraction superimposed thereon.

As to the particular imaging scheme chosen, it should be understood that the edges are all active and given a common centroid. Thus when they fall upon the detector D, they fall upon each of the quadrants with equal intensity. Referring to the view of the optical train shown in FIG. 6E and the corresponding image of the detector shown in FIG. 6F, the balancing of the specular reflection image with respect to the alignment of detectors utilized to measure the prescriptive effects of the light is illustrated.

Referring to FIG. 16E, an eye E has three sources A, B, C imaged thereon. Images of these sources are relayed by optics (not shown) to three real image locations. These image locations are $K_a$, $K_b$, $C_C$.

Image $K_a$ is above the optical axis and twice as long as respective images $K_b$ and $K_c$. An image of these respective optics is relayed through the specialized optics V to the detector D. Specialized optics V has been previously described.

Referring to FIG. 16F, the centroid of light on the detector D is illustrated. This centroid is for specularly reflected light and does not incorporate any prescriptive corrections.

It can be seen that each image is off-set from the optical axis. Specifically, it is off-set by a given amount. Thus, if the detector D is either too close or too far away, the respective movements of the image from each of the light sources will remain the same.

Referring to FIGS. 16G and 16H, it can be seen that this is not the case where a single knife edge is utilized. In FIG. 16G, a pupil with a single light source A has the image thereof broadcast onto a specialized optical plate B at the illustration knife edge $K_A$. The knife edge $K_A$ is therefore relayed by optics not shown to the detector plane.

Assuming that the detector plane is at the right distance from the eye, the image will impinge upon the center. However, if the eye is either too far away or too close, the image will move. Specifically, it will move off center. In FIG. 16G, the image of a pupil moved away from the center of the eye is shown.

Referring to FIG. 16H, an on-center image is illustrated. It can be seen that the light centroid is off-center with respect to the detector quadrants $D_I$, $D_{II}$, $D_{III}$, and $D_{IV}$. In actual fact, the migration of the image has occurred from the two upper quadrants $D_I$, $D_{II}$ to and towards lower quadrants $D_{III}$, $D_{IV}$.

Returning to the three detector array shown in FIG. 3 and taking the case of the non-specularly reflected light, the action of the towards and away positioning of the optics here illustrated can be illustrated.

Specifically, and if detector D is at the position $D_1$ with respect to specialized optics V and the images $K_a$, $K_b$ and $K_c$, it will be seen that all images will be broadcast into substantial coincidence. That is to say, they will be imaged upon a central point of the detector D.

If, however, the detector is too far away such as at position $D_2$, three such images will result. These three such images are illustrated in FIG. 16L.

Referring to FIG. 16L, and taking the case of a myope, it can be seen that the three images are produced. The lower image $I_a$ will be twice as intense as the two upper images $I_b$ and $I_c$. These images $I_b$ and $I_c$ will all be displaced in accordance with the particular prescriptive correction of the eye being required. This being the case, and reviewing the images heretofore discussed, it will be seen that the displacements will add in all detector quadrants $D_I$–$D_{IV}$ to give the same result as the single image shown in FIG. 16K. Consequently, it will be realized that the detector scheme herein illustrated is insensitive to towards and away positioning of the eye with respect to the apparatus.

It will be understood that with this explanation an immediate process can be added. First, axial towards and away alignment such as that illustrated with FIG. 16C will be undertaken. Thereafter, and once the eye is grossly in place, prescriptive measurements will be made. These measurements will be made by apparatus illustrated in accordance with FIGS. 16J, 16K and 16L. Thus, even though once the eye is properly positioned and the eye wanders somewhat from its original positioning, the disclosed optics will be relatively insensitive to such movement. Correct objective refraction will result.

Regarding specular reflection, and referring to the view of FIG. 16F, it can be seen that the areas of the light sources are important. Specifically, by having the moment of optical areas the same above and below the horizontal axes as well as the moment left and right of the vertical axes being the same, specular reflection from the eye will cancel itself among the various detector segments. Consequently and with the edge arrangement shown, perturbation of the refractive findings by return specular reflection cannot occur.

Referring to FIG. 16J, an alternate dimension of the knife edge configuration is illustrated. Specifically, each of the knife edges $K_a$, $K_b$, $K_c$ are of the same length and area. These respective knife edges are separated from a horizontal axes by two units of distance in the case of the knife edge $K_a$ and one unit of distance in the case of the knife edges $K_b$, $K_c$. The unit of distance are all labeled with $2a$ for knife edge $K_a$ and for knife edges $K_b$, $K_c$. The knife edges are all of the same length. Specifically, the knife edges are labeled with the width dimension $b/3$.

Referring to FIG. 16L, the unfocused centroids of the image are there shown. Specifically, it can be seen that the lower image $I_a$ is displaced from the horizontal axes by an amount approximately twice the centroid of the two upper knife edge images $I_b$, $I_c$. Perturbation of the refractive signal due to axial or towards and away displacement will not occur. It should be pointed out that for best performance, the light receiving or viewing apertures adjacent to knife edges should also have substantially equal moments above and below the horizontal axis as well as left and right of the vertical axis.

Turning attention to FIGS. 18A-D, these figures illustrate the patterns which form on the detector due to a decentered pupil with an arbitrary refractive error (sphere plus cylinder at a tilted axis to the knife edge).

FIGS. 18A and 18B illustrate horizontal knife edge interrogation. The knife edge K in FIG. 18A is disposed so that light passes to the receiving area 400 below the knife edge K and over the linear boundary 415. Likewise, in FIG. 18B, an area 402 receives light immediately above the knife edge 415. With respect to FIG. 18C and 18D, the knife edges are vertically disposed. The edges there respectively are to the left of and to the right of the detector surfaces. Areas 404 and 406 receive light in FIGS. 18C and 18D respectively.

Each of the FIGS. 18A-18D has schematically illustrated next to the respective knife edges the detector surface. The detector is that detector illustrated previously.

In the case of the image illustrations herein given, it will be understood that the light is distributed to the detector plane by the preferred optics show herein. Thus, the light received at the detector plane will not have the appearance schematically illustrated on the detector surfaces of FIG. 18A-18D. Instead, the light will be evenly distributed among the detector quadrants as previously set forth.

In each case of FIGS. 18A-D, the detector measures two values which are proportional to the X centroid position times the total received light flux and the Y centroid position times the total received light flux. Since the total flux is the same for both values, the values are in fact proportional to the X and Y centroid positions.

In addition, it will be appreciated the source and detector array are designed so that each knife edge has equal values for total light and in fact is symmetrical in all respects about the pupil image center on the detector. Thus, the measured values can be added and subtracted in a method which will now be given so that both refractive information and pupil decentration information can be extracted.

Note in FIG. 18A $$X_{CA} = R_{XA} + X_P$$

$$Y_{CA} = R_{YA} + Y_P$$

where
$X_{CA}$ = X centroid position
$Y_{CA}$ = Y centroid position
$R_{XA}$ = X displacement of centroid from pupil center
$R_{YA}$ = Y displacement of centroid from pupil center
$X_P$ = X position of pupil center
$Y_P$ = Y position of pupil center
Similarly and in FIG. 18B, $$X_{CB} = X_P + R_{XB}$$

$$Y_{CB} = R_{YP} + Y_P$$

Due to the pattern symmetry set forth above,
$R_{XB} = -R_{XA}$
$R_{YB} = -R_{YA}$
So;

$$X_{CB} = X_P - R_{XA}$$

$$Y_{CB} = -R_{YA} + Y_P$$

This means then;

$$X_{CA} X_{CB} = X_P + R_{XA} + X_P - R_{XA} = 2X_P$$

measured values $$Y_{CA} + Y_{CB} = Y_P + R_{YA} + R_{YA} + Y_P - R_{YA} = 2Y_P$$

This shows that the measured values can be added, X to X, Y to Y, to yield values which are directly proportional to pupil decentration. Note that prescriptive information is not included.

Likewise:

$$X_{CA} - X_{CB} = X_P + R_{XA} - (X_P - R_{XA}) = 2R_{XA}$$

$$Y_{CA} - Y_{CB} = Y_P + R_{YA} - (Y_P - R_{YA}) = 2R_{YA}$$

which shows that a correct subtraction of measured values yields values which are directly proportional to the displacement of the centroid of the received pupil pattern from the pupil center. In addition, because these values are X and Y displacements of the centroid, they yield both magnitude and direction of this displacement which in turn are directly related to refractive error as previously set forth at length in this application.

It has heretofore been mentioned that, in this application, one parallel set of knife edges cannot provide complete refractive information (although it does give decentration of the pupil). However the remaining information is collected via the second parallel set of knife edges as shown in FIGS. 18C and D. Note that in all figures the relative position of the pupil center to detector center is the same.

In summary, by adding all X centroid values a value proportional to X pupil decentration is obtained. By adding all Y centroid values, a value proportional to Y pupil decentration is obtained. By correctly subtracting values of parallel knife edge pairs, four refractive proportional values arise, namely;

$$X_{CA} - X_{CB} = 2R_{XA}$$

$$Y_{CA} - Y_{CB} = 2R_{YA}$$

$$X_{CC} - X_{CD} = 2R_{XC}$$

$$Y_{CC} - Y_{CD} = 2R_{YC}$$

Then it is found that values proportional to sphere equivalent ($S_{eg}$), cross-cylinder axis 90°/180° ($C_+$) and cross-cylinder axis 45°/135° ($C_x$) can be obtained by combining the refractive proportional values in the following manner:

$$S_{eg} \sim R_{XC} + R_{YA}$$

$$C_+ \sim R_{XC} - R_{YA}$$

$$C_X \sim R_{XA} + R_{YC}$$

where
$C_+$ is 0°–90° cylinder, and
$C_X$ is 45°–135° cylinder.

It will be appreciated that the detector disclosed herein can be utilized to have refracting optics driven so as to null the received signals at the detector surface. I have demonstrated such circuitry before and hereby incorporate by reference as if fully set forth herein my prior U.S. Pat. No. 4,070,115. Specifically, that patent disclosed an invention which may be abstracted and summarized as follows:

A lens meter is disclosed in which continuously variable spherical and astigmatic corrective optics are manipulated to measure the prescription of a suspect optical system. A target including a straight line is focused for maximum clarity, the target being arbitrarily aligned without respect to the axis of the suspect optical system. Continuously variable spherical and first astigmatic optics are juxtaposed to the suspect optics and the image of the target projected through both the suspect optics and the continuously variable optics. Spherical and first astigmatic corrections along at least one axis diagonal to the line target is made until maximum sharpness of a projected image of the line results. A first component of astigmatic correction results. A second target, again consisting of a straight line, is introduced; this target is angularly inclined with respect to the first target preferably at 45°. Spherical adjustment is made together with a diagonally aligned second astigmatic correction along at least one axis diagonal to the second line target until maximum sharpness of the projected image of the line results. A second component of astigmatic correction and final spherical correction results. Provision is made for remote manipulation of the continuously variable optics to determine prescription automatically.

A representative claim of that patent application is included as follows:

1. A process for measuring power of a suspect optical system in at least one component of cylinder including the step of: mounting said suspect optical system in a light path; projecting light including an image of at least one first straight line target of first arbitrary preselected angular alignment without regard to any suspected principal axis of the suspect optical system along said light path; providing in said light path variable optics for movement to a power of sphere and cylinder substantially equal and opposite to components of sphere and cylinder in said suspect optics, said variable optics including variable spherical optics to vary the spherical component of light projected there through and variable cylinder optics for varying the astigmatic lens power along first intersecting diagonals at substantially equal and opposite angles from the preselected angular alignment of said first straight line target; projecting an image of said straight line target from said light passing through said variable optics and said suspect optics; and, varying said spherical optics and said first astigmatic optics to optimize the image of said projected straight line target.

Referring to that application at FIG. 5, sufficient schematic circuitry is given from a detector having four distinct quadrants to drive optics to achieve a null image. While adaptations must of necessity be made to produce the detector configurations herein set forth, it is believed that such changes may be easily be made by those having ordinary skill in the art. Lenses schematically achieving such a null image are shown in FIG. 16G as variable spherical lens 516, 0°–90° cylindrical lenses 578 and 45°–135° cylindrical lenses 520. These lenses are taken directly from FIG. 5 of the referred to by reference patent.

It is a particular advantage of my invention that refractive information returned from the eye is not dependent upon the ability of the eye to return light to the detector. Take the case wherein a retina, through disease, has enlarged blood vessels, and/or other configuration. Consequently the retina is not capable of uniformly returning light to the detector over its surface. In such cases, the light received back by one of the knife edges in FIGS. 18A–18D will substantially differ from the light received by other knife edges. By the expedient of mathematically equating all of the returned light—giving the quantity of returned light in each knife edge alignment of FIGS. 18A–18D the same value and thereafter processing the values, the effects of irregularities in the retina may be ignored.

It will be noted that in the previous description and equations relative to FIGS. 18A–18D, I have effectively illustrated "moments" of the light flux with respect to the particular detector quadrants utilized. Thus, when the term "moments" is used heretofore or hereafter in this application, it should be so understood.

It will be understood further that for the best performance, the apertures herein utilized should be symmetrical. Moreover, the areas of the apertures and the receiving areas should all have equal moments.

Although the point has heretofore been made, it should be emphasized that in the case of the knife edges, disposition at right angles is not required. For example, the knife edges could be disposed at 45° angles. Moreover, and with variations to the mathematics herein disclosed, and/or optics detector surfaces or both, varying angles could be used between the interrogating knife edges. I have merely illustrated the preferred parallel and opposed knife edges in symmetrical alignment to set forth the preferred embodiment of my invention as known to me at this moment.

Since the original filing of this invention on Oct. 31, 1980, the inventor herein has developed the disclosed invention into a preferred embodiment which will be vended after the date of the filing of this application. In order that this application may demonstrate how in fact the invention herein has been incorporated into this instrument, FIGS. 19, 20 and 21 as well as the additional portions of this application has been added.

Referring to FIG. 19 of this invention, the eye testing instrument of this invention is shown enclosed within housing H. Specifically, a patient P is shown in addressing an instrument housing including base 500 and head 502. Protruding from the head 502 is an altazimuth mounted interrogating head 503. The altazimuth interrogating head is mounted in disposition at all unlike that mounting described in my co-pending U.S. patent application for Keratometer; Serial No. 158,849 filed June 12, 1980. In that patent I set forth a system of an altazimuth mount including provision for side-to-side movement, towards and away movement, and movement in elevation. A chinrest and forehead rest assembly is illustrated. The interrogating instrument is capable of addressing one eye or the other eye of the patient P for the desired objective refraction.

Typically, the instrument is equipped with a light emitting diode or liquid crystal readout 504 and various controls 506 for the positioning of the instrument. An eye chart 510 complementary to an eye chart interior of the instrument is visible to the instrument operator. Thus, when the objective refraction has occurred in accordance with this invention, the patient can first repeat the viewed eye chart. As is standard practice, the interrogating physician, either through memory or by reading eye chart 510, verifies the visual acuity of the patient in observing the unknown sequence of letters of the eye chart.

Referring to FIG. 20 the Badal type optical train used in the interior of the instrument is illustrated. The eye E of a patient P (the patient not being shown) is placed directly in front of eye piece 530. The eye piece 530 addresses a roof mirror 540 movable by a screw driven shaft 541 having a threaded follower 542. Shaft 541 is driven on bearings (not shown) by motor 543 in response to the sensing of images here and after to be described.

Roof mirror assembly 540 consists of two mirrors at right angles. These respective mirrors are mirror 545 and 546. These mirrors change the effective spherical power of eye piece 530 while the image of any optical target remains with its size unchanged image. An aerial image, is formed by relay lens 550. The aerial image can be considered to be the image of either the visual acuity target or the source/detector knife edges in the case of light traveling to the eye. In the case of refracted light returning from the eye, an aerial image is formed by the eye piece 530 and relayed to the detector assembly by relay lens 550. Light is directed to or from relay lens 550 by a roof mirror assembly comprised of mirrors 552 and 553. Thereafter the light passes through paired counter rotating cylindrical lens assemblies or astigmats 562, 563. These astigmats are paired counter rotating cylindrical lenses of opposite power. The axial mid-point of astigmats 562 and 563 is located one focal length of relay lens 550 from that lens thereby creating a second Badal system consisting of the astigmats 562 and 563 and the relay lens 550. The relay lens 550 can be considered to create an image of the astigmats 562 and 563 at optical infinity which is then re-imaged by eye piece 530 at a distance from it equal to its focal length. In this imaging all the optical properties of the astigmats 562 and 563 are also imaged in this plane and as the effective sphere power created by the first Badal system also occurs in this plane, a complete sphero-cylindrical correction is thereby created in a single axial position. This method of relaying the optical properties of a lens system is fully set forth in my William E. Humphrey, U.S. Pat. No. 3,874,774 entitled "Eye Test Apparatus." Neglecting beam splitter 564, the path of interrogating infra-red light hence passes from detector 570 to the eye E.

Where visible light is used, beam splitter 564 periscopes light to a second periscope mirror 575 which passes to an optical projector mechanism 580 (schematically shown). Optical projector 580 includes a projecting element and circular film for displaying sequential lines at least equivalent to those on eye chart 510 to the eye E of the patient.

It will be understood that in objective refraction, light first passes from detector 570 to the eye E in the infra-red. Thereafter, the infra-red light returns from the eye to the detector head 570.

Applicant will now discuss what has proved to be the preferred embodiment of the detector head. This discussion will be confined to the schematic of FIG. 21. Thereafter and with respect to the graph of FIG. 22 and the optical schematic of FIG. 20, acquisition of the eye and finally objective refraction of the eye will be set-forth. Finally, that amount of optical adjustment required for viewing of the optical path along the instrument axes will be discussed.

Referring to FIG. 21, a detector head similar to that disclosed in FIG. 16A is illustrated showing only the forward knife-edge portion. It will be noted that only four knife-edges are now used in the interrogating head of this commercial embodiment.

This illustrated detector head of FIG. 21 is a compromise in optical design. Regarding this compromise it will be appreciated after careful analysis of FIGS. 16A and 16F that as to specularly reflected light back from the eye, a slight error in balance will occur in the instrument. However, I have found this configuration to be more efficient in at least four other aspects.

First, the respective prisms 610, 611, 612, and 614 are easier to make.

Secondly, this embodiment only uses eight infra-red light sources instead of the twelve sources illustrated in FIG. 16A.

Thirdly, the respective interrogating knife-edges are all closer to being on axes. None of them are off axes by the large amounts in FIG. 16A.

Having set forth the configuration of the optical train in FIG. 20, attention now can be directed to the operation of the disclosed apparatus.

First, overall gross instrument movement in both the roof mirror assembly 540 and the paired astigmatic lenses 562, 563 occurs. This movement occurs until the instrument reaches an overall infra-red null.

Once an infra-red null is obtained, the knife-edges thereafter interrogate the eye using the disclosed interrogating sequence. This interrogation occurs with smaller and more precise movement of the roof mirror 540 and the astigmatic lenses 562, 563. This sequence occurs until the instrument at the detector head 570 detects an optical null. This results in the instrument determining the infra-red prescription for the eye.

Once the infra-red prescription for the eye is determined, the instrument thereafter readjusts to optical wave lengths.

Discussing the instrument manipulation sequence in detail and referring to FIG. 19, the patient P is placed with the forehead against headrest 507 such that the eyes are in positions E1 and E2. The operator typically aligns the instrument via a control 508 to coincide to the eye being examined.

Once the instrument grossly acquires the eye, gross movement is undertaken. Movement in azimuth and elevation occurs until the retro-reflection from the eye is roughly centered in the detector. Z movement or towards and away movement of the instrument from the eye occurs as illustrated in FIG. 16C and 16G, it being remembered that only two opposing knife-edges interrogate the eye.

In FIG. 22, I plot the intensity of the signal received as the eye is initially acquired vs the magnification. This intensity be seen to have the shape of an overall sine curve. However, it is the characteristic of my detector that the "sine" curve only includes one cycle of a typical sine curve. At either extreme of the sine curve, the received light asymptotically approaches the abscissa.

Furthermore it will be apparent that where anything other than the optical null is detected, the direction of movement of the roof mirror assembly 540 to acquire the eye is known. However, such movement can never be quantified in that there are two possible magnitudes of the optical null 670. For example, a first magnitude 671 and a second magnitude 672 will produce the same signal result. Therefore although the direction of movement is known, the amount of movement required can only be determined after some movement has occurred.

Assuming that panning movement occurs and the eye is acquired, iteration of first the lense elements in sphere and thereafter the lens elements in cylinder occurs all controlled by the detectors. Specifically by balancing all of the detector elements so that equal intensity of light are received on all detector quadrants the infra-red prescription is determined.

When the instrument reaches an optical null, it is with reference to infrared light. As the final prescription must be with reference to visible light and as the instrument's optics must be set to this prescription so that the eye can clearly see the acuity chart, a correction must be made to the lens settings formed in the nulling procedure. To find the proper correction two separate problems need be addressed.

The first problem is the effect of the chromatic aberration of the eye. If visible and infra-red light both enter the eye with same optical accommodation, the visual light will focus long before the infra-red light. It will be remembered in the instrument herein used, the infra-red light was focused upon the retina in the original refraction. Thus the eye will be myoptic in the visible.

Additionally, the reference plane of the infra-red used by the instrument to detect the null will undoubtedly be different from the plane of the visible light receptors in the eye. That is to say, infra-red light is imaged against the back of the eye. The plane wherein the imaging occurs may or may not be the coincident to the sensing rod and cone cells of the eye. This problem, common to many objectives refractors, can readily be corrected if movement to a visible target immediately occurs after objective refraction.

Stated in other terms, if the vergence of the infra-red light is known for a particular eye E, a correction must be applied to get the vergence of the eye.

If $P_{IR}$ is known, where $P_{IR}$=infra-red power $$P_{visible\ correct} = P_{IR} - \Delta$$

Note that the term $\Delta$ is variable. It is variable between individuals due to anatomical differences. However, since the total power of the eye is large in the order of 58 diopters, the necessary correction for any given eye between the infra-red and the visible range is on the order of 6 diopters. In general it can be seen the risk is about 10% of the total power of the human eye. Since the overall power of the eye—58 diopters—does not vary by a large percentile in the population, a constant correction factor can be used. We have found that the correction for refraction in the infra-red can be measured for the human eye to be between 0.6 diopters and 0.7 diopters. By using constant correction for all eyes, we have found that a satisfactory result is obtained.

The second correction is more difficult. This correction involves determining the value of the power difference between the infra-red and visible in the optical train. Basically it is a calibration problem.

Referring to the FIG. 20, if the instrument were to be calibrated so that it read out in the infra-red correctly, the infra-red prescription would be directly measured. However, it is much more convenient to calibrate the instrument with visible light and to have it read out in setting of its optical elements in terms of power in visible light. To reach this result a conversion is needed between the visible light setting of the instrument and the infra-red setting of the instrument.

The variable sphere power is created by moving an image of the detector/source array with respect to the eye lens. A moving mirror system consisting of the roof mirror 540 is used. If the position of the mirror (and enhanced image) is referenced to the position which creates zero power in the infra-red, the following equation relates to image position to power created $$P_{IR} = F_{IR}^2 dt$$

where:
$P_{IR}$=infra-red power
$F_{IR}$=power of the eye lens w.r.t. infra red light
dt=image power w.r.t. 0 power.

It will be recognized that $F_{IR}$ is a fixed quantity. It is the determined power in the infra-red.

The term dt can be obtained as follows. The mirror position for zero power in the visible is in general different than that for zero in the infra-red. This difference in position results because the visible target, against which calibration is done, is in general not coincident with the infra-red position. When collimated infra-red light from the detector exits the eye lens, collimated visible light from the target does not also exit the eye lens. In general a difference is created in the design of the instrument.

However it is possible to measure or to calculate from the design. The visible power created when there is zero power in the infra-red can be determined. This power is designated $P_0$.

The power created in visible light is related to the mirror position. This relation can be expressed as an equation similar in form to that which expressed $P_{IR}$. This equation is $$P_v = F_v^2 dt_v,$$

where:
$P_v$=visible power
$F_v$=power of eye lens in the visible.
dt=position of the image of the visible target from the zero power position in visible.

Knowing $F_v$ and $P_v$ we can solve easily for $dt_{vo}$. Specifically, $$dt_{vo} = \frac{P_o}{F_v^2}$$

Since dt and dtv are measured on the same linear scale, we can write an equation relating the two. This equation is written and solved $$dt = dt_v - dt_{v_o}$$

$$dt = \frac{P_v}{F_v^2} - \frac{P_o}{F_v^2} = \frac{1}{F_v^2}(P_v - P_o)$$

Knowing now dt in terms of the measurable quantities $P_v$ and $P_0$, we can express $P_{IR}$ in the terms of the measureable quantities $P_v$ and $P_o$.

$$P_{IR} = \frac{F_{IR}^2}{F_v^2}(P_v - P_o)$$

We still need to know $F_{IR}$ and $F_v$. $F_{IR}$ can be measured $F_v$ is related to $F_{IR}$ by the equation $$F_{IR} = \frac{1 - n_{IR}}{1 - n_v} F_v$$

where:
$n_{IR}$ = index of refraction in the infra-red
$n_v$ = index of refraction in the visible.

It can therefore be seen that solving the previous equation for $P_{IR}$ $$P_{IR} = \left(\frac{1 - n_{IR}}{1 - n_v}\right)^2 (P_v - P_o)$$

This equation solves the second part of the problem. Using representative contants for Bk-7 glass, a product of the Schott company of Duryea, Pa., the value given for the index of refraction $N_v$ at 587 millimeters in the visible range is 1.517. The value of the index of refraction for same glass in the infra-red 880 millimeters band is 1.508. So correcting, the power is P correcting = $0.965(P_v - P_o) - \Delta$ Since $P_0$ and $\Delta$ are constants, they can be lumped into a single constant giving the formulae and simplified equation P correcting = $0.965 P_v - K$ where $K = 0.965 P_o + \Delta$ Having derived the amount of movement required, a small and proportional movement of both the roof mirror and the astigmatic lenses can be generated. The small and proportional movement occurs immediately after the prescribing infra-red iterations of the instruments. Thus the instrument immediately moves to and toward the visible optical prescription.

It will be apparent that it may be desirable to provide for small adjustments once the eye is viewing the eye chart in the visible range. This has been in fact added to the disclosed instrument.

The reader will understand that by providing an immediate and visible eye path to be objectively refracted in the infra-red, advantages result. For example, the objectively refracted subject can be asked to verify the determined prescription, at least roughly. Moreover, minute corrections can be made.

It thus remains to operationally connect photo detector 1120 to remote apparatus for actuating variable spherical lens pairs 1016 and variable astigmatic lens pairs 1018 and 1020 to cause remote movement of the lens pairs to determine remotely prescription of the suspect optics.

Photo detector 1120 is a TYPE 640 4-QUADRANT DETECTOR manufactured by Electro-Nuclear Laboratories, Inc. of Menlo Park, Calif. It consists of four sensitive quadrants on a single wafer. This wafer is capable of producing differential output signal from its electrodes with the use of connected differential amplifiers. The differential output results when the image has differential illumination at the surface of the photo detector 1120.

Photo detector quadrants 1120c and 1120d connect to an operational amplifier 1121 and connected amplifier 1122. Power from amplifier 1122 is communicated through paired power leads 1124 to a motor 1125. Motor 1125 drives a gear 1126 which connects to a cam operated wheel 1130. Dependent upon the differential illumination at quadrants 1120c and 1120d, motor 1125 drives in a first direction of rotation or a second direction of rotation. As the parity of the photo detector electrical connections can be empirically determined by a skilled mechanic in the art, it will not be set forth here.

Photo detector quadrants 1120a and 1120b connect to an operational amplifier 1127 with a connected amplifier 1128. Power from amplifier 1128 is communicated through paired power leads 1130 to a motor 1132. Motor 1132 drives a gear 1133 which connects to a cam operated wheel 1140. Dependent upon the differential illumination at quadrants 1120a and 1120b, motor 1132 drives in a first direction of rotation or a second direction of rotation.

Switches 1142 are linked by a common toggle. Switch 1142 is closed when diagonal astigmatism (as in FIG. 3c) is measured and open when normal astigmatism (as in FIG. 3e) is measured. Conversely, switch 1145 is opened when diagonal astigmatism is measured, and closed when normal astigmatism is measured.

For the measurement of normal astigmatism, opening of switch 1142 closes switch 1145 through the common toggle. Switch 1145 through leads 1150 drives a motor 1155 and gear 1156 to rotate a cam operated wheel 1160.

Cam operated wheels 1130, 1140, and 1160 are known. Specifically, they are a component of a product known as "Vision Analyzer" manufactured by Humphrey Instruments, Inc. of Berkeley, Calif. Moreover, the operation of the cam operated wheel to effect relative lens movement of variable spherical or astigmatic optics is set forth in my copending patent application Ser. No. 624,808, filed Oct. 22, 1975, entitled "Eye Test Apparatus With Physician Routed Patient Input Adjustment to Variable Optical Elements", now U.S. Pat. No. 4,015,899, issued Apr. 5, 1977. The description of the operation of the cam operated wheels can be found in the text of the application related to FIGS. 1 and 2.

Broadly, as cam operated wheels 130, 140 and 160 are rotated by their respective motors 1125, 1132, and 1155, they cause variable optics B to relatively move. This occurs through cam and cable connections described in my copending patent application Ser. No. 624,808 and sold by Humphrey Instruments, Inc.

As can be seen, rotation of cam operated wheel 1130 effects relative movement of the variable spherical optics 1016. Rotation of cam operated wheel 1140 effects variable movement of variable astigmatic optics 1018.

Rotation of the cam operated wheel 1160 effects movement of the variable optics 1020.

It will be understood that the disclosed invention will admit of a number of embodiments. For example, any projection system between the disclosed wobble plate and eye may be utilized.

I claim:

1. Apparatus for testing the eye along an optical axis comprising in combination:
    a first linearly aligned knife-edge at first angle with respect to said optical axis;
    a second linearly aligned knife-edge at an angle with respect to said first knife-edge;
    means for illuminating each of said knife-edges;
    means for projecting an image of said illuminated knife-edges to the eye;
    optical means between said eye and knife-edges for providing a prescription including variable spherical input and variable cylindrical input between said eye and knife-edges;
    a detector at the opposite end of said optical axis having segments for receiving light from said eye, said detector positioned to receive the light over said knife-edges; and
    means operatively connected between said detector segments and said optical means for varying the prescription between said eye and detector.

2. The invention of claim 1 and wherein said knife-edges are illuminated in the infra-red.

3. Apparatus for testing the eye comprising:
    a first linearly aligned knife-edge;
    a second linearly aligned knife-edge at an angle relative to said first knife-edge;
    means for illuminating said first knife-edge;
    means for illuminating said second knife edge;
    means for projecting both an image of both said knife-edges when illuminated to produce at said eye an image of said knife-edges;
    a detector having at least two photo-discrete detector segments, said detector aligned with said knife-edges along an optical path to said eye to receive discrete signals from the illumination of said knife-edges;
    a variable spherical optic;
    a variable astigmatic optic; and
    means operatively connect between said detector segments and said variable spherical and variable astigmatic optics for changing the power of said optics to obtain equal illumination to said detector segments.

4. The invention of claim 3 and wherein said variable spherical optic comprise:
    an eye piece for passing an image of the eye to be tested to said detector; and
    means for changing the length of the optical path extending between said eye piece and image of said eye of said detector whereby the spherical power at the eye to be changed is adjustable by path length change.

5. The invention of claim 3 and wherein said means for varying the cylindrical power between said eye and light path comprises:
    at least first and second counter-rotating cylindrical lenses; said lenses rotable in response to a difference of intensity received at said photo-discrete detector segments.

6. The invention of claim 5 comprising:
    an eye-piece; and
    a relay lens for projecting a collimated image of the pupil of said eye to be tested to said detector wherein said counter-rotating cylindrical lenses cause images of said knife-edges to fall at variable distances between said relay lens and said eye piece.

7. The apparatus of claim 1 wherein said said means for illuminating each of said knife edges includes means for modulating the illumination of said knife-edges.

8. The apparatus of claim 3 wherein said means for illuminating each said knife edges includes means for modulating the illumination of said knife-edges.

* * * * *